US008095483B2

(12) United States Patent
Weston et al.

(10) Patent No.: US 8,095,483 B2
(45) Date of Patent: Jan. 10, 2012

(54) SUPPORT VECTOR MACHINE—RECURSIVE FEATURE ELIMINATION (SVM-RFE)

(75) Inventors: Jason Weston, New York, NY (US); Isabelle Guyon, Berkeley, CA (US)

(73) Assignee: Health Discovery Corporation, Savannah, GA (US)

( * ) Notice: Subject to any disclaimer, the term of this patent is extended or adjusted under 35 U.S.C. 154(b) by 0 days.

(21) Appl. No.: 12/957,411

(22) Filed: Dec. 1, 2010

(65) Prior Publication Data

US 2011/0119213 A1 May 19, 2011

Related U.S. Application Data

(63) Continuation of application No. 12/890,705, filed on Sep. 26, 2010, now Pat. No. 7,970,718, which is a continuation of application No. 11/928,784, filed on Oct. 30, 2007, now Pat. No. 7,805,388, which is a continuation of application No. 10/494,876, filed as application No. PCT/US02/35576 on Nov. 7, 2002, now Pat. No. 7,475,048, and a continuation-in-part of application No. PCT/US02/16012, filed on May 20, 2002, now Pat. No. 7,318,051, and a continuation-in-part of application No. 10/057,849, filed on Jan. 24, 2002, now Pat. No. 7,117,188, which is a continuation-in-part of application No. 09/633,410, filed on Aug. 7, 2000, now Pat. No. 6,882,990.

(60) Provisional application No. 60/332,021, filed on Nov. 21, 2001, provisional application No. 60/347,562, filed on Nov. 7, 2001, provisional application No. 60/292,133, filed on May 18, 2001, provisional application No. 60/292,221, filed on May 18, 2001, provisional application No. 60/191,219, filed on Mar. 22, 2000, provisional application No. 60/184,596, filed on Feb. 24, 2000, provisional application No. 60/168,703, filed on Dec. 2, 1999, provisional application No. 60/161,806, filed on Oct. 27, 1999.

(51) Int. Cl.
*G06F 15/18* (2006.01)
(52) U.S. Cl. ................. 706/12; 706/15; 706/16; 706/20; 706/45; 706/62
(58) Field of Classification Search ........................ None
See application file for complete search history.

(56) References Cited

U.S. PATENT DOCUMENTS 4,881,178 A 11/1989 Holland
(Continued)

OTHER PUBLICATIONS

Barzilay et al., "On domain knowledge and feature selection using a support vector machine", Pattern Recognition Letters, 1999, pp. 475-484.*

(Continued)

*Primary Examiner* — Omar Fernandez Rivas
(74) *Attorney, Agent, or Firm* — Eleanor M. Musick; Procopio, Cory, Hargreaves & Savitch LLP

(57) ABSTRACT

Identification of a determinative subset of features from within a group of features is performed by training a support vector machine using training samples with class labels to determine a value of each feature, where features are removed based on their the value. One or more features having the smallest values are removed and an updated kernel matrix is generated using the remaining features. The process is repeated until a predetermined number of features remain which are capable of accurately separating the data into different classes.

38 Claims, 25 Drawing Sheets

U.S. PATENT DOCUMENTS

| | | | |
|---|---|---|---|
| 5,138,694 | A | 8/1992 | Hamilton |
| 5,255,347 | A | 10/1993 | Matsuba et al. |
| 5,649,068 | A | 7/1997 | Boser et al. |
| 5,809,144 | A | 9/1998 | Sirbu |
| 5,819,246 | A | 10/1998 | Ashida et al. |
| 5,950,146 | A | 9/1999 | Vapnik et al. |
| 6,087,098 | A | 7/2000 | McKiernan et al. |
| 6,112,195 | A | 8/2000 | Burges |
| 6,128,608 | A | 10/2000 | Barnhill |
| 6,134,344 | A | 10/2000 | Burges |
| 6,157,921 | A | 12/2000 | Barnhill |
| 6,161,130 | A * | 12/2000 | Horvitz et al. ............... 709/206 |
| 6,187,549 | B1 | 2/2001 | Schmidt et al. |
| 6,192,360 | B1 * | 2/2001 | Dumais et al. ....................... 1/1 |
| 6,251,586 | B1 | 6/2001 | Mulshine et al. |
| 6,427,141 | B1 | 7/2002 | Barnhill |
| 6,647,341 | B1 | 11/2003 | Golub et al. |
| 6,658,395 | B1 | 12/2003 | Barnhill |
| 6,714,925 | B1 | 3/2004 | Barnhill et al. |
| 6,760,715 | B1 | 7/2004 | Barnhill et al. |
| 6,789,069 | B1 | 9/2004 | Barnhill et al. |
| 6,882,990 | B1 | 4/2005 | Barnhill et al. |
| 6,944,602 | B2 | 9/2005 | Cristianini |
| 6,996,549 | B2 | 2/2006 | Zhang et al. |
| 7,047,137 | B1 | 5/2006 | Kasif et al. |
| 7,117,188 | B2 * | 10/2006 | Guyon et al. ................... 706/20 |
| 7,299,213 | B2 | 11/2007 | Cristianini |
| 7,318,051 | B2 | 1/2008 | Weston et al. |
| 7,383,237 | B2 | 6/2008 | Zhang et al. |
| 7,444,308 | B2 | 10/2008 | Guyon et al. |
| 7,475,048 | B2 | 1/2009 | Weston et al. |
| 7,542,947 | B2 | 6/2009 | Guyon et al. |
| 7,542,959 | B2 | 6/2009 | Barnhill et al. |
| 7,617,163 | B2 | 11/2009 | Ben-Hur et al. |
| 7,624,074 | B2 | 11/2009 | Weston et al. |
| 7,676,442 | B2 | 3/2010 | Ben-Hur et al. |
| 7,685,077 | B2 | 3/2010 | Li et al. |
| 7,797,257 | B2 | 9/2010 | Barnhill et al. |
| 7,805,388 | B2 | 9/2010 | Weston et al. |
| 2003/0036081 | A1 | 2/2003 | Adorjan |
| 2003/0172043 | A1 * | 9/2003 | Guyon et al. .................... 706/48 |
| 2004/0005547 | A1 | 1/2004 | Boess et al. |
| 2004/0102905 | A1 | 5/2004 | Adorjan |
| 2005/0069936 | A1 | 3/2005 | Diamond et al. |
| 2005/0181386 | A1 | 8/2005 | Diamond et al. |
| 2006/0063156 | A1 | 3/2006 | Willman et al. |
| 2008/0033899 | A1 * | 2/2008 | Barnhill et al. ................. 706/48 |
| 2010/0256988 | A1 | 10/2010 | Barnhill et al. |

OTHER PUBLICATIONS

Blum et al. "selection of relevant features and examples in machine learning", Elsevier, 1997, pp. 245-271.*

Kohavi et al., "Wrappers for feature subset selection", Elsevier, 1997, pp. 273-324.*

John, et al., "Irrelevant Features and the Subset Selection Problem", Machine Learning: Proceedings of the Eleventh International Conference, W.W. Cohen & H. Hirsch, eds., 1994, pp. 121-129.

Sindhwani, et al., "Feature Selection in MLPs and SVMs based on Maximum Output Information", IEEE Trans. on Neural Networks, Jul. 2004, vol. 15, No. 4, pp. 937-948.

Glassman, E.L. and Guttag, J.V., "Reducing the Number of Channels for an Ambulatory Patient-Specific EEG-ased-Epileptic Seizure Detector by Applying Recursive Feature Elimination", Proc. of the IEEE EMBS 28th Annual International Conf., New York City, 2006, pp. 2175-2178.

Model, F., et al., "Feature Selection for DNA Methylation based Cancer Classification", Bioinformatics, 2001, vol. 1, pp. 1-8.

Bradley, P.S., and Mangasarian, O.L., "Feature Selection via Concave Minimization and Support Vector Machines", Proc. 13th International Conference on Machine Learning, 1998, pp. 82-90.

Chapelle, O., et al., "Choosing Multiple Parameters for Support Vector Machines", Machine Learning, Mar. 14, 2000, vol. 46, pp. 131-159.

Boser, et al., "A Training Algorithm for Optimal Margin Classifiers", 5th Annual ACM Workshop on COLT, 1992, pp. 144-152.

Ambroise, et al., "Recursive Feature Elimination With R," May 27, 2005 (Internet), 4 pages.

Ramaswamy, S., et al., "Multiclass cancer diagnosis using tumor gene expression signatures", Proc. Nat. Acad. Sci., 2001, vol. 98, No. 26, pp. 15149-15154.

Camp-Valls, et al., "Profiled Support Vector Machines for Antisense Oligonucleotide Efficacy Prediction", BMC Bioinformatics, 2004, 5:135, pp. 1-9.

Chen, et al., "Performance Scalability of Data-Mining Workloads in Bioinformatics", Intel Technology Journal, 2005, vol. 9, Issue 02, ISSN 1535-864X.

Coz, et al., :Trait Selection for Assessing Beef Meat Quality Using Non-Linear SVM, National Informatic Processing Systems, 2004.

Ding, et al., "Improving the Performance of SVM-RFE to Select Genes in Microarray Data," BMC Bioinformatics (2006) 7(Suppl. 2):512, pp. 1-8.

Dror, et al., "Accurate Identification of Alternatively Spliced Exons Using Support Vector Machine," Bioinformatics/bt/132, vol. 21, No. 7 (2005), pp. 897-901.

Devijver, P., et al., Pattern Recognition. A Statistical Approach, 1982, pp. 218-219, Prentice-Hall International, London.

Alon, U., et al., "Broad patterns of gene expression revealed by clustering analysis of tumor and normal colon tissues probed by oligonucleotide arrays", Proc. Natl. Acad. Sci. USA, Jun. 1999, pp. 6745-6750, vol. 96.

Blum, A.L., et al., "Selection of Relevant Features and Examples in Machine Learning", Artificial intelligence, Dec. 1997, pp. 245-271, vol. 97.

Bredensteiner, E.J., et al., "Multicategory Classification by Support Vector Machines", Computation Optimizations and Applications, 1999, pp. 53-79, vol. 12.

Brown, M.P.S., et al., "Knowledge-based analysis of microarray gene expression data by using support vector machines", Proc. Natl. Acad. Sci. USA, Jan. 4, 2000, pp. 262-267, vol. 97, No. 1.

Furey, T.S., et al., "Support vector machine classification and validation of cancer tissue samples using microarray expression data", Bioinformatics, 2000, pp. 906-914, vol. 16, No. 10.

Golub, T.R., et al., "Molecular Classification of Cancer: Class Discovery and Class Prediction by Gene Expression Monitoring", Science, Oct. 15, 1999, pp. 531-537, vol. 286.

Guyon, I., et al., "An Introduction to Variable and Feature Selection", Journal of Machine Learning Research, 2003, pp. 1157-1182, vol. 3.

Guyon, I., et al., "Gene Selection for Cancer Classification using Support Vector Machines", Machine Learning, 2002, pp. 389-422, vol. 46.

Hastie, T., et al., "Gene Shaving: a New Class of Clustering Methods for Expression Arrays", Technical Report, Stanford University, 2000, pp. 1-40.

Kohavi, R., "The Power of Decision Tables", European Conference on Machine Learning (ECML), 1995, 16 pages.

Kohavi, R., and John, G.H., "Wrappers for Feature Subset Selection", Artificial Intelligence, Dec. 1997, pp. 273-324, vol. 97, Issue 1-2, Special issue on relevance.

Fananapazir, et al., "Formative Evaluation of a Prototype System for Automated Analysis of Mass Spectrometry Data," AMIA* Annual Symposium Proc. (2005):241-5, Oct. 22-26, 2001 proceedings, pp. 241-245.

Le Cun, Y., et al., "Optimal Brain Damage", Advances in Neural Information Processing Systems 2, 1990, pp. 598-605.

Mukherjee, S., et al., "Support Vector Machine Classification of Microarray Data", Technical Report CBCL Paper 182, AI, Memo 1676 M.I.T., 1998.

Gupta, P., et al., "Beam Search for Feature Selection in Automatic SVM Defect Classification", 16th International Conference on Pattern Recognition (ICPR'02), Aug. 2002, p. 20212, vol. 2 (abstract only).

Cook, "Training MLPs via the epectation maximum algorithm", IEEE Fourth International Conference on Artificial Neural Networks, Jun. 1995, pp. 47-52.

Sartori, Neural Network Training Via Quadratic Optimization, Proceedings of International Symposium on Circuits and Systems, San Diego, California, May 10-13,1992, pp. 49-52.

Weston, J., et al., "Feature Selection for SVMs", Proc. 15th Conference on Neural Information Processing Systems (NIPS), 2000, pp. 668-674.

Zhang, X. and Wong, W., "Recursive Sample Classification and Gene Selection based on SVM: Method and Software Description", Technical Report, Department of Biostatistics, Harvard School of Public Health, 2001, 5 pages.

Furlanello, et al., "News on Cardiac Arrhythmias—Part II," Ital. Heart J. (2004) 5(Suppl. 1), pp. 199S-202S.

Gentile, "Fast Feature Selection from Microarray Expression Data via Multiplicative Large Margin Algorithms," Neural Informatic Processing Systems (2003) On-Line Papers, 8 pages.

Hakenberg, et al., "Systematic Feature Evaluation for Gene Name Recognition," BMC Bioinformatics May 24, 2001, vol. 6, Suppl. 1, 11 pages.

Iwao-Koizumi, et al., "Prediction of Docetaxel Response in Human Breast Cancer by Gene Expression Profiling," Journal of Clinical Oncology, vol. 23, No. 3, (2005) pp. 422-431.

Jaleel, et al., "Last Level Cache Performance of Data Mining Workloads On a CMP—A Case Study of Parallel Bioinformatics Workloads," Proc. HPCA*, 12th Int'l Symp.(2006) p. 88-98.

Koo, et al., "Structured Polychotomous Machine Diagnosis of Multiple Cancer Types Using Gene Expression," vol. 22, No. 8 (2006) pp. 950-958.

Lal, et al., "Support Vector Channel Selection in BCI," IEEE Transactions on Biomedical Engineering, vol. 51, No. 6 (Jun. 2004) pp. 1003-1010.

Malossini, et al., "Assessment of SVM Reliability for Microarray Data Analysis," University of Trento, Technical Report #DIT-04-106, (Dec. 2004) pp. 1-10.

Mao, et al., "Multi-Class Cancer Classification by Using Fuzzy Support Vector Machine and Binary Decision Tree with Gene Selection," J. Biomed. Biotechnol. (2005)(2):160-171.

Moler, et al., "Analysis of Molecular Profile Data Using Generative and Discriminative Methods," Physiol. Genomics 4:109-126 (2000) pp. 109-126.

Oh, et al., "Diagnosis of Early Relapse in Ovarian Cancer Using Serum Proteomic Profiling," Genome Informatics 16 (2)(2005) pp. 195-204.

Peng, et al., "Molecular Classification of Cancer Types from Microarray Data Using the Combination of Genetic Algorithms and Support . . . ," FEBS Letters 555 Nov. 12, 2003, pp. 358-362.

Tang, et al., "Granular SVM-RFE Gene Selection Algorithm for Reliable Prostate Cancer Classification on Microarray . . . ," Proceedings of the 5th IEE Symp. Oct. 19-21, 2005, V19-21, pp. 290-293.

Srinivasan, et al., "Characterization and Anaylsis of HMMER and SVM-RFE Parallel Bioinformatics Applications," Proceedings of the IEEE Workload Characterization Symposium, Oct. 6-8, 2005, pp. 87-98.

Masotti, "Exploring Ranklets Performances in Mammographic Mass Classification Using Recursive Feature Elimination," Proceedings 16th IEEE, Maynooth, Ireland, Sub. to Int. Conf. on Image Processing, Sep. 11, 2005, pp. 265-270.

Weston, et al., "Use of the Zero-Norm with Linear Models and Kernel Methods," Journal of Machine Learning Research 3 (2003) 1439-1461, submitted May 2002, published Mar. 2003.

Yong, et al., "Parameters Selection in Gene Selection Using Gaussian Kernal Support Vector Machines by Genetic Algorithm," J. of Zhejiang Univ. Science (2005) 6B(10):961-973.

Zhang, et al., "Sequence Information for the Splicing of Human Pre-mRNA Identified by Support Vector Machine Classification," Genome Research (2003) 13:2637-2650.

Zhang, et al., "Recursive SVM Feature Selection and Sample Classification for Mass-Spectrometry and Microarray Data," BMC Bioinformatics Apr. 10, 2006, vol. 7, pp. 197-209.

Gammerman, Machine Learning: Progress and Prospects, Inaugural Lecture, Royal Holloway, University of London, Dec. 11, 1996, pp. 1-26.

Thimm et al., "Evaluating Pruning Methods", Proc. of Int'l. Symp. on Artif. Neur.Networks 1995., Taiwan, ROC, Dec. 18-20, 1995, pp. A2, 20-25.

Furlanelo, et al., "Methods for Predictive Classification and Molecular Profiling from DNA Microarray Data", Ital. Heart J. (Supp. I), 2004, pp. 199S-202S.

Amari, et al., "Classification of a Portable Electronic Nose Data with SVM-RFE Method: Application to Milk Randicity", Proc. IEEE Sensors 2008 Conference, pp. 446-449.

* cited by examiner

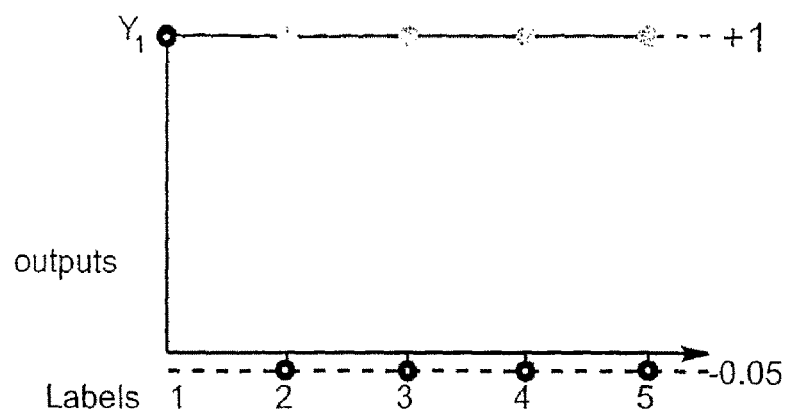
FIG. 16

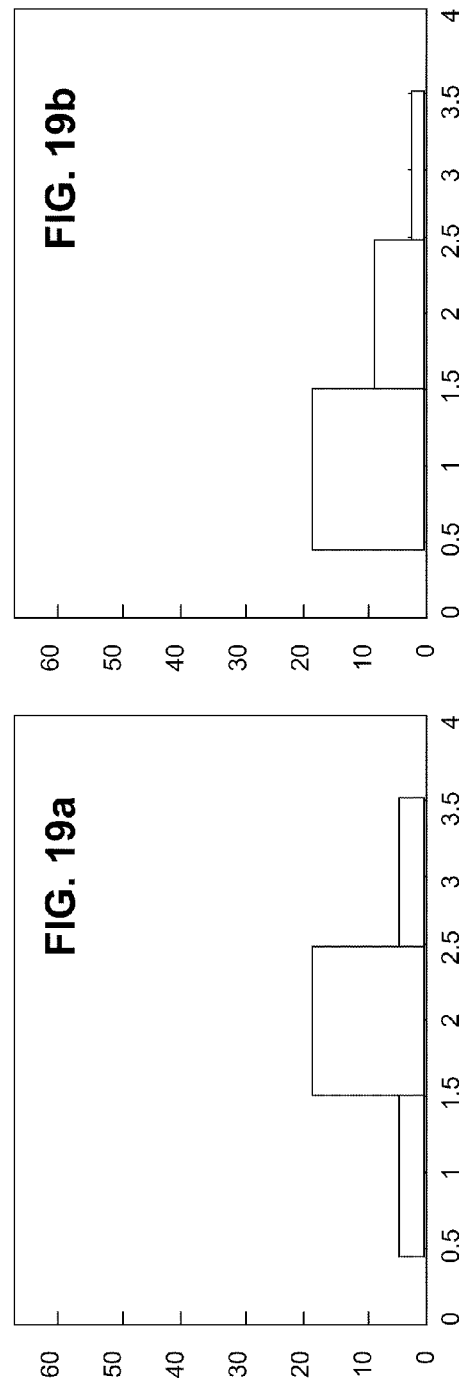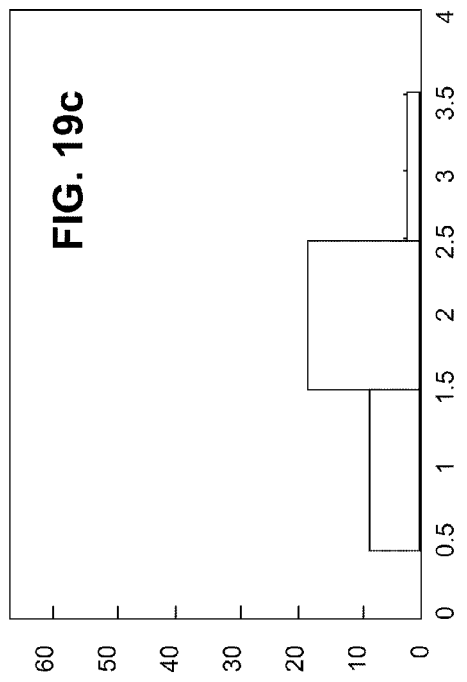

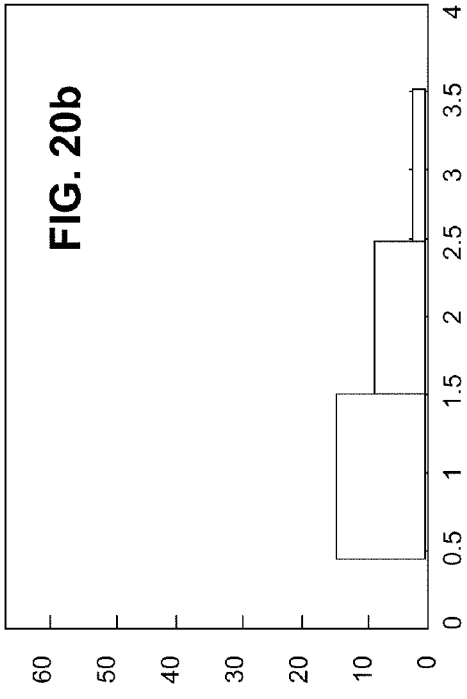
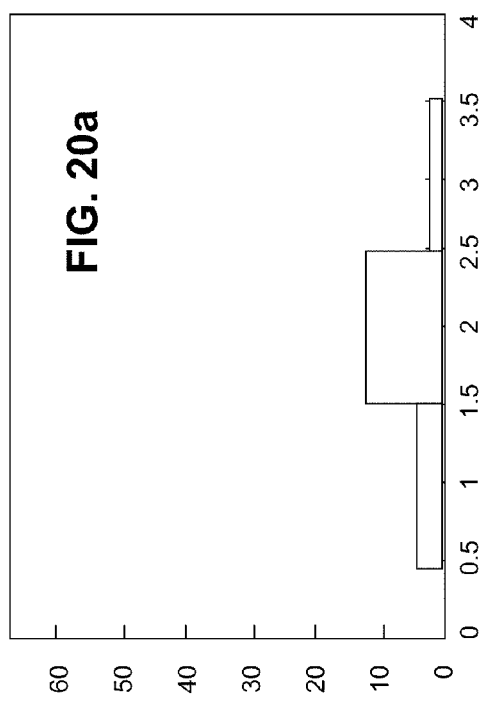
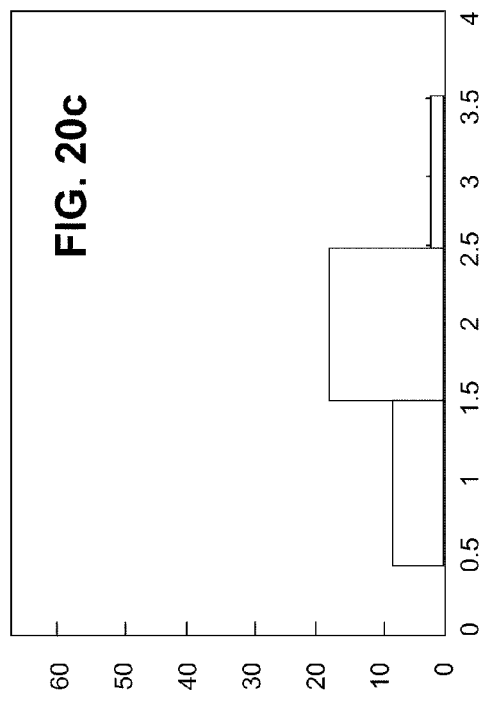

SUPPORT VECTOR MACHINE—RECURSIVE FEATURE ELIMINATION (SVM-RFE)

RELATED APPLICATIONS

This application is a continuation of application Ser. No. 12/890,705, filed Sep. 26, 2010, which is a continuation of application Ser. No. 11/928,784, filed Oct. 30, 2007, now U.S. Pat. No. 7,805,388, which is a continuation of application Ser. No. 10/494,876, filed as application No. PCT/US02/35576 on Nov. 7, 2002, now U.S. Pat. No. 7,475,048, which claims the priority of U.S. provisional application Ser. No. 60/347,562, filed on Nov. 7, 2001, and is a continuation-in-part of application No. PCT/US02/16012, filed May 20, 2002, now U.S. Pat. No. 7,318,051, which claims priority to each of U.S. provisional application Nos. 60/292,133, filed May 18, 2001, No. 60/292,221, filed May 23, 2001, and No. 60/332,021, filed Nov. 21, 2001, and is a continuation-in-part of application Ser. No. 10/057,849, filed Jan. 24, 2002, now U.S. Pat. No. 7,117,188, which is a continuation-in-part of application Ser. No. 09/633,410, filed Aug. 7, 2000, now U.S. Pat. No. 6,882,990, which claims the benefit of provisional application Nos. 60/161,806, filed Oct. 27, 1999, No. 60/168,703, filed Dec. 2, 1999, No. 60/184,596, filed Feb. 24, 2000; and No. 60/191,219, filed Mar. 22, 2000. Each of the above-identified applications is incorporated herein by reference.

FIELD OF THE INVENTION

The present invention relates to the use of learning machines to identify relevant patterns in datasets, and more particularly to a method and system for selection of features within the data sets which best enable classification of the data.

BACKGROUND OF THE INVENTION

Knowledge discovery is the most desirable end product of data collection. Recent advancements in database technology have lead to an explosive growth in systems and methods for generating, collecting and storing vast amounts of data. While database technology enables efficient collection and storage of large data sets, the challenge of facilitating human comprehension of the information in this data is growing ever more difficult. With many existing techniques the problem has become unapproachable. Thus, there remains a need for a new generation of automated knowledge discovery tools.

As a specific example, the Human Genome Project has completed sequencing of the human genome. The complete sequence contains a staggering amount of data, with approximately 31,500 genes in the whole genome. The amount of data relevant to the genome must then be multiplied when considering comparative and other analyses that are needed in order to make use of the sequence data. To illustrate, human chromosome 20 alone comprises nearly 60 million base pairs. Several disease-causing genes have been mapped to chromosome 20 including various autoimmune diseases, certain neurological diseases, type 2 diabetes, several forms of cancer, and more, such that considerable information can be associated with this sequence alone.

One of the more recent advances in determining the functioning parameters of biological systems is the analysis of correlation of genomic information with protein functioning to elucidate the relationship between gene expression, protein function and interaction, and disease states or progression. Proteomics is the study of the group of proteins encoded and regulated by a genome. Genomic activation or expression does not always mean direct changes in protein production levels or activity. Alternative processing of mRNA or post-transcriptional or post-translational regulatory mechanisms may cause the activity of one gene to result in multiple proteins, all of which are slightly different with different migration patterns and biological activities. The human proteome is believed to be 50 to 100 times larger than the human genome. Currently, there are no methods, systems or devices for adequately analyzing the data generated by such biological investigations into the genome and proteome.

In recent years, machine-learning approaches for data analysis have been widely explored for recognizing patterns which, in turn, allow extraction of significant information contained within a large data set that may also include data consists of nothing more than irrelevant detail. Learning machines comprise algorithms that may be trained to generalize using data with known outcomes. Trained learning machine algorithms may then be applied to predict the outcome in cases of unknown outcome, i.e., to classify the data according to learned patterns. Machine-learning approaches, which include neural networks, hidden Markov models, belief networks and kernel-based classifiers such as support vector machines, are ideally suited for domains characterized by the existence of large amounts of data, noisy patterns and the absence of general theories. Support vector machines are disclosed in U.S. Pat. Nos. 6,128,608 and 6,157,921, both of which are assigned to the assignee of the present application and are incorporated herein by reference.

The quantities introduced to describe the data that is input into a learning machine are typically referred to as "features", while the original quantities are sometimes referred to as "attributes". A common problem in classification, and machine learning in general, is the reduction of dimensionality of feature space to overcome the risk of "overfitting". Data overfitting arises when the number n of features is large, such as the thousands of genes studied in a microarray, and the number of training patterns is comparatively small, such as a few dozen patients. In such situations, one can find a decision function that separates the training data, even a linear decision function, but it will perform poorly on test data. The task of choosing the most suitable representation is known as "feature selection".

A number of different approaches to feature selection exists, where one seeks to identify the smallest set of features that still conveys the essential information contained in the original attributes. This is known as "dimensionality reduction" and can be very beneficial as both computational and generalization performance can degrade as the number of features grows, a phenomenon sometimes referred to as the "curse of dimensionality."

Training techniques that use regularization, i.e., restricting the class of admissible solutions, can avoid overfitting the data without requiring space dimensionality reduction. Support Vector Machines (SVMs) use regularization, however even SVMs can benefit from space dimensionality (feature) reduction.

The problem of feature selection is well known in pattern recognition. In many supervised learning problems, feature selection can be important for a variety of reasons including generalization performance, running time requirements and constraints and interpretational issues imposed by the problem itself. Given a particular classification technique, one can select the best subset of features satisfying a given "model selection" criterion by exhaustive enumeration of all subsets of features. However, this method is impractical for large numbers of features, such as thousands of genes, because of the combinatorial explosion of the number of subsets.

One method of feature reduction is projecting on the first few principal directions of the data. Using this method, new features are obtained that are linear combinations of the original features. One disadvantage of projection methods is that none of the original input features can be discarded. Preferred methods incorporate pruning techniques that eliminate some of the original input features while retaining a minimum subset of features that yield better classification performance. For design of diagnostic tests, it is of practical importance to be able to select a small subset of genes for cost effectiveness and to permit the relevance of the genes selected to be verified more easily.

Accordingly, the need remains for a method for selection of the features to be used by a learning machine for pattern recognition which still minimizes classification error.

SUMMARY OF THE INVENTION

In an exemplary embodiment, the present invention comprises preprocessing a training data set in order to allow the most advantageous application of the learning machine. Each training data point comprises a vector having one or more coordinates. Pre-processing the training data set may comprise identifying missing or erroneous data points and taking appropriate steps to correct the flawed data or as appropriate remove the observation or the entire field from the scope of the problem. In a preferred embodiment, pre-processing includes reducing the quantity of features to be processed using feature selection methods selected from the group consisting of recursive feature elimination (RFE), minimizing the number of non-zero parameters of the system ($l_0$-norm minimization), evaluation of cost function to identify a subset of features that are compatible with constraints imposed by the learning set, unbalanced correlation score and transductive feature selection. The features remaining after feature selection are then used to train a learning machine for purposes of pattern classification, regression, clustering and/or novelty detection. In a preferred embodiment, the learning machine is a kernel-based classifier. In the most preferred embodiment, the learning machine comprises a plurality of support vector machines.

A test data set is pre-processed in the same manner as was the training data set. Then, the trained learning machine is tested using the pre-processed test data set. A test output of the trained learning machine may be post-processing to determine if the test output is an optimal solution based on known outcome of the test data set.

In the context of a kernel-based learning machine such as a support vector machine, the present invention also provides for the selection of at least one kernel prior to training the support vector machine. The selection of a kernel may be based on prior knowledge of the specific problem being addressed or analysis of the properties of any available data to be used with the learning machine and is typically dependant on the nature of the knowledge to be discovered from the data.

Kernels are usually defined for patterns that can be represented as a vector of real numbers. For example, linear kernels, radial basis function kernels and polynomial kernels all measure the similarity of a pair of real vectors. Such kernels are appropriate when the patterns are best represented as a sequence of real numbers.

An iterative process comparing postprocessed training outputs or test outputs can be applied to make a determination as to which kernel configuration provides the optimal solution. If the test output is not the optimal solution, the selection of the kernel may be adjusted and the support vector machine may be retrained and retested. Once it is determined that the optimal solution has been identified, a live data set may be collected and pre-processed in the same manner as was the training data set to select the features that best represent the data. The pre-processed live data set is input into the learning machine for processing. The live output of the learning machine may then be post-processed by interpreting the live output into a computationally derived alphanumeric classifier or other form suitable to further utilization of the SVM derived answer.

In an exemplary embodiment a system is provided enhancing knowledge discovered from data using a support vector machine. The exemplary system comprises a storage device for storing a training data set and a test data set, and a processor for executing a support vector machine. The processor is also operable for collecting the training data set from the database, pre-processing the training data set, training the support vector machine using the pre-processed training data set, collecting the test data set from the database, pre-processing the test data set in the same manner as was the training data set, testing the trained support vector machine using the pre-processed test data set, and in response to receiving the test output of the trained support vector machine, post-processing the test output to determine if the test output is an optimal solution. The exemplary system may also comprise a communications device for receiving the test data set and the training data set from a remote source. In such a case, the processor may be operable to store the training data set in the storage device prior pre-processing of the training data set and to store the test data set in the storage device prior pre-processing of the test data set. The exemplary system may also comprise a display device for displaying the post-processed test data. The processor of the exemplary system may further be operable for performing each additional function described above. The communications device may be further operable to send a computationally derived alphanumeric classifier or other SVM-based raw or post-processed output data to a remote source.

In an exemplary embodiment, a system and method are provided for enhancing knowledge discovery from data using multiple learning machines in general and multiple support vector machines in particular. Training data for a learning machine is pre-processed. Multiple support vector machines, each comprising distinct kernels, are trained with the pre-processed training data and are tested with test data that is pre-processed in the same manner. The test outputs from multiple support vector machines are compared in order to determine which of the test outputs if any represents an optimal solution. Selection of one or more kernels may be adjusted and one or more support vector machines may be retrained and retested. When it is determined that an optimal solution has been achieved, live data is pre-processed and input into the support vector machine comprising the kernel that produced the optimal solution. The live output from the learning machine may then be post-processed as needed to place the output in a format appropriate for interpretation by a human or another computer.

BRIEF DESCRIPTION OF THE DRAWINGS

FIGS. 11a and 11b show the results of SVM target functions $f(x)=x_1x_2+x_3$ and $f(x)=x_1$, respectively; and FIGS. 11c-f provide the results for 95%, 90%, 80% and 0% sparse poly degree 2, respectively.

FIGS. 12a and 12b show the results of SVM target functions $f(x)=x_1x_2+x_3$ and $f(x)=x_1$, respectively; and FIGS. 12c-f provide the results for 95%, 90%, 80% and 0% sparse poly degree 2, respectively.

FIG. 16 is a plot of showing the Hamming distance for a dataset having five labels and two possible label sets.

FIGS. 19a-c are histograms of the leave-one-out estimate of the Hamming Loss for the Prostate Cancer Database relating to the embodiment of feature section in multi-label cases where FIG. 19a is a histogram of the errors for a direct approach; FIG. 19b is a histogram of the errors for the binary approach; and FIG. 19c is a histogram of the errors for the binary approach when the system is forced to output at least one label.

FIG. 20a-c are histograms of the leave-one-out estimate of the Hamming Loss for the Prostate Cancer Database relating to the embodiment of feature section in multi-label cases where FIG. 20a is a histogram of the errors for the direct approach; FIG. 20b is a histogram of the errors for the binary approach; and FIG. 20c is a histogram of the errors for the binary approach when the system is forced to output at least one label.

FIG. 21 shows the distribution of the mistakes using the leave-one-out estimate of the Hamming Loss for the Prostate Cancer Database using 4 labels with Feature selection.

FIG. 22a provides the results for 4 to 20 features compared with the inductive SVM method.

FIG. 26 is a plot of the criteria for gene ranking, where

FIG. 28 is a pair of graphs showing results of SF-SVM analysis of expression data for two genes potentially related to the diseases, selected using the multiclass method, where

DETAILED DESCRIPTION OF THE PREFERRED EMBODIMENTS

Figure 1:
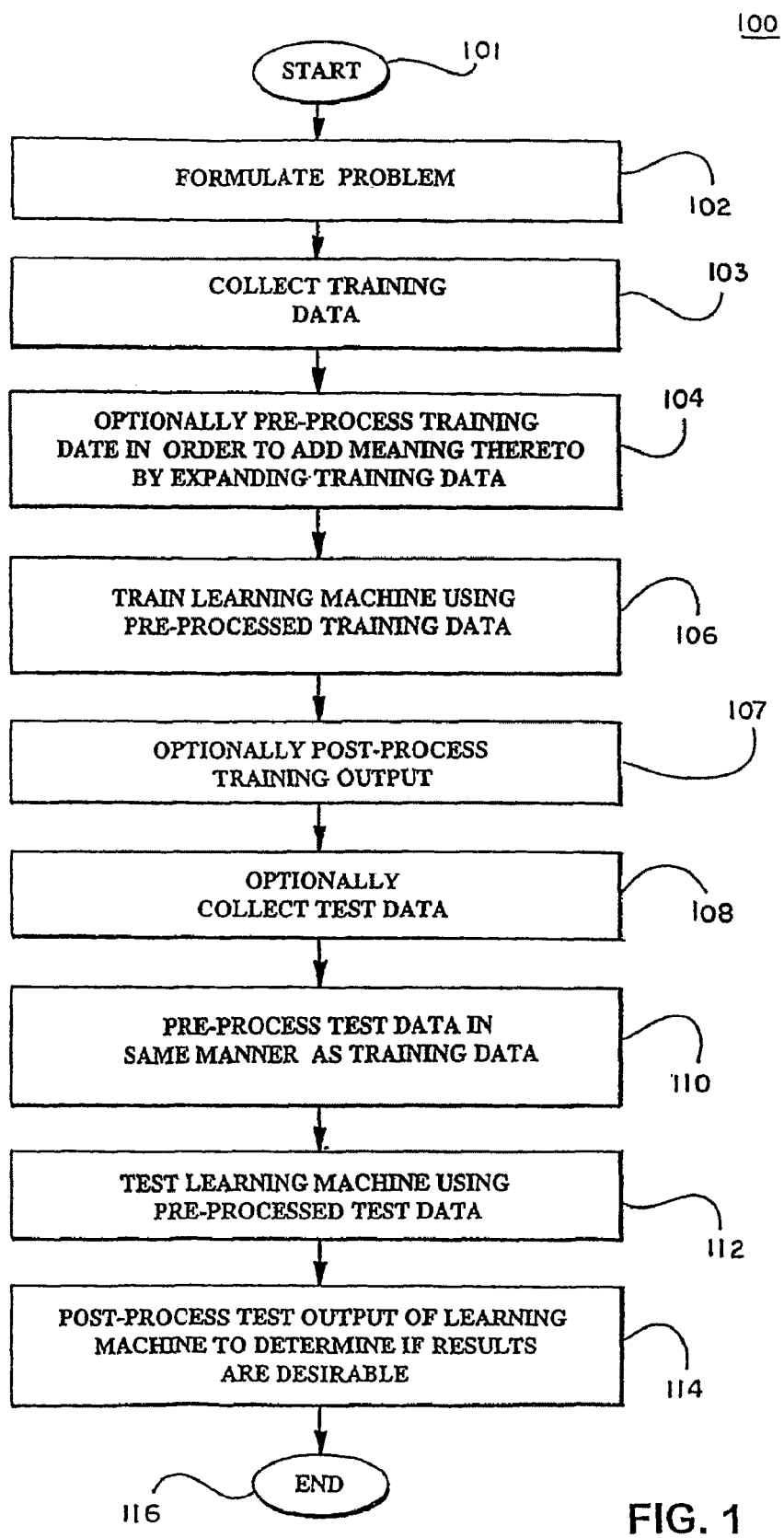
FIG. 1 is a flowchart illustrating an exemplary general method for increasing knowledge that may be discovered from data using a learning machine.

The present invention provides methods, systems and devices for discovering knowledge from data using learning machines. Particularly, the present invention is directed to methods, systems and devices for knowledge discovery from data using learning machines that are provided information regarding changes in biological systems. More particularly, the present invention comprises methods of use of such knowledge for diagnosing and prognosing changes in biological systems such as diseases. Additionally, the present invention comprises methods, compositions and devices for applying such knowledge to the testing and treating of individuals with changes in their individual biological systems. Preferred embodiments comprise detection of genes involved with prostate cancer and use of such information for treatment of patients with prostate cancer.

As used herein, "biological data" means any data derived from measuring biological conditions of human, animals or other biological organisms including microorganisms, viruses, plants and other living organisms. The measurements may be made by any tests, assays or observations that are known to physicians, scientists, diagnosticians, or the like. Biological data may include, but is not limited to, clinical tests and observations, physical and chemical measurements, genomic determinations, proteomic determinations, drug levels, hormonal and immunological tests, neurochemical or neurophysical measurements, mineral and vitamin level determinations, genetic and familial histories, and other determinations that may give insight into the state of the individual or individuals that are undergoing testing. Herein, the use of the term "data" is used interchangeably with "biological data".

While several examples of learning machines exist and advancements are expected in this field, the exemplary embodiments of the present invention focus on kernel-based learning machines and more particularly on the support vector machine.

The present invention can be used to analyze biological data generated at multiple stages of investigation into biological functions, and further, to integrate the different kinds of data for novel diagnostic and prognostic determinations. For example, biological data obtained from clinical case information, such as diagnostic test data, family or genetic histories, prior or current medical treatments, and the clinical outcomes of such activities, can be utilized in the methods, systems and devices of the present invention. Additionally, clinical samples such as diseased tissues or fluids, and normal tissues and fluids, and cell separations can provide biological data that can be utilized by the current invention. Proteomic determinations such as 2-D gel, mass spectrophotometry and antibody screening can be used to establish databases that can be utilized by the present invention. Genomic databases can also be used alone or in combination with the above-described data and databases by the present invention to provide comprehensive diagnosis, prognosis or predictive capabilities to the user of the present invention.

A first aspect of the present invention facilitates analysis of data by pre-processing the data prior to using the data to train a learning machine and/or optionally post-processing the output from a learning machine. Generally stated, pre-processing data comprises reformatting or augmenting the data in order to allow the learning machine to be applied most advantageously. More specifically, pre-processing involves selecting a method for reducing the dimensionality of the feature space, i.e., selecting the features which best represent the data. Methods which may be used for this purpose include recursive feature elimination (RFE), minimizing the number of non-zero parameters of the system, evaluation of cost function to identify a subset of features that are compatible with constraints imposed by the learning set, unbalanced correlation score, inductive feature selection and transductive feature selection. The features remaining after feature selection are then used to train a learning machine for purposes of pattern classification, regression, clustering and/or novelty detection.

In a manner similar to pre-processing, post-processing involves interpreting the output of a learning machine in order to discover meaningful characteristics thereof. The meaningful characteristics to be ascertained from the output may be problem- or data-specific. Post-processing involves interpreting the output into a form that, for example, may be understood by or is otherwise useful to a human observer, or converting the output into a form which may be readily received by another device for, e.g., archival or transmission.

FIG. 1 is a flowchart illustrating a general method 100 for analyzing data using learning machines. The method 100 begins at starting block 101 and progresses to step 102 where a specific problem is formalized for application of analysis through machine learning. Particularly important is a proper formulation of the desired output of the learning machine. For instance, in predicting future performance of an individual equity instrument, or a market index, a learning machine is likely to achieve better performance when predicting the expected future change rather than predicting the future price level. The future price expectation can later be derived in a post-processing step as will be discussed later in this specification.

After problem formalization, step 103 addresses training data collection. Training data comprises a set of data points having known characteristics. This data may come from customers, research facilities, academic institutions, national laboratories, commercial entities or other public or confidential sources. The source of the data and the types of data provided are not crucial to the methods. Training data may be collected from one or more local and/or remote sources. The data may be provided through any means such as via the internet, server linkages or discs, CD/ROMs, DVDs or other storage means. The collection of training data may be accomplished manually or by way of an automated process, such as known electronic data transfer methods. Accordingly, an exemplary embodiment of the learning machine for use in conjunction with the present invention may be implemented in a networked computer environment. Exemplary operating environments for implementing various embodiments of the learning machine will be described in detail with respect to FIGS. 4-5.

At step 104, the collected training data is optionally pre-processed in order to allow the learning machine to be applied most advantageously toward extraction of the knowledge inherent to the training data. During this preprocessing stage a variety of different transformations can be performed on the data to enhance its usefulness. Such transformations, examples of which include addition of expert information, labeling, binary conversion, Fourier transformations, etc., will be readily apparent to those of skill in the art. However, the preprocessing of interest in the present invention is the reduction of dimensionality by way of feature selection, different methods of which are described in detail below.

Returning to FIG. 1, an exemplary method 100 continues at step 106, where the learning machine is trained using the pre-processed data. As is known in the art, a learning machine is trained by adjusting its operating parameters until a desirable training output is achieved. The determination of whether a training output is desirable may be accomplished either manually or automatically by comparing the training output to the known characteristics of the training data. A learning machine is considered to be trained when its training output is within a predetermined error threshold from the known characteristics of the training data. In certain situations, it may be desirable, if not necessary, to post-process the training output of the learning machine at step 107. As mentioned, post-processing the output of a learning machine involves interpreting the output into a meaningful form. In the context of a regression problem, for example, it may be necessary to determine range categorizations for the output of a learning machine in order to determine if the input data points were correctly categorized. In the example of a pattern recognition problem, it is often not necessary to post-process the training output of a learning machine.

At step 108, test data is optionally collected in preparation for testing the trained learning machine. Test data may be collected from one or more local and/or remote sources. In practice, test data and training data may be collected from the same source(s) at the same time. Thus, test data and training data sets can be divided out of a common data set and stored in a local storage medium for use as different input data sets for a learning machine. Regardless of how the test data is collected, any test data used must be pre-processed at step 110 in the same manner as was the training data. As should be apparent to those skilled in the art, a proper test of the learning may only be accomplished by using testing data of the same format as the training data. Then, at step 112 the learning machine is tested using the pre-processed test data, if any. The test output of the learning machine is optionally post-processed at step 114 in order to determine if the results are desirable. Again, the post processing step involves interpreting the test output into a meaningful form. The meaningful form may be one that is readily understood by a human or one that is compatible with another processor. Regardless, the test output must be post-processed into a form which may be compared to the test data to determine whether the results were desirable. Examples of post-processing steps include but are not limited of the following: optimal categorization determinations, scaling techniques (linear and non-linear), transformations (linear and non-linear), and probability estimations. The method 100 ends at step 116.

Figure 2:
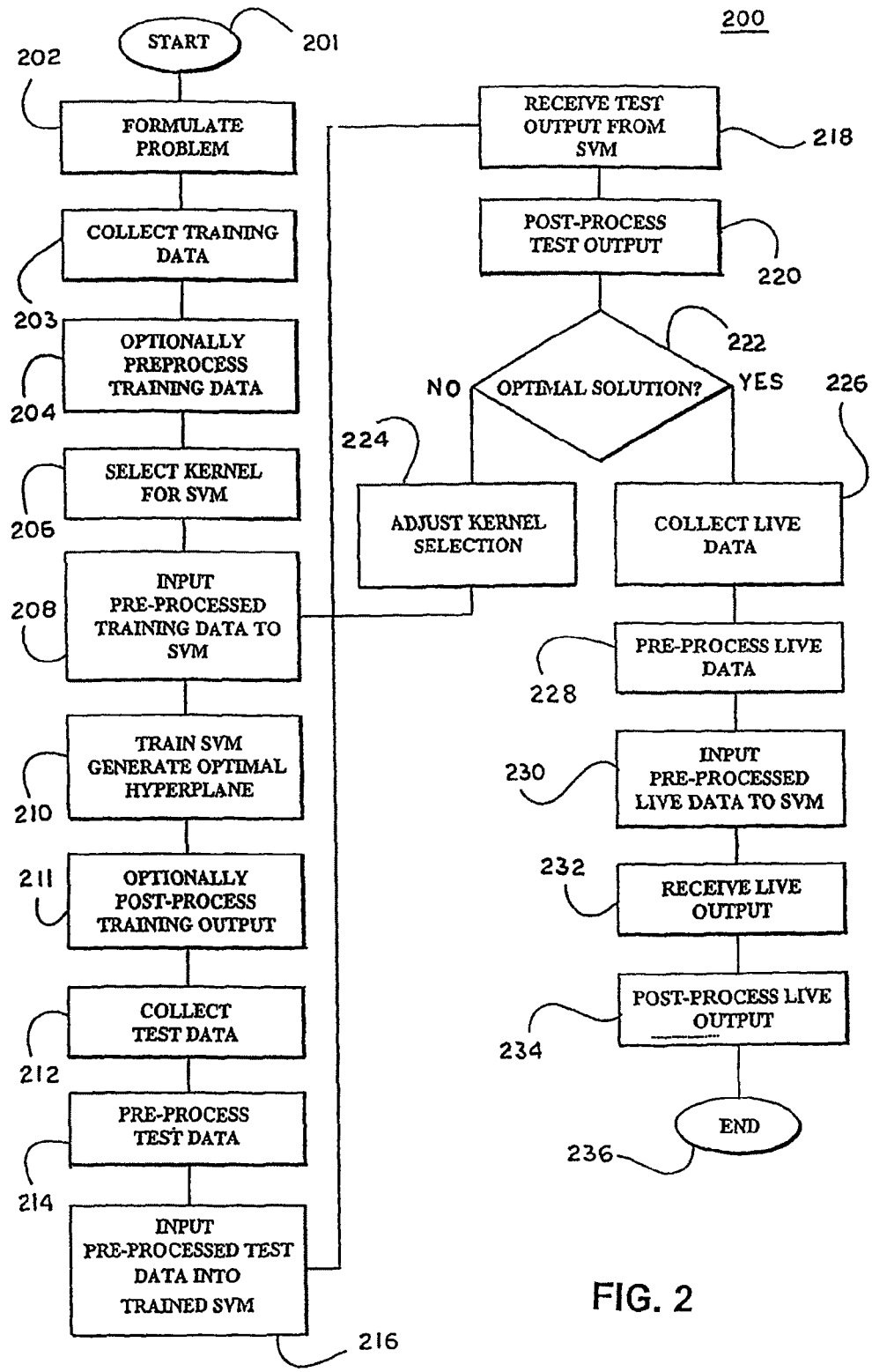
FIG. 2 is a flowchart illustrating an exemplary method for increasing knowledge that may be discovered from data using a support vector machine.

FIG. 2 is a flow chart illustrating an exemplary method 200 for enhancing knowledge that may be discovered from data using a specific type of learning machine known as a support vector machine (SVM). A SVM implements a specialized algorithm for providing generalization when estimating a multi-dimensional function from a limited collection of data. A SVM may be particularly useful in solving dependency estimation problems. More specifically, a SVM may be used accurately in estimating indicator functions (e.g. pattern recognition problems) and real-valued functions (e.g. function approximation problems, regression estimation problems, density estimation problems, and solving inverse problems). The SVM was originally developed by Vladimir Vapnik, Bernard Boser and Isabelle Guyon. The concepts underlying the SVM are explained in detail in Vapnik's book, entitled *Statistical Learning Theory* (John Wiley & Sons, Inc. 1998), which is herein incorporated by reference in its entirety. Accordingly, a familiarity with SVMs and the terminology used therewith are presumed throughout this specification.

The exemplary method 200 begins at starting block 201 and advances to step 202, where a problem is formulated and then to step 203, where a training data set is collected. As was described with reference to FIG. 1, training data may be collected from one or more local and/or remote sources, through a manual or automated process. At step 204 the training data is optionally pre-processed. Those skilled in the art should appreciate that SVMs are capable of processing input data having extremely large dimensionality, however, according to the present invention, pre-processing includes the use of feature selection methods to reduce the dimensionality of feature space.

At step 206 a kernel is selected for the SVM. As is known in the art, different kernels will cause a SVM to produce varying degrees of quality in the output for a given set of input data. Therefore, the selection of an appropriate kernel may be essential to the desired quality of the output of the SVM. In one embodiment of the learning machine, a kernel may be chosen based on prior performance knowledge. As is known in the art, exemplary kernels include polynomial kernels, radial basis classifier kernels, linear kernels, etc. In an alternate embodiment, a customized kernel may be created that is specific to a particular problem or type of data set. In yet another embodiment, the multiple SVMs may be trained and tested simultaneously, each using a different kernel. The quality of the outputs for each simultaneously trained and tested SVM may be compared using a variety of selectable or weighted metrics (see step 222) to determine the most desirable kernel. In still another embodiment which is particularly advantageous for use with structured data, locational kernels are defined to exploit patterns within the structure. The locational kernels are then used to construct kernels on the structured object.

Next, at step 208 the pre-processed training data is input into the SVM. At step 210, the SVM is trained using the pre-processed training data to generate an optimal hyperplane. Optionally, the training output of the SVM may then be post-processed at step 211. Again, post-processing of training output may be desirable, or even necessary, at this point in order to properly calculate ranges or categories for the output. At step 212 test data is collected similarly to previous descriptions of data collection. The test data is pre-processed at step 214 in the same manner as was the training data above. Then, at step 216 the pre-processed test data is input into the SVM for processing in order to determine whether the SVM was trained in a desirable manner. The test output is received from the SVM at step 218 and is optionally post-processed at step 220.

Based on the post-processed test output, it is determined at step 222 whether an optimal minimum was achieved by the SVM. Those skilled in the art should appreciate that a SVM is operable to ascertain an output having a global minimum error. However, as mentioned above, output results of a SVM for a given data set will typically vary with kernel selection. Therefore, there are in fact multiple global minimums that may be ascertained by a SVM for a given set of data. As used herein, the term "optimal minimum" or "optimal solution" refers to a selected global minimum that is considered to be optimal (e.g. the optimal solution for a given set of problem specific, pre-established criteria) when compared to other global minimums ascertained by a SVM. Accordingly, at step 222, determining whether the optimal minimum has been ascertained may involve comparing the output of a SVM with a historical or predetermined value. Such a predetermined value may be dependant on the test data set. For example, in the context of a pattern recognition problem where data points are classified by a SVM as either having a certain characteristic or not having the characteristic, a global minimum error of 50% would not be optimal. In this example, a global minimum of 50% is no better than the result that would be achieved by flipping a coin to determine whether the data point had that characteristic. As another example, in the case where multiple SVMs are trained and tested simultaneously with varying kernels, the outputs for each SVM may be compared with output of other SVM to determine the practical optimal solution for that particular set of kernels. The determination of whether an optimal solution has been ascertained may be performed manually or through an automated comparison process.

If it is determined that the optimal minimum has not been achieved by the trained SVM, the method advances to step 224, where the kernel selection is adjusted. Adjustment of the kernel selection may comprise selecting one or more new kernels or adjusting kernel parameters. Furthermore, in the case where multiple SVMs were trained and tested simultaneously, selected kernels may be replaced or modified while other kernels may be re-used for control purposes. After the kernel selection is adjusted, the method 200 is repeated from step 208, where the pre-processed training data is input into the SVM for training purposes. When it is determined at step 222 that the optimal minimum has been achieved, the method advances to step 226, where live data is collected similarly as described above. By definition, live data has not been previously evaluated, so that the desired output characteristics that were known with respect to the training data and the test data are not known.

At step 228 the live data is pre-processed in the same manner as was the training data and the test data. At step 230, the live pre-processed data is input into the SVM for processing. The live output of the SVM is received at step 232 and is post-processed at step 234. The method 200 ends at step 236.

Figure 3:
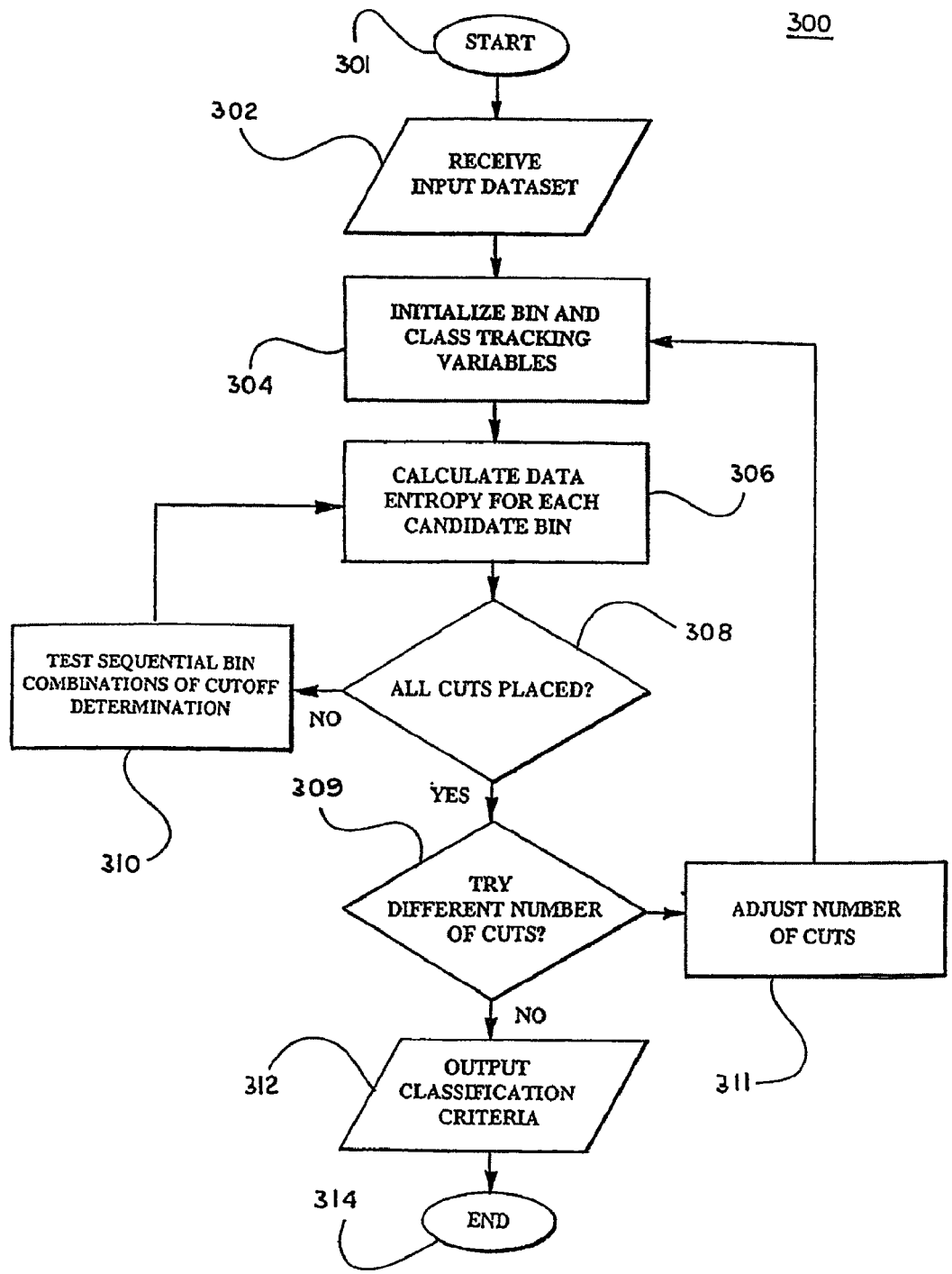
FIG. 3 is a flowchart illustrating an exemplary optimal categorization method that may be used in a stand-alone configuration or in conjunction with a learning machine for pre-processing or post-processing techniques in accordance with an exemplary embodiment of the present invention.

FIG. 3 is a flow chart illustrating an exemplary optimal categorization method 300 that may be used for pre-processing data or post-processing output from a learning machine. Additionally, as will be described below, the exemplary optimal categorization method may be used as a stand-alone categorization technique, independent from learning machines. The exemplary optimal categorization method 300 begins at starting block 301 and progresses to step 302, where an input data set is received. The input data set comprises a sequence of data samples from a continuous variable. The data samples fall within two or more classification categories. Next, at step 304 the bin and class-tracking variables are initialized. As is known in the art, bin variables relate to resolution, while class-tracking variables relate to the number of classifications within the data set. Determining the values for initialization of the bin and class-tracking variables may be performed manually or through an automated process, such as a computer program for analyzing the input data set. At step 306, the data entropy for each bin is calculated. Entropy is a mathematical quantity that measures the uncertainty of a random distribution. In the exemplary method 300, entropy is used to gauge the gradations of the input variable so that maximum classification capability is achieved.

The method 300 produces a series of "cuts" on the continuous variable, such that the continuous variable may be divided into discrete categories. The cuts selected by the exemplary method 300 are optimal in the sense that the average entropy of each resulting discrete category is minimized. At step 308, a determination is made as to whether all cuts have been placed within input data set comprising the continuous variable. If all cuts have not been placed, sequential bin combinations are tested for cutoff determination at step 310. From step 310, the exemplary method 300 loops back through step 306 and returns to step 308 where it is again determined whether all cuts have been placed within input data set comprising the continuous variable. When all cuts have been placed, the entropy for the entire system is evaluated at step 309 and compared to previous results from testing more or fewer cuts. If it cannot be concluded that a minimum entropy state has been determined, then other possible cut selections must be evaluated and the method proceeds to step 311. From step 311 a heretofore untested selection for number of cuts is chosen and the above process is repeated from step 304. When either the limits of the resolution determined by the bin width has been tested or the convergence to a minimum solution has been identified, the optimal classification criteria is output at step 312 and the exemplary optimal categorization method 300 ends at step 314.

The optimal categorization method 300 takes advantage of dynamic programming techniques. As is known in the art, dynamic programming techniques may be used to significantly improve the efficiency of solving certain complex problems through carefully structuring an algorithm to reduce redundant calculations. In the optimal categorization problem, the straightforward approach of exhaustively searching through all possible cuts in the continuous variable data would result in an algorithm of exponential complexity and would render the problem intractable for even moderate sized inputs. By taking advantage of the additive property of the target function, in this problem the average entropy, the problem may be divide into a series of sub-problems. By properly formulating algorithmic sub-structures for solving each sub-problem and storing the solutions of the sub-problems, a significant amount of redundant computation may be identified and avoided. As a result of using the dynamic programming approach, the exemplary optimal categorization method 300 may be implemented as an algorithm having a polynomial complexity, which may be used to solve large sized problems.

As mentioned above, the exemplary optimal categorization method 300 may be used in pre-processing data and/or post-processing the output of a learning machine. For example, as a pre-processing transformation step, the exemplary optimal categorization method 300 may be used to extract classification information from raw data. As a post-processing technique, the exemplary optimal range categorization method may be used to determine the optimal cut-off values for markers objectively based on data, rather than relying on ad hoc approaches. As should be apparent, the exemplary optimal categorization method 300 has applications in pattern recognition, classification, regression problems, etc. The exemplary optimal categorization method 300 may also be used as a stand-alone categorization technique, independent from SVMs and other learning machines.

Figure 4:
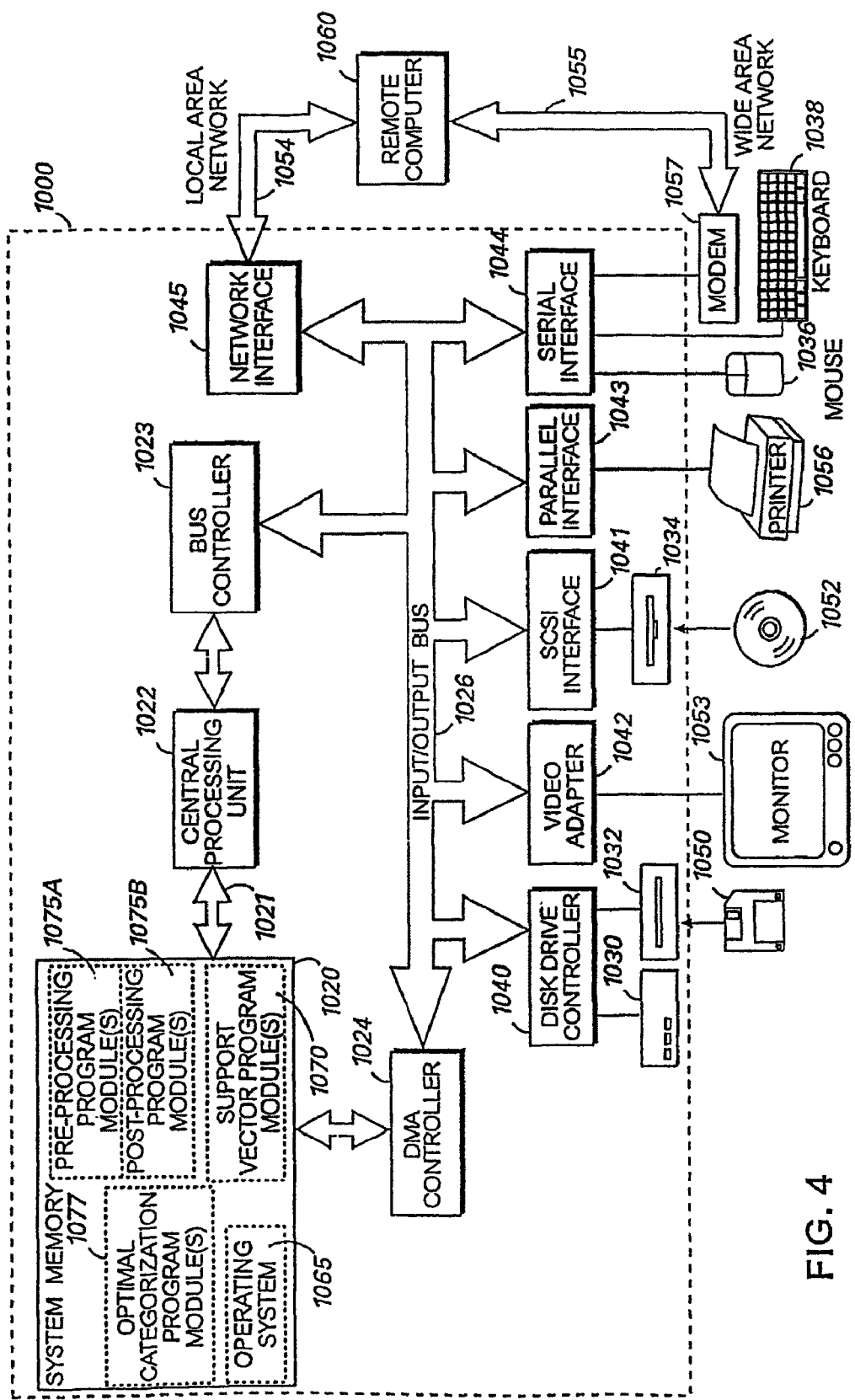
FIG. 4 is a functional block diagram illustrating an exemplary operating environment for an embodiment of the present invention.

FIG. 4 and the following discussion are intended to provide a brief and general description of a suitable computing environment for implementing biological data analysis according to the present invention. Although the system shown in FIG. 4 is a conventional personal computer 1000, those skilled in the art will recognize that the invention also may be implemented using other types of computer system configurations. The computer 1000 includes a central processing unit 1022, a system memory 1020, and an Input/Output ("I/O") bus 1026. A system bus 1021 couples the central processing unit 1022 to the system memory 1020. A bus controller 1023 controls the flow of data on the I/O bus 1026 and between the central processing unit 1022 and a variety of internal and external I/O devices. The I/O devices connected to the I/O bus 1026 may have direct access to the system memory 1020 using a Direct Memory Access ("DMA") controller 1024.

The I/O devices are connected to the I/O bus 1026 via a set of device interfaces. The device interfaces may include both hardware components and software components. For instance, a hard disk drive 1030 and a floppy disk drive 1032 for reading or writing removable media 1050 may be connected to the I/O bus 1026 through disk drive controllers 1040. An optical disk drive 1034 for reading or writing optical media 1052 may be connected to the I/O bus 1026 using a Small Computer System Interface ("SCSI") 1041. Alternatively, an IDE (Integrated Drive Electronics, i.e., a hard disk drive interface for PCs), ATAPI (ATtAchment Packet Interface, i.e., CD-ROM and tape drive interface), or EIDE (Enhanced IDE) interface may be associated with an optical drive such as may be the case with a CD-ROM drive. The drives and their associated computer-readable media provide nonvolatile storage for the computer 1000. In addition to the computer-readable media described above, other types of computer-readable media may also be used, such as ZIP drives, or the like.

A display device 1053, such as a monitor, is connected to the I/O bus 1026 via another interface, such as a video adapter 1042. A parallel interface 1043 connects synchronous peripheral devices, such as a laser printer 1056, to the I/O bus 1026. A serial interface 1044 connects communication devices to the I/O bus 1026. A user may enter commands and information into the computer 1000 via the serial interface 1044 or by using an input device, such as a keyboard 1038, a mouse 1036 or a modem 1057. Other peripheral devices (not shown) may also be connected to the computer 1000, such as audio input/output devices or image capture devices.

A number of program modules may be stored on the drives and in the system memory 1020. The system memory 1020 can include both Random Access Memory ("RAM") and Read Only Memory ("ROM"). The program modules control how the computer 1000 functions and interacts with the user, with I/O devices or with other computers. Program modules include routines, operating systems 1065, application programs, data structures, and other software or firmware components. In an illustrative embodiment, the learning machine may comprise one or more pre-processing program modules 1075A, one or more post-processing program modules 1075B, and/or one or more optimal categorization program modules 1077 and one or more SVM program modules 1070 stored on the drives or in the system memory 1020 of the computer 1000. Specifically, pre-processing program modules 1075A, post-processing program modules 1075B, together with the SVM program modules 1070 may comprise computer-executable instructions for pre-processing data and post-processing output from a learning machine and implementing the learning algorithm according to the exemplary methods described with reference to FIGS. 1 and 2. Furthermore, optimal categorization program modules 1077 may comprise computer-executable instructions for optimally categorizing a data set according to the exemplary methods described with reference to FIG. 3.

The computer 1000 may operate in a networked environment using logical connections to one or more remote computers, such as remote computer 1060. The remote computer 1060 may be a server, a router, a peer device or other common network node, and typically includes many or all of the elements described in connection with the computer 1000. In a networked environment, program modules and data may be stored on the remote computer 1060. The logical connections depicted in FIG. 4 include a local area network ("LAN") 1054 and a wide area network ("WAN") 1055. In a LAN environment, a network interface 1045, such as an Ethernet adapter card, can be used to connect the computer 1000 to the remote computer 1060. In a WAN environment, the computer 1000 may use a telecommunications device, such as a modem 1057, to establish a connection. It will be appreciated that the network connections shown are illustrative and other devices of establishing a communications link between the computers may be used.

In another embodiment, a plurality of SVMs can be configured to hierarchically process multiple data sets in parallel or sequentially. In particular, one or more first-level SVMs may be trained and tested to process a first type of data and one or more first-level SVMs can be trained and tested to process a second type of data. Additional types of data may be processed by other first-level SVMs. The output from some or all of the first-level SVMs may be combined in a logical manner to produce an input data set for one or more second-level SVMs. In a similar fashion, output from a plurality of second-level SVMs may be combined in a logical manner to produce input data for one or more third-level SVM. The hierarchy of SVMs may be expanded to any number of levels as may be appropriate. In this manner, lower hierarchical level SVMs may be used to pre-process data that is to be input into higher level SVMs. Also, higher hierarchical level SVMs may be used to post-process data that is output from lower hierarchical level SVMs.

Each SVM in the hierarchy or each hierarchical level of SVMs may be configured with a distinct kernel. For example, SVMs used to process a first type of data may be configured with a first type of kernel while SVMs used to process a second type of data may utilize a second, different type of kernel. In addition, multiple SVMs in the same or different hierarchical level may be configured to process the same type of data using distinct kernels.

Figure 5:
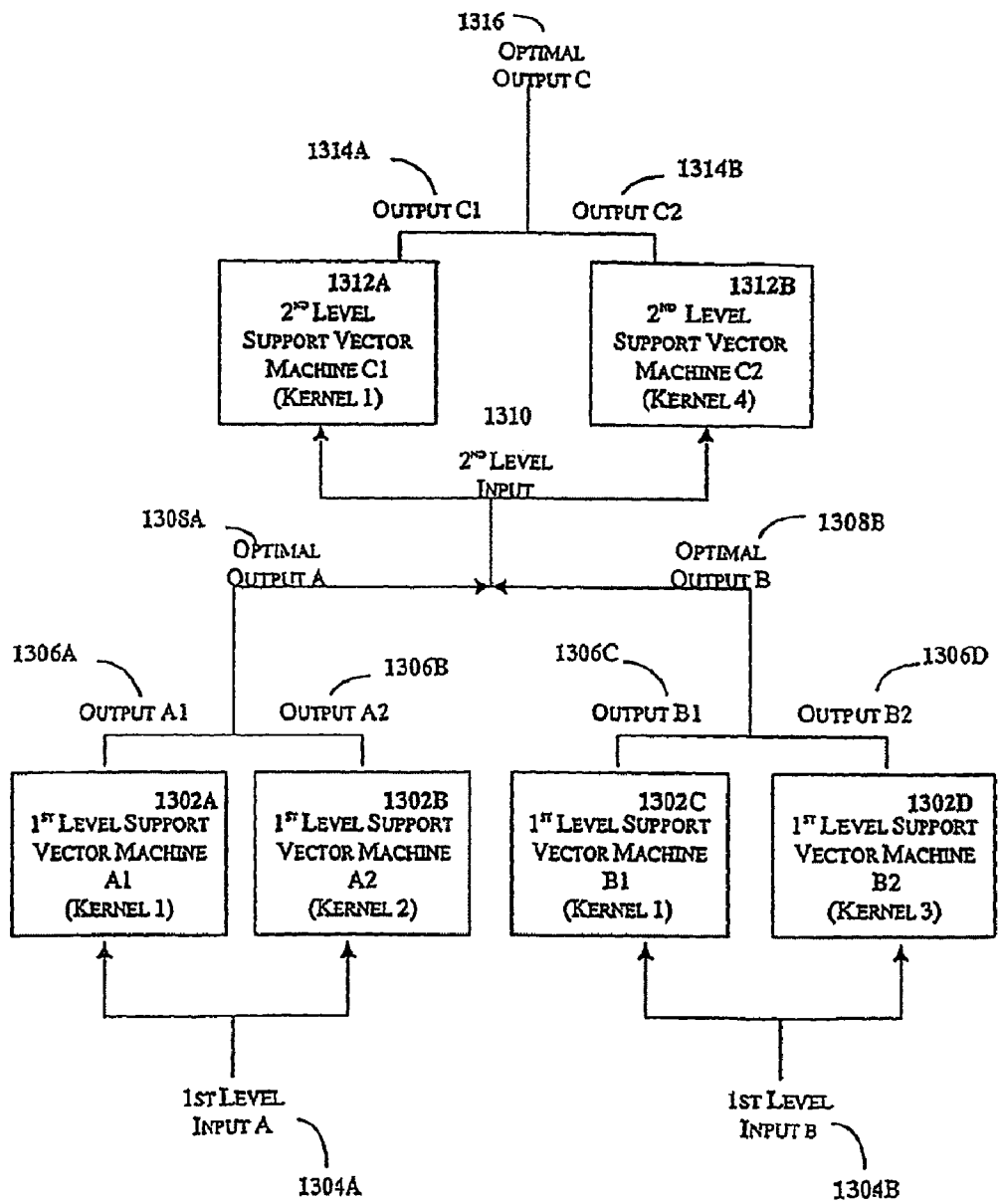
FIG. 5 is a functional block diagram illustrating a hierarchical system of multiple support vector machines.

FIG. 5 illustrates an exemplary hierarchical system of SVMs. As shown, one or more first-level SVMs 1302a and 1302b may be trained and tested to process a first type of input data 1304a, such as mammography data, pertaining to a sample of medical patients. One or more of these SVMs may comprise a distinct kernel, indicated as "KERNEL 1" and "KERNEL 2". Also, one or more additional first-level SVMs 1302c and 1302d may be trained and tested to process a second type of data 1304b, which may be, for example, genomic data for the same or a different sample of medical patients. Again, one or more of the additional SVMs may comprise a distinct kernel, indicated as "KERNEL 1" and "KERNEL 3". The output from each of the like first-level SVMs may be compared with each other, e.g., 1306a compared with 1306b; 1306c compared with 1306d, in order to determine optimal outputs 1308a and 1308b. Then, the optimal outputs from the two groups or first-level SVMs, i.e., outputs 1308a and 1308b, may be combined to form a new multi-dimensional input data set 1310, for example, relating to mammography and genomic data. The new data set may then be processed by one or more appropriately trained and tested second-level SVMs 1312a and 1312b. The resulting outputs 1314a and 1314b from second-level SVMs 1312a and 1312b may be compared to determine an optimal output 1316. Optimal output 1316 may identify causal relationships between the mammography and genomic data points. As should be apparent to those of skill in the art, other combinations of hierarchical SVMs may be used to process either in parallel or serially, data of different types in any field or industry in which analysis of data is desired.

Feature Selection:

Feature Selection by Recursive Feature Elimination. The problem of selection of a small amount of data from a large data source, such as a gene subset from a microarray, is particularly solved using the methods, devices and systems described herein. Previous attempts to address this problem used correlation techniques, i.e., assigning a coefficient to the strength of association between variables. In a first embodiment described herein, support vector machines methods based on recursive feature elimination (RFE) are used. In examining genetic data to find determinative genes, these methods eliminate gene redundancy automatically and yield better and more compact gene subsets. The methods, devices and systems described herein can be used with publicly-available data to find relevant answers, such as genes determinative of a cancer diagnosis, or with specifically generated data.

The illustrative examples are directed at gene expression data manipulations, however, any data can be used in the methods, systems and devices described herein. There are studies of gene clusters discovered by unsupervised or supervised learning techniques. Preferred methods comprise application of SVMs in determining a small subset of highly discriminant genes that can be used to build very reliable cancer classifiers. Identification of discriminant genes is beneficial in confirming recent discoveries in research or in suggesting avenues for research or treatment. Diagnostic tests that measure the abundance of a given protein in bodily fluids may be derived from the discovery of a small subset of discriminant genes.

In classification methods using SVMs, the input is a vector referred to as a "pattern" of n components referred to as "features". F is defined as the n-dimensional feature space. In the examples given, the features are gene expression coefficients and the patterns correspond to patients. While the present discussion is directed to two-class classification problems, this is not to limit the scope of the invention. The two classes are identified with the symbols (+) and (−). A training set of a number of patterns $\{x_1, x_2, \ldots x_k, \ldots x_l\}$ with known class labels $\{y_1, y_2, \ldots y_k, \ldots y_l\}$, $y_k \in \{-1,+1\}$, is given. The training patterns are used to build a decision function (or discriminant function) D(x), that is a scalar function of an input pattern x. New patterns are classified according to the sign of the decision function:

$D(x)>0 \Rightarrow \epsilon\text{class}(+)$;

$D(x)<0 \Rightarrow \epsilon\text{class}(-)$;

$D(x)=0$, decision boundary;

where $\epsilon$ means "is a member of".

Decision boundaries that are simple weighted sums of the training patterns plus a bias are referred to as "linear discriminant functions", e.g., $$D(x)=w \cdot x+b, \quad (1)$$

where w is the weight vector and b is a bias value. A data set is said to be linearly separable if a linear discriminant function can separate it without error.

Feature selection in large dimensional input spaces is performed using greedy algorithms and feature ranking. A fixed number of top ranked features may be selected for further analysis or to design a classifier. Alternatively, a threshold can be set on the ranking criterion. Only the features whose criteria exceed the threshold are retained. A preferred method uses the ranking to define nested subsets of features, $F_1 \subset F_2 \subset \ldots \subset F$, and select an optimum subset of features with a model selection criterion by varying a single parameter: the number of features.

Errorless separation can be achieved with any number of genes greater than one. Preferred methods comprise use of a smaller number of genes. Classical gene selection methods select the genes that individually best classify the training data. These methods include correlation methods and expression ratio methods. While the classical methods eliminate genes that are useless for discrimination (noise), they do not yield compact gene sets because genes are redundant. Moreover, complementary genes that individually do not separate well are missed.

A simple feature ranking can be produced by evaluating how well an individual feature contributes to the separation (e.g. cancer vs. normal). Various correlation coefficients have been proposed as ranking criteria. For example, see, T. K. Golub, et al, "Molecular classification of cancer: Class discovery and class prediction by gene expression monitoring", Science 286, 531-37 (1999). The coefficient used by Golub et al. is defined as:

$$w_i=(\mu_i(+)-\mu_i(-))/(\sigma_i(+)+\sigma_i(-)) \quad (2)$$

where $\mu_i$ and $\sigma_i$ are the mean and standard deviation, respectively, of the gene expression values of a particular gene i for all the patients of class (+) or class (−), i=1, ... n .... Large positive $w_i$ values indicate strong correlation with class (+) whereas large negative $w_i$ values indicate strong correlation with class (−). The method described by Golub, et al. for feature ranking is to select an equal number of genes with positive and with negative correlation coefficient. Other methods use the absolute value of $w_i$ as ranking criterion, or a related coefficient, $$(\mu_i(+)-\mu_i(-))^2/(\sigma_i(+)^2+\sigma_i(-)^2). \quad (3)$$

What characterizes feature ranking with correlation methods is the implicit orthogonality assumptions that are made. Each coefficient $w_i$ is computed with information about a single feature (gene) and does not take into account mutual information between features.

One use of feature ranking is in the design of a class predictor (or classifier) based on a pre-selected subset of genes. Each feature which is correlated (or anti-correlated) with the separation of interest is by itself such a class predictor, albeit an imperfect one. A simple method of classification comprises a method based on weighted voting: the features vote in proportion to their correlation coefficient. Such is the method used by Golub, et al. The weighted voting scheme yields a particular linear discriminant classifier:

$$D(x)=w \cdot (x-\mu), \quad (4)$$

where w is $w_i=(\mu_i(+)-\mu_i(-))/(\sigma_i(+)+\sigma_i(-))$ and $\mu=(\mu(+)+\mu(-))/2$ Another classifier or class predictor is Fisher's linear discriminant. Such a classifier is similar to that of Golub et al. where $$w=S^{-1}(\mu(+)+\mu(-)), \quad (5)$$

where S is the (n,n) within class scatter matrix defined as $$S = \sum_{x \in X(+)} (x-\mu(+))(x-\mu(+))^T + \sum_{x \in X(-)} (x-\mu(-))(x-\mu(-))^T, \quad (6)$$

where $\mu$ is the mean vector over all training patters and X(+) and X(−) are the training sets of class (+) and (−), respectively. This form of Fisher's discriminant implies that S is invertible, however, this is not the case if the number of features n is larger than the number of examples l since the rank of S is at most l. The classifiers of Equations 4 and 6 are similar if the scatter matrix is approximated by its diagonal elements. This approximation is exact when the vectors formed by the values of one feature across all training patterns are orthogonal, after subtracting the class mean. The approximation retains some validity if the features are uncorrelated, that is, if the expected value of the product of two different features is zero, after removing the class mean. Approximating S by its diagonal elements is one way of regularizing it (making it invertible). However, features usually are correlated and, therefore, the diagonal approximation is not valid.

One aspect of the present invention comprises using the feature ranking coefficients as classifier weights. Reciprocally, the weights multiplying the inputs of a given classifier can be used as feature ranking coefficients. The inputs that are weighted by the largest values have the most influence in the classification decision. Therefore, if the classifier performs well, those inputs with largest weights correspond to the most informative features, or in this instance, genes. Other methods, known as multivariate classifiers, comprise algorithms to train linear discriminant functions that provide superior feature ranking compared to correlation coefficients. Multivariate classifiers, such as the Fisher's linear discriminant (a combination of multiple univariate classifiers) and methods disclosed herein, are optimized during training to handle multiple variables or features simultaneously.

For classification problems, the ideal objective function is the expected value of the error, i.e., the error rate computed on an infinite number of examples. For training purposes, this ideal objective is replaced by a cost function J computed on training examples only. Such a cost function is usually a bound or an approximation of the ideal objective, selected for convenience and efficiency. For linear SVMs, the cost function is:

$$J=(\frac{1}{2})\|w\|^2, \quad (7)$$

which is minimized, under constraints, during training. The criteria $(w_i)^2$ estimates the effect on the objective (cost) function of removing feature i.

A good feature ranking criterion is not necessarily a good criterion for ranking feature subsets. Some criteria estimate the effect on the objective function of removing one feature at a time. These criteria become suboptimal when several features are removed at one time, which is necessary to obtain a small feature subset.

Recursive Feature Elimination (RFE) methods can be used to overcome this problem. RFE methods comprise iteratively 1) training the classifier, 2) computing the ranking criterion for all features, and 3) removing the feature having the smallest ranking criterion. This iterative procedure is an example of backward feature elimination. For computational reasons, it may be more efficient to remove several features at a time at the expense of possible classification performance degradation. In such a case, the method produces a "feature subset ranking", as opposed to a "feature ranking". Feature subsets are nested, e.g., $F_1 \subset F_2 \subset \ldots \subset F$.

If features are removed one at a time, this results in a corresponding feature ranking. However, the features that are top ranked, i.e., eliminated last, are not necessarily the ones that are individually most relevant. It may be the case that the features of a subset $F_m$ are optimal in some sense only when taken in some combination. RFE has no effect on correlation methods since the ranking criterion is computed using information about a single feature.

In the present embodiment, the weights of a classifier are used to produce a feature ranking with a SVM (Support Vector Machine). The present invention contemplates methods of SVMs used for both linear and non-linear decision boundaries of arbitrary complexity, however, the example provided herein is directed to linear SVMs because of the nature of the data set under investigation. Linear SVMs are particular linear discriminant classifiers. (See Equation 1). If the training set is linearly separable, a linear SVM is a maximum margin classifier. The decision boundary (a straight line in the case of a two-dimension separation) is positioned to leave the largest possible margin on either side. One quality of SVMs is that the weights $w_i$ of the decision function $D(x)$ are a function only of a small subset of the training examples, i.e., "support vectors". Support vectors are the examples that are closest to the decision boundary and lie on the margin. The existence of such support vectors is at the origin of the computational properties of SVM and its competitive classification performance. While SVMs base their decision function on the support vectors that are the borderline cases, other methods such as the previously-described method of Golub, et al., base the decision function on the average case.

A preferred method of the present invention comprises using a variant of the soft-margin algorithm where training comprises executing a quadratic program as described by Cortes and Vapnik in "Support vector networks", 1995, *Machine Learning*, 20:3, 273-297, which is incorporated herein by reference in its entirety. The following is provided as an example, however, different programs are contemplated by the present invention and can be determined by those skilled in the art for the particular data sets involved.

Inputs comprise training examples (vectors) $\{x_1, x_1, \ldots x_k \ldots x_l\}$ and class labels $\{y_1, y_2 \ldots y_k \ldots y_l\}$. To identify the optimal hyperplane, the following quadratic program is executed:

$$\begin{cases} \text{Minimize over } \alpha_k: \\ J = (1/2) \sum_{hk} y_h y_k \alpha_h \alpha_k (x_h \cdot x_k + \lambda \delta_{hk}) - \sum_k \alpha_k \\ \text{subject to:} \\ 0 \le \alpha_k \le C \text{ and } \sum_k \alpha_k y_k = 0 \end{cases} \quad (8)$$

with the resulting outputs being the parameters $\alpha_k$, where the summations run over all training patterns $x_k$ that are n dimensional feature vectors, $x_h \cdot x_k$ denotes the scalar product, $y_k$ encodes the class label as a binary value=1 or −1, $\delta_{hk}$ is the Kronecker symbol ($\delta_{hk}=1$ if h=k and 0 otherwise), and $\lambda$ and C are positive constants (soft margin parameters). The soft margin parameters ensure convergence even when the problem is non-linearly separable or poorly conditioned. In such cases, some support vectors may not lie on the margin. Methods include relying on $\lambda$ or C, but preferred methods, and those used in the Examples below, use a small value of $\lambda$ (on the order of $10^{-14}$) to ensure numerical stability. For the Examples provided herein, the solution is rather insensitive to the value of C because the training data sets are linearly separable down to only a few features. A value of C=100 is adequate, however, other methods may use other values of C.

The resulting decision function of an input vector x is:

$$D(x) = w \cdot x + b \text{ with } w = \sum_k \alpha_k y_k x_k \text{ and } b = \langle y_k - w \cdot x_k \rangle \quad (9)$$

The weight vector w is a linear combination of training patterns. Most weights $\alpha_k$ are zero. The training patterns with non-zero weights are support vectors. Those having a weight that satisfies the strict inequality $0<\alpha_k<C$ are marginal support vectors. The bias value b is an average over marginal support vectors.

The following sequence illustrates application of recursive feature elimination (RFE) to a SVM using the weight magnitude as the ranking criterion. The inputs are training examples (vectors): $X_0=[x_1, x_2, \ldots x_k \ldots x_l]^T$ and class labels $Y=[y_1, y_2 \ldots y_k \ldots y_l]^T$.

Initialize:

Subset of surviving features s=[1, 2, ... n]

Features ranked list r=[ ]

Repeat until s=[ ]

Restrict training examples to good feature indices $X=X_0(:,s)$

Train the classifier

α=SVM train(X,y)

Compute the weight vector of dimension length(s):

$$w = \sum_k \alpha_k y_k x_k$$

Compute the ranking criteria $c_i=(w_i)^2$, for all $i$

Find the feature with smallest ranking criterion $f$=argmin(c)

Update feature ranked list r=[s(f),r]

Eliminate the feature with smallest ranking criterion s=s(1:f−1,f=1:length(s))

The output comprises feature ranked list r.

The above steps can be modified to increase computing speed by generalizing the algorithm to remove more than one feature per step.

In general, SVM-RFE is computationally expensive when compared against correlation methods, where several thousands of input data points can be ranked in about one second using a PENTIUM® processor, and weights of the classifier trained only once with all features, such as SVMs or pseudo-inverse/mean squared error (MSE). A SVM implemented using non-optimized MATLAB® code on a PENTIUM® processor can provide a solution in a few seconds. To increase computational speed, RFE is preferably implemented by training multiple classifiers on subsets of features of decreasing size. Training time scales linearly with the number of classifiers to be trained. The trade-off is computational time versus accuracy. Use of RFE provides better feature selection than can be obtained by using the weights of a single classifier. Better results are also obtained by eliminating one feature at a time as opposed to eliminating chunks of features. However, significant differences are seen only for a smaller subset of features such as fewer than 100. Without trading accuracy for speed, RFE can be used by removing chunks of features in the first few iterations and then, in later iterations, removing one feature at a time once the feature set reaches a few hundreds. RFE can be used when the number of features, e.g., genes, is increased to millions. In one example, at the first iteration, the number of genes was reached that was the closest power of two. At subsequent iterations, half of the remaining genes were eliminated, such that each iteration was reduced by a power of two. Nested subsets of genes were obtained that had increasing information density.

RFE consistently outperforms the naïve ranking, particularly for small feature subsets. (The naïve ranking comprises ranking the features with $(w_i)^2$, which is computationally equivalent to the first iteration of RFE.) The naïve ranking organizes features according to their individual relevance, while RFE ranking is a feature subset ranking. The nested feature subsets contain complementary features that individually are not necessarily the most relevant. An important aspect of SVM feature selection is that clean data is most preferred because outliers play an essential role. The selection of useful patterns, support vectors, and selection of useful features are connected.

Pre-processing can have a strong impact on SVM-RFE. In particular, feature scales must be comparable. One pre-processing method is to subtract the mean of a feature from each feature, then divide the result by its standard deviation. Such pre-processing is not necessary if scaling is taken into account in the computational cost function. Another pre-processing operation can be performed to reduce skew in the data distribution and provide more uniform distribution. This pre-processing step involves taking the log of the value, which is particularly advantageous when the data consists of gene expression coefficients, which are often obtained by computing the ratio of two values. For example, in a competitive hybridization scheme, DNA from two samples that are labeled differently are hybridized onto the array. One obtains at every point of the array two coefficients corresponding to the fluorescence of the two labels and reflecting the fraction of DNA of either sample that hybridized to the particular gene. Typically, the first initial preprocessing step that is taken is to take the ratio a/b of these two values. Though this initial preprocessing step is adequate, it may not be optimal when the two values are small. Other initial preprocessing steps include (a−b)/(a+b) and (log a−log b)/(log a+log b).

Another pre-processing step involved normalizing the data across all samples by subtracting the mean. This preprocessing step is supported by the fact that, using tissue samples, there are variations in experimental conditions from microarray to microarray. Although standard deviation seems to remain fairly constant, the other preprocessing step selected was to divide the gene expression values by the standard deviation to obtain centered data of standardized variance.

To normalize each gene expression across multiple tissue samples, the mean expression value and standard deviation for each gene was computed. For all of the tissue sample values of that gene (training and test), that mean was then subtracted and the resultant value was divided by the standard deviation. In some experiments, an additional preprocessing step was added by passing the data through a squashing function [$f(x)=c \arctan (x/c)$] to diminish the importance of the outliers.

In a variation on several of the preceding pre-processing methods, the data can be pre-processed by a simple "whitening" to make data matrix resemble "white noise." The samples can be pre-processed to: normalize matrix columns; normalize matrix lines; and normalize columns again. Normalization consists of subtracting the mean and dividing by the standard deviation. A further normalization step can be taken when the samples are split into a training set and a test set.

The mean and variance column-wise was computed for the training samples only. All samples (training and test samples) were then normalized by subtracting that mean and dividing by the standard deviation.

In addition to the above-described linear example, SVM-RFE can be used in nonlinear cases and other kernel methods. The method of eliminating features on the basis of the smallest change in cost function can be extended to nonlinear uses and to all kernel methods in general. Computations can be made tractable by assuming no change in the value of the $\alpha$'s. Thus, the classifier need not be retrained for every candidate feature to be eliminated.

Specifically, in the case of SVMs, the cost function to be minimized (under the constraints $0 \leq \alpha_k \leq C$ and $\Sigma_k \alpha_k \gamma_k = 0$) is:

$$J=(\tfrac{1}{2})\alpha^T H\alpha - \alpha^T 1, \qquad (10)$$

where H is the matrix with elements $\gamma_h \gamma_k K(x_h x_k)$, K is a kernel function that measures the similarity between $x_h$ and $x_k$, and 1 is an l dimensional vector of ones.

An example of such a kernel function is $$K(x_h x_k)=\exp(-\gamma\|x_h - x_k\|^2). \qquad (11)$$

To compute the change in cost function caused by removing input component i, one leaves the $\alpha$'s unchanged and recomputes matrix H. This corresponds to computing $K(x_h(-i), x_k(-i))$, yielding matrix H(−i), where the notation (−i) means that component i has been removed. The resulting ranking coefficient is:

$$DJ(i)=(\tfrac{1}{2})\alpha^T H\alpha - (\tfrac{1}{2})\alpha^T H(-i)\alpha \qquad (12)$$

The input corresponding to the smallest difference DJ(i) is then removed. The procedure is repeated to carry out Recursive Feature Elimination (RFE).

The advantages of RFE are further illustrated by the following example, which is not to be construed in any way as imposing limitations upon the scope thereof. On the contrary, it is to be clearly understood that resort may be had to various other embodiments, modifications, and equivalents thereof which, after reading the description herein, may suggest themselves to those skilled in the art without departing from the spirit of the present invention and/or the scope of the appended claims.

Example 1

Analysis of Gene Patterns Related to Colon Cancer

Analysis of data from diagnostic genetic testing, microarray data of gene expression vectors, was performed with a SVM-RFE. The original data for this example was derived from the data presented in Alon et al., 1999. Gene expression information was extracted from microarray data resulting, after pre-processing, in a table of 62 tissues×2000 genes. The 62 tissues include 22 normal tissues and 40 colon cancer tissues. The matrix contains the expression of the 2000 genes with highest minimal intensity across the 62 tissues. Some of the genes are non-human genes.

The data proved to be relatively easy to separate. After preprocessing, it was possible to a find a weighted sum of a set of only a few genes that separated without error the entire data set, thus the data set was linearly separable. One problem in the colon cancer data set was that tumor samples and normal samples differed in cell composition. Tumor samples were normally rich in epithelial cells wherein normal samples were a mixture of cell types, including a large fraction of smooth muscle cells. While the samples could be easily separated on the basis of cell composition, this separation was not very informative for tracking cancer-related genes.

The gene selection method using RFE-SVM is compared against a reference gene selection method described in Golub et al, *Science*, 1999, which is referred to as the "baseline method" Since there was no defined training and test set, the data was randomly split into 31 samples for training and 31 samples for testing.

In Golub et al., the authors use several metrics of classifier quality, including error rate, rejection rate at fixed threshold, and classification confidence. Each value is computed both on the independent test set and using the leave-one-out method on the training set. The leave-one-out method consists of removing one example from the training set, constructing the decision function on the basis only of the remaining training data and then testing on the removed example. In this method, one tests all examples of the training data and measures the fraction of errors over the total number of training examples.

The methods of this Example use a modification of the above metrics. The present classification methods use various decision functions (D(x)) whose inputs are gene expression coefficients and whose outputs are a signed number indicative of whether or not cancer was present. The classification decision is carried out according to the sign of D(x). The magnitude of D(x) is indicative of classification confidence.

Four metrics of classifier quality were used: (1) Error (B1+B2)=number of errors ("bad") at zero rejection; (2) Reject (R1+R2)=minimum number of rejected samples to obtain zero error; Extremal margin (E/D)=difference between the smallest output of the positive class samples and the largest output of the negative class samples (rescaled by the largest difference between outputs); and Median margin (M/D)=difference between the median output of the positive class samples and the median output of the negative class samples (resealed by the largest difference between outputs). Each value is computed both on the training set with the leave-one-out method and on the test set.

The error rate is the fraction of examples that are misclassified (corresponding to a diagnostic error). The error rate is complemented by the success rate. The rejection rate is the fraction of examples that are rejected (on which no decision is made because of low confidence). The rejection rate is complemented by the acceptance rate. Extremal and median margins are measurements of classification confidence. Note that the margin computed with the leave-one-out method or on the test set differs from the margin computed on training examples sometimes used in model selection criteria.

A method for predicting the optimum subset of genes comprised defining a criterion of optimality that uses information derived from training examples only. This criterion was checked by determining whether the predicted gene subset performed best on the test set.

A criterion that is often used in similar "model selection" problems is the leave-one-out success rate $V_{suc}$. In the present example, it was of little use since differentiation between many classifiers that have zero leave-one-out error is not allowed. Such differentiation is obtained by using a criterion that combines all of the quality metrics computed by cross-validation with the leave-one-out method:

$$Q = V_{suc} + V_{acc} + V_{ext} + V_{med} \tag{13}$$

where $V_{suc}$ is the success rate, $V_{acc}$ the acceptance rate, $V_{ext}$ the extremal margin, and $V_{med}$ is the median margin.

Theoretical considerations suggested modification of this criterion to penalize large gene sets. The probability of observing large differences between the leave-one-out error and the test error increases with the size d of the gene set, according to $$\epsilon(d) = sqrt(-\log(\alpha) + \log(G(d))) \cdot sqrt(p(1-p)/n) \tag{14}$$

where $(1-\alpha)$ is the confidence (typically 95%, i.e., $\alpha=0.05$), p is the "true" error rate ($p<=0.01$), and n is the size of the training set.

Following the guaranteed risk principle, a quantity proportional to $\epsilon(d)$ was subtracted from criterion Q to obtain a new criterion:

$$C = Q - 2\epsilon(d) \tag{15}$$

The coefficient of proportionality was computed heuristically, assuming that $V_{suc}$, $V_{acc}$, $V_{ext}$ and $V_{med}$ are independent random variables with the same error bar $\epsilon(d)$ and that this error bar is commensurate to a standard deviation. In this case, variances would be additive, therefore, the error bar should be multiplied by sqrt(4).

A SVM-RFE was run on the raw data to assess the validity of the method. The colon cancer data samples were split randomly into 31 examples for training and 31 examples for testing. The RFE method was run to progressively downsize the number of genes, each time dividing the number by 2. The pre-processing of the data for each gene expression value consisted of subtracting the mean from the value, then dividing the result by the standard deviation.

The leave-one-out method with the classifier quality criterion was used to estimate the optimum number of genes. The leave-one-out method comprises taking out one example of the training set. Training is then performed on the remaining examples, with the left out example being used to test the trained classifier. This procedure is iterated over all the examples. Each criterion is computed as an average over all examples. The overall classifier quality criterion is calculated according to Equation 13. The classifier is a linear classifier with hard margin.

Results of the SVM-RFE as taught herein show that at the optimum predicted by the method using training data only, the leave-one-out error is zero and the test performance is actually optimum.

Figure 6:
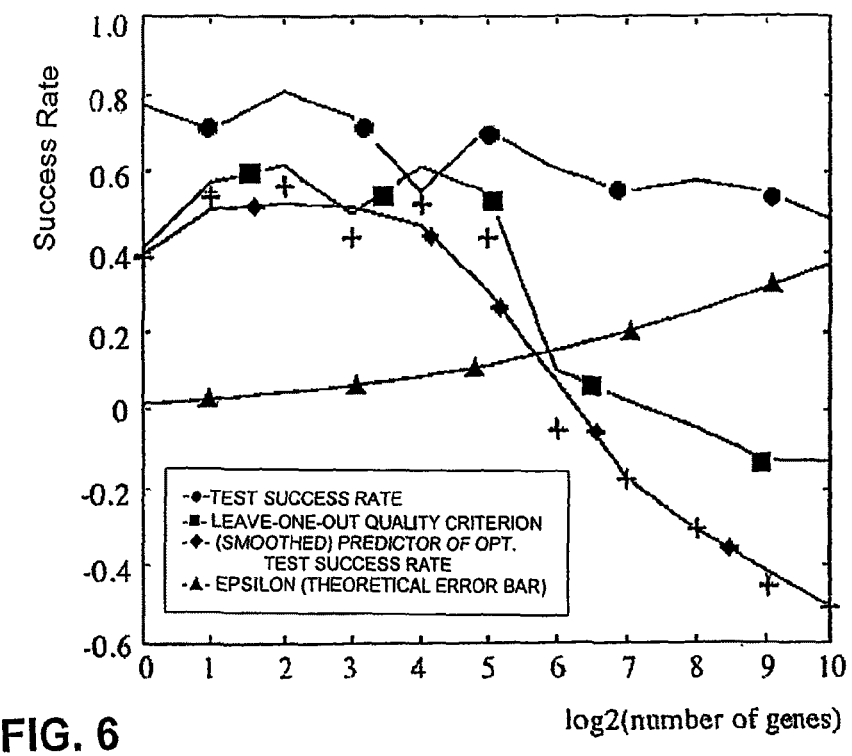
FIG. 6 shows graphs of the results of using RFE.

The optimum test performance had an 81% success rate without pre-processing to remove skew and to normalize the data. This result was consistent with the results reported in the original paper by Alon et al. Moreover, the errors, except for one, were identified by Alon et al. as outliers. The plot of the performance curves as a function of gene number is shown in FIG. 6. The predictor of optimum test success rate (diamond curve), which is obtained by smoothing after substracting $\epsilon$ from the leave-one-out quality criterion, coincides with the actual test success rate (circle curve) in finding the optimum number of genes to be 4.

Figure 7:
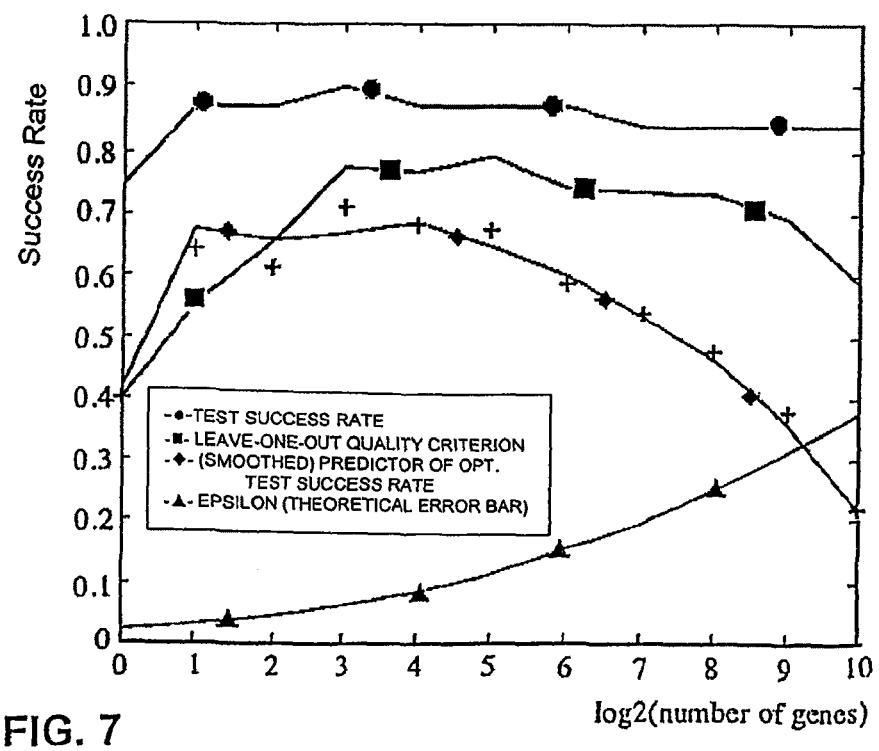
FIG. 7 shows the results of RFE after preprocessing.

When used in conjunction with pre-processing according to the description above to remove skew and normalize across samples, a SVM-RFE provided further improvement. FIG. 7 shows the results of RFE after preprocessing, where the predicted optimum test success rate is achieved with 16 genes. The reduced capacity SVM used in FIG. 6 is replaced by plain SVM. Although a $\log_2$ scale is still used for gene number, RFE was run by eliminating one gene at a time. The best test performance is 90% classification accuracy (8 genes). The optimum number of genes predicted from the classifier quality based on training data information only is 16. This corresponds to 87% classification accuracy on the test set.

Because of data redundancy, it was possible to find many subsets of genes that provide a reasonable separation. To analyze the results, the relatedness of the genes should be understand. While not wishing to be bound by any particular theory, it was the initial theory that the problem of gene selection was to find an optimum number of genes, preferably small, that separates normal tissues from cancer tissues with maximum accuracy.

SVM-RFE used a subset of genes that were complementary and thus carried little redundant information. No other information on the structure and nature of the data was provided. Because data were very redundant, a gene that had not been selected may nevertheless be informative for the separation.

Correlation methods such as Golub's method provide a ranked list of genes. The rank order characterizes how correlated the gene is with the separation. Generally, a gene highly ranked taken alone provides a better separation than a lower ranked gene. It is therefore possible to set a threshold (e.g. keep only the top ranked genes) that separates "highly informative genes" from "less informative genes".

The methods of the present invention such as SVM-RFE provide subsets of genes that are both smaller and more discriminant. The gene selection method using SVM-RFE also provides a ranked list of genes. With this list, nested subsets of genes of increasing sizes can be defined. However, the fact that one gene has a higher rank than another gene does not mean that this one factor alone characterizes the better separation. In fact, genes that are eliminated in an early iteration could well be very informative but redundant with others that were kept. The 32 best genes as a whole provide a good separation but individually may not be very correlated with the target separation. Gene ranking allows for a building nested subsets of genes that provide good separations, however it provides no information as to how good an individual gene may be. Genes of any rank may be correlated with the 32 best genes. The correlated genes may be ruled out at some point because of their redundancy with some of the remaining genes, not because they did not carry information relative to the target separation.

The gene ranking alone is insufficient to characterize which genes are informative and which ones are not, and also to determine which genes are complementary and which ones are redundant. Therefore, additional pre-processing in the form of clustering was performed.

To overcome the problems of gene ranking alone, the data was preprocessed with an unsupervised clustering method. Genes were grouped according to resemblance (according to a given metric). Cluster centers were then used instead of genes themselves and processed by SVM-RFE to produce nested subsets of cluster centers. An optimum subset size can be chosen with the same cross-validation method used before.

Figure 8:
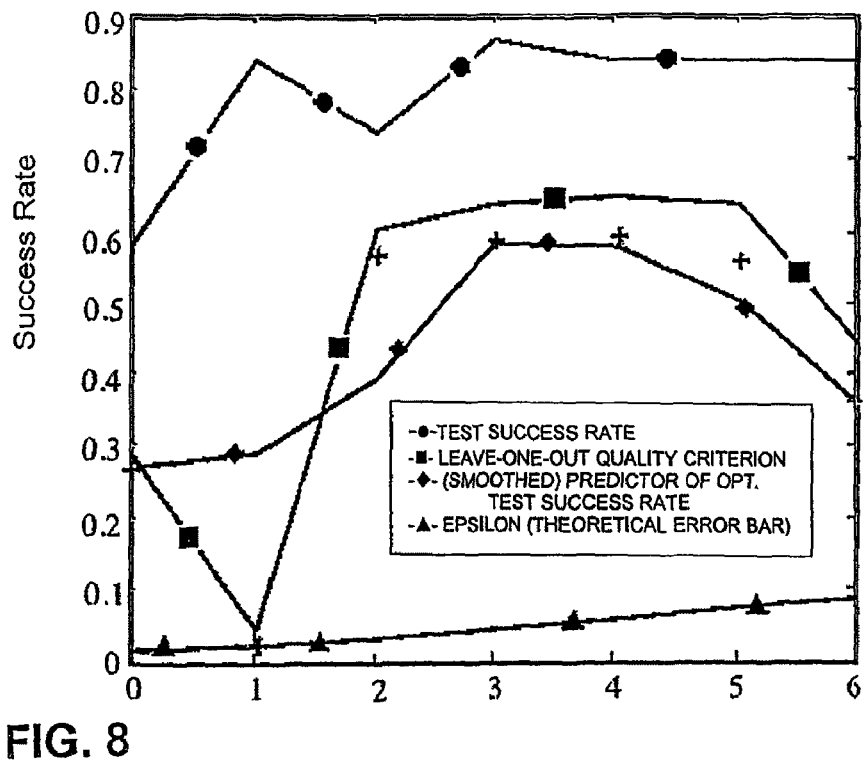
FIG. 8 shows the results of RFE when training on 100 dense QT_clust clusters.

Using the data, the $QT_{clust}$ clustering algorithm was used to produce 100 dense clusters. (The "quality clustering algorithm" ($QT_{clust}$) is well known to those of skill in the field of analysis of gene expression profiles.) The similarity measure used was Pearson's correlation coefficient (as commonly used for gene clustering). FIG. 8 provides the performance curves of the results of RFE when trained on 100 dense $QT_{clust}$ clusters. As indicated, the predicted optimum number of gene cluster centers is 8. The results of this analysis are comparable to those of FIG. 7.

With unsupervised clustering, a set of informative genes is defined, but there is no guarantee that the genes not retained do not carry information. When RFE was used on all $QT_{clust}$ clusters plus the remaining non-clustered genes (singleton clusters), the performance curves were quite similar, though the top set of gene clusters selected was completely different and included mostly singletons.

The cluster centers can be substituted by any of their members. This factor may be important in the design of some medical diagnosis tests. For example, the administration of some proteins may be easier than that of others. Having a choice of alternative genes introduces flexibility in the treatment and administration choices.

Hierarchical clustering instead of $QT_{clust}$ clustering was used to produce lots of small clusters containing 2 elements on average. Because of the smaller cluster cardinality, there were fewer gene alternatives from which to choose. In this instance, hierarchical clustering did not yield as good a result as using $QT_{clust}$ clustering. The present invention contemplates use of any of the known methods for clustering, including but not limited to hierarchical clustering, $QT_{clust}$ clustering and SVM clustering. The choice of which clustering method to employ in the invention is affected by the initial data and the outcome desired, and can be determined by those skilled in the art.

Another method used with the present invention was to use clustering as a post-processing step of SVM-RFE. Each gene selected by running regular SVM-RFE on the original set of gene expression coefficients was used as a cluster center. For example, the results described with reference to FIG. 7 were used. For each of the top eight genes, the correlation coefficient was computed with all remaining genes. The parameters were that the genes clustered to gene i were those that met the following two conditions: higher correlation coefficient with gene i than with other genes in the selected subset of eight genes, and correlation coefficient exceeding a threshold θ.

Compared to the unsupervised clustering method and results, the supervised clustering method, in this instance, does not provide better control over the number of examples per cluster. Therefore, this method is not as good as unsupervised clustering if the goal is the ability to select from a variety of genes in each cluster. However, supervised clustering may show specific clusters that have relevance for the specific knowledge being determined. In this particular embodiment, in particular, a very large cluster of genes was found that contained several muscle genes that may be related to tissue composition and may not be relevant to the cancer vs. normal separation. Thus, those genes are good candidates for elimination from consideration as having little bearing on the diagnosis or prognosis for colon cancer.

An additional pre-processing operation involved the use of expert knowledge to eliminating data that are known to complicate analysis due to the difficulty in differentiating the data from other data that is known to be useful. In the present Example, tissue composition-related genes were automatically eliminated in the pre-processing step by searching for the phrase "smooth muscle". Other means for searching the data for indicators of the smooth muscle genes may be used.

Figure 9:
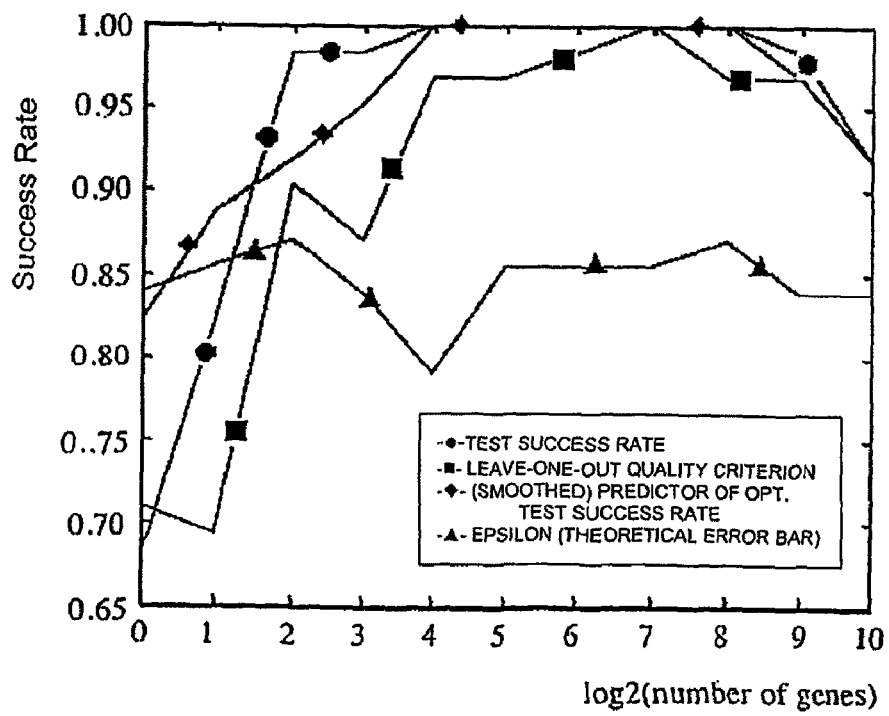
FIG. 9 shows a comparison of feature (gene) selection methods for colon cancer data.

The number of genes selected by Recursive Feature Elimination (RFE) was varied and was tested with different methods. Training was done on the entire data set of 62 samples. The curves represent the leave-one-out success rate. For comparison, the results obtained using several different methods for gene selection from colon cancer data are provided in FIG. 9. SVM-RFE is compared to Linear Discriminant Analysis (LDA)-RFE; Mean Squared Error (Pseudo-inverse)-(MSE)-RFE and the baseline method (Golub, 1999). As indicated, SVM-RFE provides the best results down to 4 genes. An examination of the genes selected reveals that SVM eliminates genes that are tissue composition-related and keeps only genes that are relevant to the cancer vs. normal separation. Conversely, other methods retain smooth muscle genes in their top ranked genes which aids in separating most samples, but is not relevant to the cancer vs. normal discrimination.

All methods that do not make independent assumptions outperform Golub's method and reach 100% leave-one-out accuracy for at least one value of the number of genes. LDA may be at a slight disadvantage on these plots because, for computational reasons, RFE was used by eliminating chunks of genes that decrease in size by powers of two. Other methods use RFE by eliminating one gene at a time.

Down to four genes, SVM-RFE provided better performance than the other methods. All methods predicted an optimum number of genes smaller or equal to 64 using the criterion of the Equation 15. The genes ranking 1 through 64 for all the methods studied were compared. The first gene that was related to tissue composition and mentions "smooth muscle" in its description ranks 5 for Golub's method, 4 for LDA, 1 for MSE and only 41 for SVM. Therefore, this was a strong indication that SVMs make a better use of the data compared with other methods since they are the only methods that effectively factors out tissue composition-related genes while providing highly accurate separations with a small subset of genes.

Figure 10:
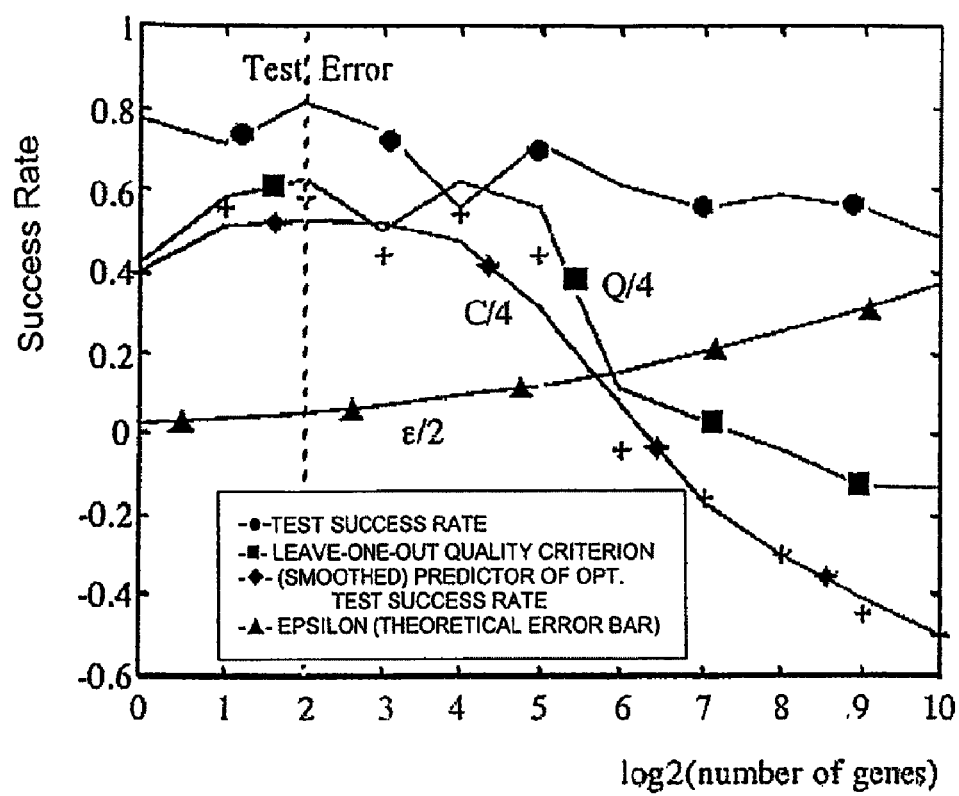
FIG. 10 shows the selection of an optimum number of genes for colon cancer data.
Figure 11A:
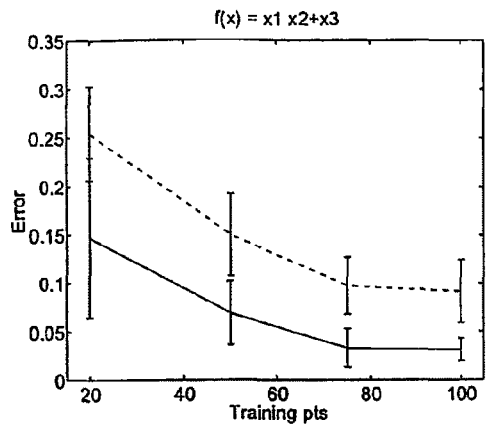
FIGS. 11a-f are plots comparing results with SVM and $l_0$-SVM approximation for learning sparse and non-sparse target functions with polynomials of degree 2 over 5 inputs, where
Figure 11B:
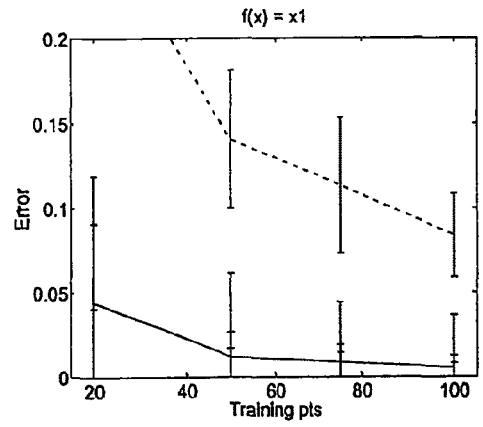
Figure 11C:
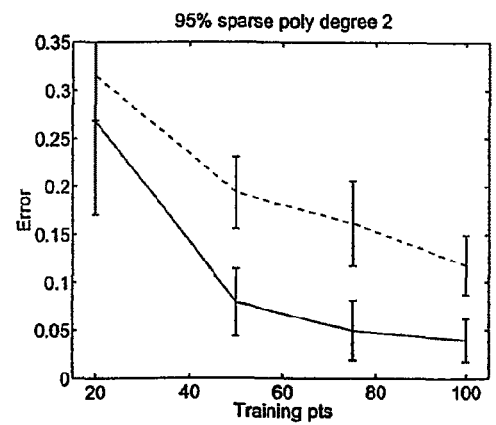
Figure 11D:
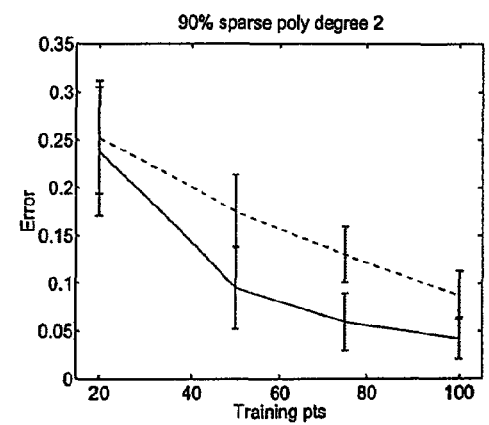
Figure 11E:
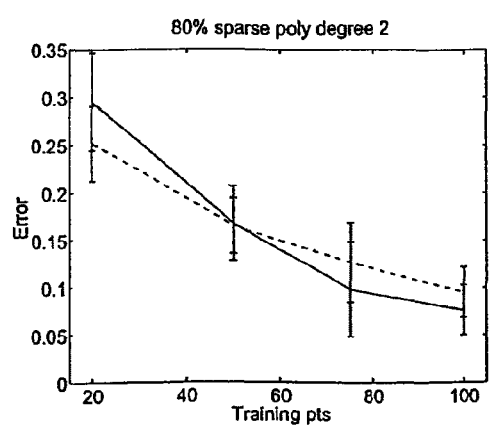
Figure 11F:
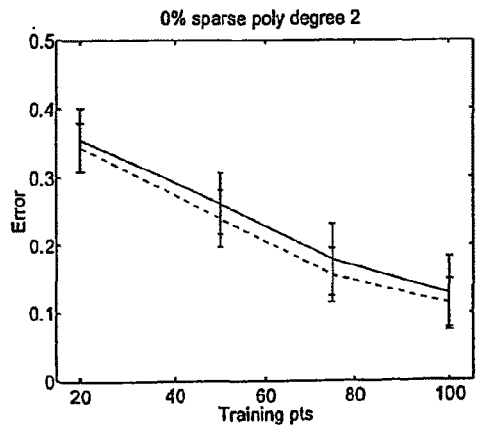
Figure 12A:
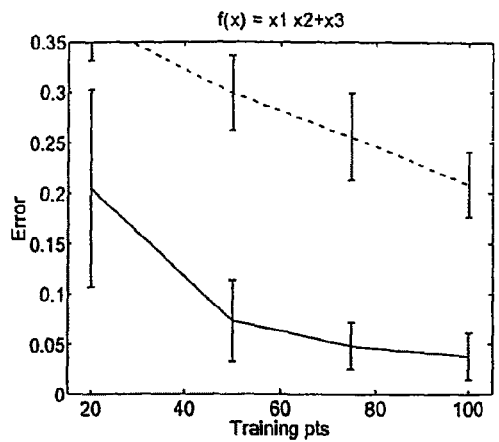
FIGS. 12a-f are plots comparing results with SVM and $l_2$-AL0M SVM approximation for learning sparse and non-sparse target functions with polynomials of degree 2 over 10 inputs, where
Figure 12B:
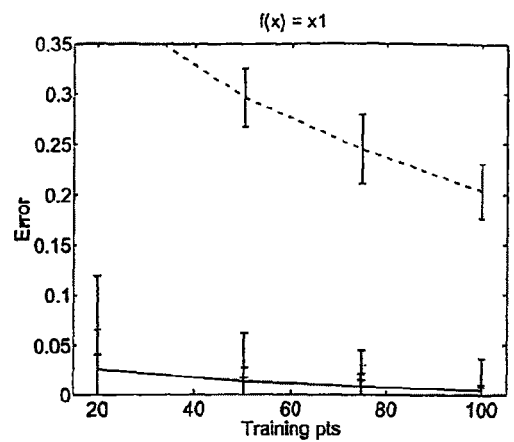
Figure 12C:
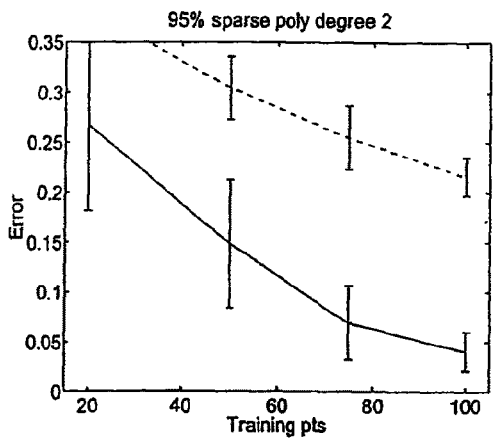
Figure 12D:
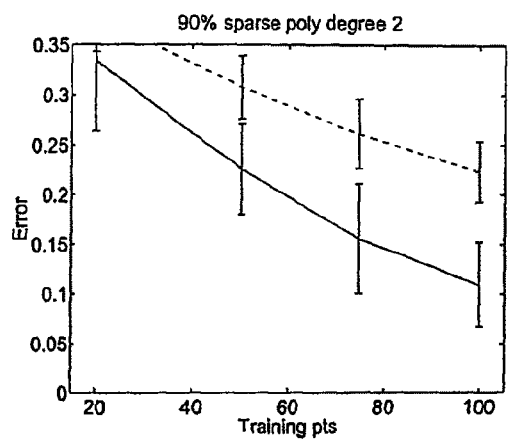
Figure 12E:
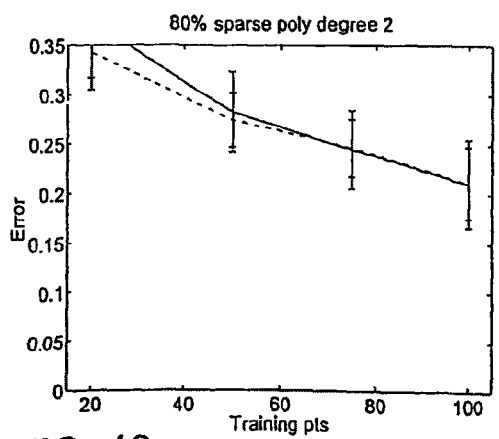
Figure 12F:
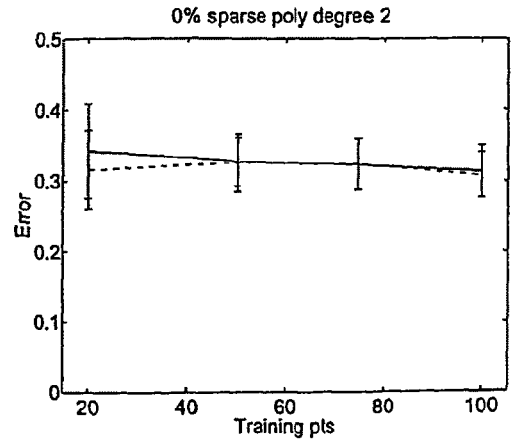

FIG. 10 is a plot of an optimum number of genes for evaluation of colon cancer data using RFE-SVM. The number of genes selected by recursive gene elimination with SVMs was varied and a number of quality metrics were evaluated include error rate on the test set, scaled quality criterion (Q/4), scaled criterion of optimality (C/4), locally smoothed C/4 and scaled theoretical error bar ($\epsilon/2$). The curves are related by C=Q-2$\epsilon$.

The model selection criterion was used in a variety of other experiments using SVMs and other algorithms. The optimum number of genes was always predicted accurately, within a factor of two of the number of genes.

Training algorithms such SVMs or Pseudo-inverse/MSE require first the computation of the (n,n) matrix K of all the scalar products between the n training patterns. The computation of K increases linearly with the number of features (genes) and quadratically with the number of training patterns. After that, the training time is on the order of the time to invert matrix K. For optimized SVM algorithms, training may be faster than inverting K, if the number of support vectors is small compared to n. For the data sets under study, the solution can be found in a couple of seconds on a PENTIUM® processor with non-optimized MATLAB® code.

Recursive Feature Elimination (RFE) requires training multiple classifiers on subsets of feature of decreasing size. The training time scales linearly with number of classifiers to be trained. Part of the calculations can be reused. Matrix K does not need to be re-computed entirely. The partial scalar products of the eliminated features can be subtracted. Also, the coefficients a can be initialized to their previous value. The MATLAB® software (from Math Works, Inc., Natick, Mass.) implementation of an SVM-RFE of the present invention on a PENTIUM® processor returns a gene ranking in about 15 minutes for the entire colon dataset (2000 genes, 62 patients) and 3 hours for the leukemia dataset (7129 genes, 72 patients). Given that the data collection and preparation may take several months or years, it is quite acceptable that the data analysis take a few hours.

Feature Selection by Minimizing $l_0$-norm. A second method of feature selection according to the present invention comprises minimizing the $l_0$-norm of parameter vectors. Such a procedure is central to many tasks in machine learning, including feature selection, vector quantization and compression methods. This method constructs a classifier which separates data using the smallest possible number of features. Specifically, the $l_0$-norm of w is minimized by solving the optimization problem $$\min_w \|w\|_0 \text{ subject to: } y_i(\langle w, x_i \rangle + b) \geq 1, \quad (16)$$

where $\|w\|_0 = \text{card}\{w_i | w_i \neq 0\}$. In other words, the goal is to find the fewest non-zero elements in the vector of coefficients w. However, because this problem is combinatorially hard, the following approximation is used:

$$\min_w \sum_{j=1}^{n} \ln(\varepsilon + |w_j|) \text{ subject to: } y_i(\langle w, x_i \rangle + b) \geq 1 \quad (17)$$

where $\epsilon \ll 1$ has been introduced in order to avoid ill-posed problems where one of the $w_j$ is zero. Because there are many local minima, Equation 17 can be solved by using constrained gradient.

Let $w_l(\epsilon)$, also written $w_l$ when the context is clear, be the minimizer of Equation 17, and $w_0$ the minimizer of Equation 16, which provides $$\sum_{j=1}^{n} \ln(\varepsilon + |(w_l)_j|) \leq \sum_{j=1}^{n} \ln(\varepsilon + |(w_0)_j|) \quad (18)$$

$$\leq \sum_{(w_0)_j=0} \ln(\varepsilon) + \sum_{(w_0)_j \neq 0} \ln(\varepsilon + |(w_0)_j|) \quad (19)$$

$$\leq (n - \|w_0\|_0)\ln(\varepsilon) + \sum \ln(\varepsilon + |(w_0)_j|). \quad (20)$$

The second term of the right hand side of Equation 20 is negligible compared to the $\ln(\epsilon)$ term when $\epsilon$ is very small. Thus, $$(n - \|w_l\|_0)\ln(\varepsilon) + \sum_{(w_l)_j \neq 0} \ln(\varepsilon + |(w_l)_j|) \leq (n - \|w_0\|_0)\ln(\varepsilon) \quad (21)$$

$$\|w_l\|_0 \leq \|w_0\|_0 - \sum_{(w_l)_j \neq 0} \frac{\ln(\varepsilon + |(w_l)_j|)}{\ln(1/\varepsilon)}. \quad (22)$$

Depending on the value of $(w_l(\epsilon))_j$, the sum on the right-hand side can be large or small when $\epsilon \to 0$. This will depend mainly on the problem at hand. Note, however, that if $\epsilon$ is very small, for example, if $\epsilon$ equals the machine precision, then as soon as $(w_l)_j$ is $\Omega(1)$, the zero norm of $w_l$ is the same as the zero norm of $w_0$.

The foregoing supports that fact that for the objective problem of Equation 17 it is better to set $w_j$ to zero whenever possible. This is due to the form of the logarithm function that decreases quickly to zero compared to its increase for large values of $w_j$. Thus, it is better to increase one $w_j$ while setting another to zero rather than making a compromise between both. From this point forward, it will be assumed that $\epsilon$ is equal to the machine precision. To solve the problem of Equation 17, an iterative method is used which performs a gradient step at each iteration. The method known as Franke and Wolfe's method
is proved to converge to a local minimum. For the problem of interest, it takes the following form, which can be defined as an "Approximation of the $l_0$-norm Minimization", or "AL0M":

1. Start with $w=(1, \ldots, 1)$
2. Assume $w_k$ is given. Solve $$\min \sum_{j=1}^{n} |w_j| \text{ subject to: } y_i(\langle w, (x_i * w_k) \rangle + b) \geq 1. \quad (23)$$

3. Let $\hat{w}$ be the solution of the previous problem. Set $w_{k+1} = w_k * \hat{w}$.
4. Repeat steps 2 and 3 until convergence.

AL0M solves a succession of linear optimization problems with non-sparse constraints. Sometimes, it may be more advantageous to have a quadratic programming formulation of these problems since the dual may have simple constraints and may then become easy to solve. As a generalization of the previous method, the present embodiment uses a procedure referred to as "$l_2$-AL0M" to minimize the $l_0$ norm as follows:

1. Start with $w=(1, \ldots, 1)$
2. Assume $w_k$ is given. Solve $$\min_w \|w\|_2^2 \text{ subject to: } y_i(\langle w, (x_i * w_k) \rangle + b) \geq 1. \quad (24)$$

3. Let $\hat{w}$ be the solution of the previous problem. Set $w_{k+1} = w_k * \hat{w}$.
4. Repeat steps 2 and 3 until convergence.

This method is developed for a linearly-separable learning set.

When many classes are involved, one could use a classical trick that consists of decomposing the multiclass problem into many two-class problems. Generally, a "one-against-all" approach is used. One vector $w_c$ and one bias $b_c$ are defined for each class c, and the output is computed as $$f(x) = \operatorname*{argmax}_c \langle w_c, x \rangle + b_c. \quad (25)$$

Then, the vector $w_c$ is learned by discriminating the class c from all other classes. This gives many two-class problems. In this framework, the minimization of the $l_0$-norm is done for each vector $w_c$ independently of the others. However, the true $l_0$-norm is the following:

$$\sum_{c=1}^{K} \|w_c\|_0 \quad (26)$$

where K is the number of classes. Thus, applying this kind of decomposition scheme adds a suboptimal process to the overall method. To perform a $l_0$-norm minimization for the multiclass problems, the above-described $l_2$ approximation method is used with different constraints and a different system:

1. Start with $w_c=(1, \ldots, 1)$, for $c=1, \ldots, K$
2. Assume $W_k=(w_1^k, \ldots, w_c^k, \ldots, w_K^k)$ is given. Solve $$\min_w \sum_{c=1}^{K} \|w_c\|_2^2 \quad (27)$$

subject to: $\langle w_{c(i)}, (x_i * w_{c(i)}^k) \rangle - \langle w_c, (x_i * w_c^k) \rangle + b_{c(i)} - b_c \geq 1$
for $c=1, \ldots, K$.

3. Let $\hat{W}$ be the solution to the previous problem. Set $W_{k+1} = W_k * \hat{W}$.
4. Repeat steps 2 and 3 until convergence.

As for the two-class case, this procedure is related to the following minimization problem:

$$\min_w \sum_{c=1}^{K} \sum_{j=1}^{n} \ln(\varepsilon + |(w_c)_j|) \quad (28)$$

subject to: $\langle w_{c(i)}, (x_i * w_{c(i)}^k) \rangle - \langle w_c, (x_i * w_c^k) \rangle + b_{c(i)} - b_c \geq 1$ for $k=1, \ldots, C$.

In order to generalize this algorithm to the non-linear case, the following dual optimization problem must be considered:

$$\max_{\alpha_i} -\frac{1}{2} \sum_{i,j=1}^{l} \alpha_i \alpha_j y_i y_j \langle x_i, x \rangle + \sum_{i=1}^{l} \alpha_i \text{ subject to } \sum_{i=1}^{l} \alpha_i y_i \quad (29)$$

where $C \geq \alpha_i \geq 0$ and where $\alpha_i$ are the dual variables related to the constraints $y_i(\langle w, x_i \rangle + b) \geq 1 - \xi_i$. The solution of this problem can then be used to compute the value of w and b.
In particular, $$\langle w, x \rangle = \sum_{i=1}^{\ell} \alpha_i y_i \langle x_i, x \rangle. \quad (30)$$

This means that the decision function of Equation 1, which may also be represented as $D(x)=\text{sign}(\langle w,x \rangle+b)$, can only be computed using dot products. As a result, any kind of function $k(.,.)$ can be used instead of $\langle .,. \rangle$ if k can be understood as a dot-product. Accordingly, the function $\Phi(x)=\phi_1(x), \ldots, \phi_i(x) \in l_2$ which maps points $x_i$ into a feature space such that $k(x_1, x_2)$ can be interpreted as a dot product in feature space.

To apply the procedure in feature space it is necessary to compute element-wise multiplication in feature space. In order to avoid directly computing vectors in feature space, this multiplication is performed with kernels. Multiplications in feature space are of the form $\phi(x)*\phi(y)$.

First, consider feature spaces which are sums of monomials of order d. That is, kernels that describe feature spaces of the form $$\phi_d(x) = \langle x_{i_1}, \ldots, x_{i_d} : i \leq i_1, i_2, \ldots, i_d \leq N \rangle.$$

Next, perform an element-wise multiplication in this space:

$$\phi_d(x)*\phi_d(y)=(x_{i_1}y_{i_1}\ldots x_{i_d}y_{i_d}:i\le i_1,i_2,\ldots,i_d\le N), \text{which is equal to}$$

$$\phi_d(x*y)=(x_{i_1}y_{i_1}\ldots x_{i_d}y_{i_d}:i\le i_1,i_2,\ldots,i_d\le N).$$

Therefore, instead of calculating $\phi(x)*\phi(y)$, the equivalent expression can be calculated, avoiding computation of vector in feature space. This can be extended to feature spaces with monomials of degree d or less (polynomials) by noticing that $$\phi_{1:d}(x)=(\phi_p(x):1\le p\le d) \text{ and}$$

$$\phi_{1:d}(x*y)=\phi_{1:d}(x)*\phi_{1:d}(y). \tag{31}$$

Applying this to the problem at hand, one needs to compute both $w*x_i$ and $\langle(w*x_i), x_j\rangle$. The following shows how to approximate such a calculation.

After training an SVM, minimizing the $l_2$-norm in dual form, one obtains the vector w expressed by coefficients $\alpha$ $$w=\sum_{i=1}^{\ell}\alpha_i y_i\phi(x_i). \tag{32}$$

The map $\phi(x_i)\to\phi(x_i)*w$ must be computed to calculate the dot products (the kernel) between training data. Thus, a kernel function between data points $x_i$ and $x_j$ is now $$k_{M_1}(x_i,x_j)=\langle(\phi(x_i)*w),(\phi(x_j)*w)\rangle=\langle\phi(x_i)*\phi(x_j),(w*w)\rangle. \tag{33}$$

Let the vector $s_i$ be the vector that scales the original dot product on iteration i+1 of the algorithm. Then, $s_0$ is the vector of ones, $s_1=(w*w)$ and, in general, $s_i=s_{i-1}*(w*w)$ when w is the vector of coefficients from training on step i. Thus, the kernel function on iteration i+1 is $$k_{s_i}(x_i,x_j)=\langle\phi(x_i)*\phi(x_j),s_i\rangle.$$

Considering the kernel for iteration 2, $s_1$, $$k_{s_i}(x_i,x_j)=\langle(\phi(x_i)*\phi(x_j)),s_i\rangle$$
$$=\langle(\phi(x_i)*s_i),\phi(x_j)\rangle$$

Now, $s_1=(w*w)$. For polynomial type kernels utilizing Equations 31 and 32, $$s_1=\sum_{n,m=1}^{\ell}\alpha_n\alpha_m y_n y_m\phi(x_n*x_m). \tag{34}$$

This produces the kernel $$k_{s_1}(x_i,x_j)=\Sigma\alpha_i\alpha_j y_i y_j k(x_n*x_m*x_i,x_j),$$

and in general on step n>0, $$s_n=\sum_{i_1,\ldots,i_n}^{\ell}\alpha_{i_1}y_{i_1}\ldots\alpha_{i_n}y_{i_n}\phi(x_{i_1}*\ldots*x_{i_n}), \tag{35}$$

$$k_{s_n}(x_i,x_j)=\sum_{i_1,\ldots,i_n}^{\ell}\alpha_{i_1}y_{i_1}\ldots\alpha_{i_n}y_{i_n}k(x_{i_1}*\ldots*x_{i_n}*x_i,x_j).$$

As this can become costly to compute after iteration 2, the vector $s_1$ can be computed at each step as a linear combination of training points, i.e., $$s_n=\Sigma\beta_i^n\phi(x_i)$$

$$k_{s_n}(x_i,x_j)=\Sigma\beta_k^n k(x_k*x_i,x_j)$$

This can be achieved by, at each step, approximating the expansion $$(w*w)=\sum_{n,m=1}^{l}\alpha_n\alpha_m y_n y_m\phi(x_n*x_m)$$

$$\text{with } w_{approx}^2=\sum_{i=1}^{l}\beta_i\phi(x_i).$$

The coefficients $\beta_i$ are found using a convex optimization problem by minimizing in the $l_2$-norm the different between the true vector and the approximation. That is, the following is minimized:

$$\|w_{approx}^2-(w*w)\|_2^2=\left\|\sum_{i=1}^{l}\beta_i\phi(x_i)-\sum_{n,m=1}^{l}\alpha_n\alpha_m y_n y_m\phi(x_n*x_m)\right\|_2^2 \tag{36}$$

$$=\sum_{i,j=1}^{l}\beta_i\beta_j k(x_i,x_j)-$$

$$2\sum_{i,n,m=1}^{l}\beta_i\alpha_n\alpha_m y_n y_m k(x_n*x_m,x_i)+const.$$

Similarly, an approximation for $s_i=s_{i-1}*(w*w)$ can also be found, again approximating the expansion found after the * operation. Finally, after the final iteration (p) test points can be classified using $$f(x)=\langle w,(x*s_{p-1})\rangle+b. \tag{37}$$

It is then possible to perform an approximation of the minimization of the $l_0$-norm in the feature space for polynomial kernels. Contrary to the linear case, it is not possible to explicitly look at the coordinates of the resulting w. It is defined in feature space, and only dot product can be performed easily. Thus, once the algorithm is finished, one can use the resulting classifier for prediction, but less easily for interpretation. In the linear case, on the other hand, one may also be interested in interpretation of the sparse solution, i.e., a means for feature selection.

To test the AL0M approach, it is compared to a standard SVM with no feature selection, a SVM using RFE, and Pearson correlation coefficients.

In a linear problem, six dimensions out of 202 were relevant. The probability of y=1 or −1 was equal. The first three features $\{x_1, x_2, x_3\}$ were drawn as $x_i=yN(i,1)$ and the second three features $\{x_4, x_5, x_6\}$ were drawn as $x_i=N(0,1)$ with a probability of 0.7. Otherwise, the first three features were drawn as $x_i=yN(0,1)$ and the second three as $x_i=yN(i-3,1)$. The remaining features are noise $x_i=N(0,20)$, i=7, . . . , 202. The inputs are then scaled to have a mean of zero and a standard of one.

In this problem, the first six features have redundancy and the rest of the features are irrelevant. Linear decision rules were used and feature selection was performed selecting the two best features using each of the above-mentioned methods along with AL0M SVMs, using both $l_1$ and $l_2$ multiplicative updates. Training was performed on 10, 20 and 30 randomly drawn training points, testing on a further 500 points, and averaging test error over 100 trials. The results are provided in Table 1. For each technique, the test error and standard deviation are given.

TABLE 1

| Method | 10 pts. | 20 pts. | 30 pts. |
|---|---|---|---|
| SVM | 0.344 ± 0.07 | 0.217 ± 0.04 | 0.162 ± 0.03 |
| CORR SVM | 0.274 ± 0.15 | 0.157 ± 0.07 | 0.137 ± 0.03 |
| RFE SVM | 0.268 ± 0.15 | 0.114 ± 0.10 | 0.075 ± 0.06 |
| $l_2$-AL0M SVM | 0.270 ± 0.15 | 0.097 ± 0.10 | 0.063 ± 0.05 |
| $l_1$-AL0M SVM | 0.267 ± 0.16 | 0.078 ± 0.06 | 0.056 ± 0.04 |

AL0M SVMs slightly outperform RFE SVMs, whereas conventional SVM overfit. The $l_0$ approximation compared to RFE also has a lower computational cost. In the RFE approach, n iterations are performed, removing one feature per iteration, where n is the number of input dimensions. As described with regard to the previous embodiment, RFE can be sped up by removing more than one feature at a time.

Table 2 provides the p-values for the null hypothesis that the algorithm in a given row does not outperform the algorithm in a given column using the Wilcoxon signed rank test. The Wilcoxon test evaluates whether the generalization error of one algorithm is smaller than another. The results are given for 10, 20 and 30 training points.

TABLE 2

| | | \multicolumn{5}{c}{Method} |
|---|---|---|---|---|---|---|
| | | SVM | CORR | RFE | $l_2$-AL0M SVM | $l_1$-AL0M SVM |
| SVM | (10 pts) | 1 | 1 | 1 | 1 | 1 |
| | (20 pts) | 1 | 1 | 1 | 1 | 1 |
| | (30 pts.) | 1 | 1 | 1 | 1 | 1 |
| CORR | (10 pts.) | 0 | 1 | 0.33 | 0.37 | 0.34 |
| | (20 pts) | 0 | 1 | 1 | 1 | 1 |
| | (30 pts.) | 0 | 1 | 1 | 1 | 1 |
| RFE | (10 pts.) | 0 | 0.67 | 1 | 0.56 | 0.39 |
| | (20 pts) | 0 | 0 | 1 | 0.98 | 1 |
| | (30 pts.) | 0 | 0 | 1 | 0.96 | 1 |
| $l_2$-AL0M | (10 pts) | 0 | 0.63 | 0.44 | 1 | 0.35 |
| | (20 pts) | 0 | 0 | 0.02 | 1 | 0.97 |
| | (30 pts.) | 0 | 0 | 0.04 | 1 | 0.97 |
| $l_1$-AL0M | (10 pts.) | 0 | 0.66 | 0.61 | 0.65 | 1 |
| | (20 pts) | 0 | 0 | 0 | 0.03 | 1 |
| | (30 pts.) | 0 | 0 | 0 | 0.03 | 1 |

For 20 and 30 training points, the $l_1$-AL0M SVM method outperforms all other methods. The next best results are obtained with the $l_2$-AL0M SVM. This ranking is consistent with the theoretical analysis of the algorithm—the $l_2$-norm approximation should not be as good at choosing a small subset of features relative to the $l_1$ approximation which is closer to the true $l_0$-norm minimization.

Example 2

Colon Cancer Data

Sixty-two tissue samples probed by oligonucleotide arrays contain 22 normal and 40 colon cancer tissues that must be discriminated based upon the expression of 2000 genes. Splitting the data into a training set of 50 and a test set of 12 in 500 separate trials generated a test error of 16.6% for standard linear SVMs. Then, the SVMs were trained with features chosen by three different input selection methods: correlation coefficients ("CORR"), RFE, and the $l_2$-norm approach according to the present embodiment. Subsets of 2000, 1000, 500, 250, 100, 50 and 20 genes were selected. The results are provided in the following Table 3.

TABLE 3

| # of Features | CORR SVM | RFE SVM | $l_2$-AL0M |
|---|---|---|---|
| 2000 | 16.4% ± 8 | 16.4% ± 8 | 16.4% ± 8 |
| 1000 | 17.7% ± 9 | 16.4% ± 9 | 16.3% ± 9 |
| 500 | 19.1% ± 9 | 15.8% ± 9 | 16.0% ± 9 |
| 250 | 18.2% ± 10 | 16.0% ± 9 | 16.5% ± 9 |
| 100 | 20.7% ± 10 | 15.8% ± 9 | 15.2% ± 9 |
| 50 | 21.6% ± 10 | 16.0% ± 9 | 15.1% ± 10 |
| 20 | 22.3% ± 11 | 18.1% ± 10 | 16.8% ± 10 |

AL0M SVMs slightly outperform RFE SVMs, whereas correlation coefficients (CORR SVM) are significantly worse. Table 4 provides the p-values using the Wilcoxon sign rank test to demonstrate the significance of the difference between algorithms, again showing that RFE SVM and $l_2$-AL0M outperform correlation coefficients. $l_2$-AL0M outperforms RFE for small feature set sizes.

TABLE 4

| Method | 2000 | 1000 | 500 | 250 | 100 | 50 | 20 |
|---|---|---|---|---|---|---|---|
| CORR < RFE | 0.5 | 0 | 0 | 0 | 0 | 0 | 0 |
| CORR < $l_2$-AL0M | 0.5 | 0 | 0 | 0 | 0 | 0 | 0 |
| RFE < $l_2$-AL0M | 0.5 | 0.11 | 0.92 | 0.98 | 0.03 | 0.002 | 0.001 |

Example 3

Lymphoma Data

The gene expression of 96 samples is measured with microarrays to give 4026 features, with 61 of the samples being in classes "DLCL", "FL", or "CL" (malignant) and 35 labeled otherwise (usually normal.) Using the same approach as in the previous Example, the data was split into training sets of size 60 and test sets of size 36 over 500 separate trials. A standard linear SVM obtains 7.14% error. The results using the same feature selection methods as before are shown in Table 5.

TABLE 5

| Features | CORR SVM | RFE SVM | $l_2$-AL0M SVM |
|---|---|---|---|
| 4026 | 7.13% ± 4.2 | 7.13% ± 4.2 | 7.13% ± 4.2 |
| 3000 | 7.11% ± 4.2 | 7.14% ± 4.2 | 7.14% ± 4.2 |
| 2000 | 6.88% ± 4.3 | 7.13% ± 4.2 | 7.06% ± 4.3 |
| 1000 | 7.03% ± 4.3 | 6.89% ± 4.2 | 6.86% ± 4.2 |
| 500 | 7.40% ± 4.3 | 6.59% ± 4.2 | 6.48% ± 4.2 |
| 250 | 7.49% ± 4.5 | 6.16% ± 4.1 | 6.18% ± 4.2 |
| 100 | 8.35% ± 4.6 | 5.96% ± 4.0 | 5.96% ± 4.1 |
| 50 | 10.14% ± 5.1 | 6.70% ± 4.3 | 6.62% ± 4.2 |
| 20 | 13.63% ± 5.9 | 8.08% ± 4.6 | 8.57% ± 4.5 |

RFE and the approximation to the $l_2$-AL0M again outperform correlation coefficients. $l_2$-AL0M and RFE provided comparable results. Table 6 gives the p-values using the Wilcoxon sign rank test to show the significance of the difference between algorithms.

TABLE 6

| Features | CORR < RFE | CORR < $l_2$-AL0M | RFE < $l_2$-AL0M |
|---|---|---|---|
| 4026 | 0.5 | 0.5 | 0.5 |
| 3000 | 0.578 | 0.578 | 0.5 |
| 2000 | 0.995 | 0.96 | 0.047 |
| 1000 | 0.061 | 0.04 | 0.244 |
| 500 | 0 | 0 | 0.034 |
| 250 | 0 | 0 | 0.456 |
| 100 | 0 | 0 | 0.347 |
| 50 | 0 | 0 | 0.395 |
| 20 | 0 | 0 | 0.994 |

Example 4

Yeast Dataset

A microarray dataset of 208 genes (Brown Yeast dataset) was discriminated into five classes based on 79 gene expressions corresponding to different experimental conditions. Two 8 cross-validation runs were performed. The first run was done with a classical multiclass SVM without any feature selection method. The second run was done with a SVM and a pre-processing step using the multiclass $l_2$-AL0M procedure to select features. Table 7 shows the results, i.e., that the $l_2$-AL0M multiclass SVM outperforms the classical multiclass SVM. As indicated, the number of features following feature selection is greatly reduced relative to the original set of features.

TABLE 7

| | Test Error | No. of Features |
|---|---|---|
| multiclass SVM | 4.8% | 79 |
| $l_2$-AL0M multiclass SVM | 1.3% | 20 |

As an alternative to feature selection as a pre-processing step, it may be desirable to select a subset of features after mapping the inputs into a feature space while preserving or improving the discriminative ability of a classifier. This can be distinguished from classical feature selection where one is interested in selecting from the input features. The goal of kernel space feature selection is usually one of improving generalization performance rather than improving running time or attempting to interpret the decision rule.

An approach to kernel space feature selection using $l_2$-AL0M is compared to the solution of SVMs on some general toy problems. (Note that input feature selection methods such as those described above are not compared because of w is too large in dimension, such methods cannot be easily used.) Input spaces of n=5 and n=10 and a mapping into feature space of polynomial of degree 2, i.e., $\phi(x)=\phi_{1:2}(x)$ were chosen. The following noiseless problems (target functionals) were chosen: (a) $f(x)=x_1 x_2+x_3$, (b) $f(x)=x_1$; and randomly chosen polynomial functions with (c) 95%, (d) 90%, (e) 80% and (f) 0% sparsity of the target. That is, d % of the coefficients of the polynomial to be learned are zero. The problems were attempted for training set sizes of 20, 50, 75 and 100 over 30 trials, and test error measured on a further 500 testing points. Results are plotted in FIG. 11a-f for n=5 and FIG. 12a-f for n=10. The dotted lines in the plots represent the performance of a linear SVM on a particular problem, while the solid line represent the AL0M-SVM performance. Multiplicative updates were attempted using the method described above for polynomial kernels (see, e.g., Equation 31). Note that comparing to the explicit calculation of w, which is not always possible if w is large, the performance was identical. However, this is not expected to always be the case since, if the required solution does not exist in the span of the training vectors, then Equation 36 could be a poor approximation.

In problems (a) through (d), shown in FIGS. 11a-d and 12a-d, the $l_2$-AL0M SVM clearly outperforms SVMs. This is due to the norm that SVMs use. The $l_2$-norm places a preference on using as many coefficients as possible in its decision rule. This is costly when the number of features one should use is small.

In problem (b) (FIGS. 11b and 12b), where the decision rule to be learned is linear (just one feature), the difference is the largest. The linear SVM outperforms the polynomial SVM, but the AL0M feature selection method in the space of polynomial coefficients of degree 2 outperforms the linear SVM. This suggests that one could also try to use this method as a crude form of model selection by first selecting a large capacity model then reducing the capacity by removing higher order polynomial terms.

Problems (e) and (f) (FIGS. 11e-f and 12e-f) show an 80% and 0% sparse, respectively. Note that while the method outperforms SVMs in the case of spare targets, it is not much worse when the target is not sparse, as in problem (f). In problem (e), the AL0M method is slightly better than SVMs when there are more than 50 training points, but worse otherwise. This may be due to error when making sparse rules when the data is too scarce. This suggests that it may be preferable in certain cases to choose a rule that is only partially sparse, i.e., something in between the $l_2$-norm and $l_0$-norm. It is possible to obtain such a mixture by considering individual iterations. After one or two iterations of multiplicative learning, the solution should still be close to the $l_2$-norm. Indeed, examining the test error after each of one, two and three iterations with 20 or 50 training points on problem (e), it is apparent that the performance has improved compared to the $l_2$-norm (SVM) solution. After further iterations, performance deteriorates. This implies that a method is needed to determine the optimal mixture between the $l_0$-norm and $l_2$-norm in order to achieve the best performance.

In application to feature selection, the $l_0$-norm classifier separates data using the least possible number of features. This is a combinatorial optimization problem which is solved approximately by finding a local minimum through the above-described techniques. These features can then be used for another classifier such as a SVM. If there are still too many features, they can be ranked according to the absolute value of the weight vector of coefficient assigned to them by the separating hyperplane.

Feature selection methods can also be applied to define very sparse SVM. For that purpose, it is useful to review the primal optimization problem from which SVMs are defined:

$$\min_{w,\xi_i} \|w\|_2^2 + C\sum_{i=1}^{l} \xi_i$$

$$\text{subject to: } y_i(\langle w, x_i \rangle + b) \geq 1 - \xi_i$$

$$\xi_i \geq 0$$

It is known that solutions $\hat{w}$ of such problems are expressed as a combination of the kernels $k(x_i, \ldots)$:

$$\hat{w} = \sum_{i=1}^{l} \alpha_i y_i k(x_i, \ldots) \quad (38)$$

and the non-zero $\alpha_i$'s are called the support vectors in the sense that they support the computation of the vector $\hat{w}$. One of the positive properties that has been underlined by many theoretical bounds is that when this number is small, the generalization error should be small as well. The proof of such results relies on compression arguments and it is generally believed that compression is good for learning. Following the latter assertion and applying the $l_0$-norm minimization to the vector $(\alpha_1, \ldots, \alpha_l)$, the goal is to obtain a linear model with as few non-zero $\alpha_i$ as possible. The problem to be addressed is:

$$\min_{\alpha_i, \xi_i} \|\alpha\|_0 \quad (39)$$

$$\text{subject to: } y_i \left( \sum_{j=1}^{l} \alpha_j k(x_j, x_i) \right) \geq 1$$

To solve this problem, the previously-described approximation is used. The slack variables $\xi_i$ are no longer used since the approach has been defined for hard margin ($C=+\infty$) only. The following routine is used to address the non-separable datasets, 1. Start with $\alpha=(1, \ldots, 1)$
2. Assume $\alpha_k$ is given, and solve $$\min \sum_{j=1}^{n} |\alpha_j| \quad (40)$$

$$\text{subject to: } y_i(\langle \alpha, (k(x_i, \cdot) * \alpha_k) \rangle + b) \geq 1$$

3. Let $\acute{\alpha}$ be the solution of the previous problem. Set $\alpha_{k+1} = \alpha_k * \acute{\alpha}$.
4. Go back to 2.

The present method tends to behave like a SVM but with a very sparse expansion (see Equation 38). To illustrate, the following simple example is used. The learning set consists of 100 points in $[0,1]^2$ with $\pm 1$ targets as they are drawn in FIG. 13.

Figure 13A:
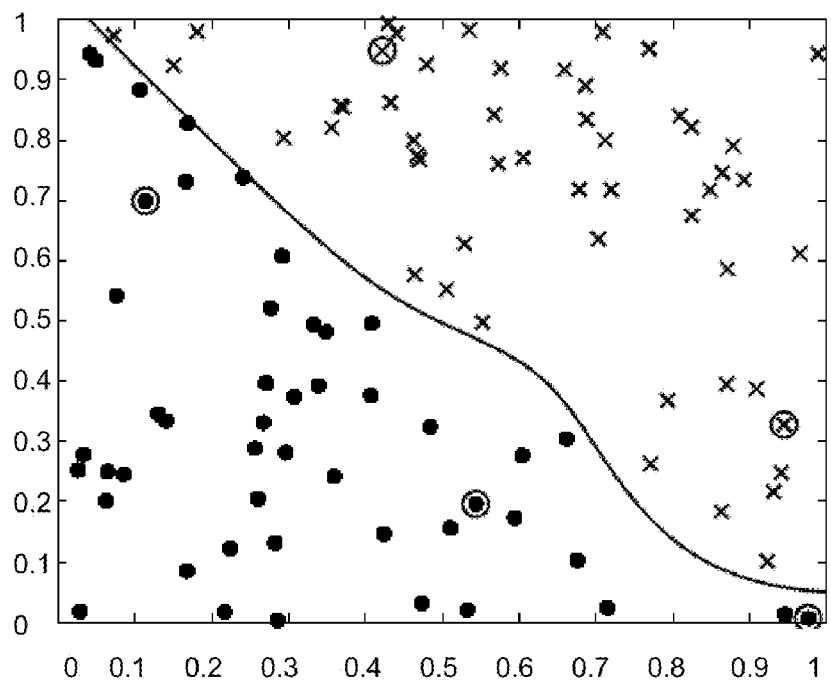
FIGS. 13a-b are plots of the results of a sparse SVM and a classical SVM, respectively, using a RBF kernel with a value of $\sigma=0.1$.
Figure 13B:
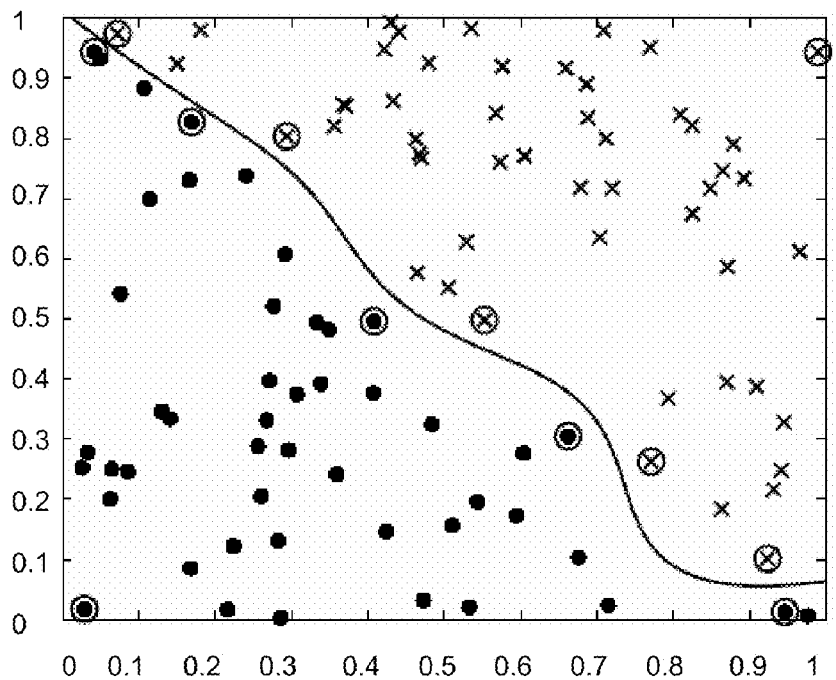

For this learning set, multiple runs of a classic SVM and a sparse SVM were run. A radial basis function (RBF) kernel with a value of $\sigma=0.1$ was used. In FIG. 13a, the result of the sparse SVM is shown, while FIG. 13b shows the result of a classic SVM. In this problem, the parse-SVM obtains a sparser and a better solution in terms of generalization error. At a first sight, this can be interpreted as a consequence of existing theoretical results about sparsity that say that sparsity is good for generalization. However, in this case, sparsity is more related to full compression than to computational dependence. "Computational dependence" here means that the outcome of the algorithm depends only on a small number of points in the learning set. For example, the support vectors of a SVM are the only points in the learning set that are used and the optimization procedure would have given the same linear model if only these points had been considered. In the present method, the resulting linear model depends on all of the training points since all of these points have been used in the optimization to reach a local minimum of the concave problem at hand. If one point is changed, even if it does not occur in the final expansion (Equation 38), it may still have a role in orienting the optimization procedure to the current local minimum rather than to another one.

Figure 14A:
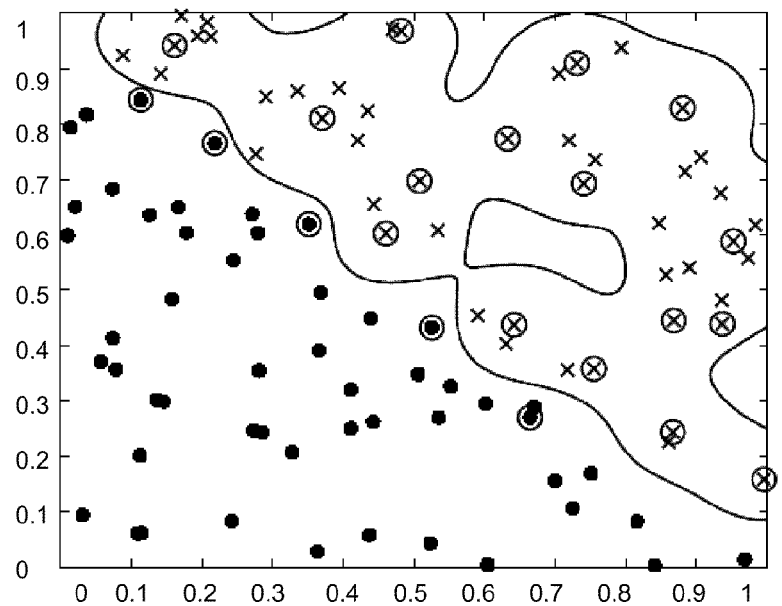
FIGS. 14a-d are plots of the results of a sparse SVM (a,c) and a classical SVM (b,d).
Figure 14B:
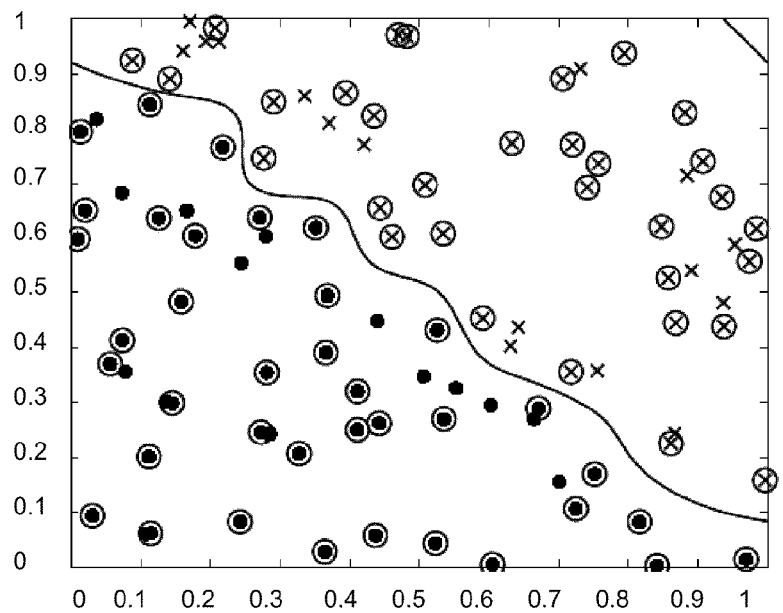
Figure 14C:
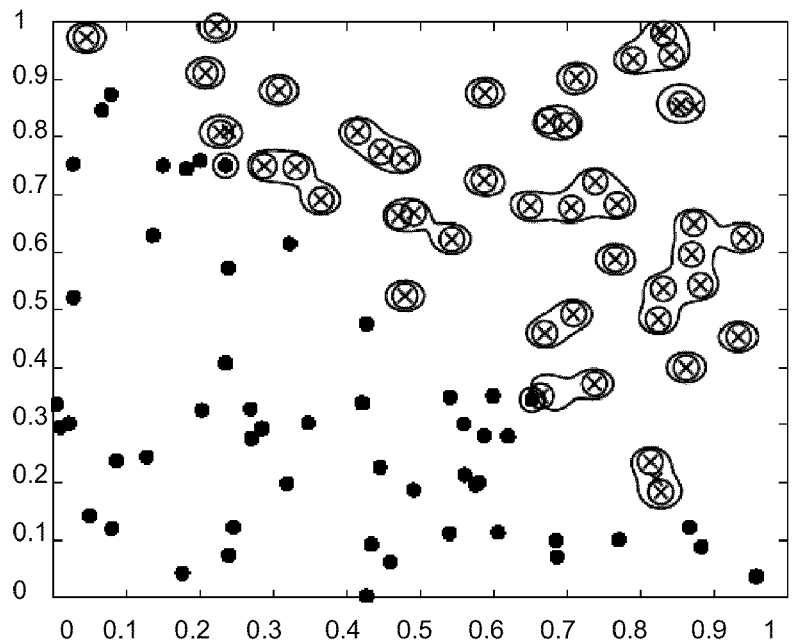
Figure 14D:
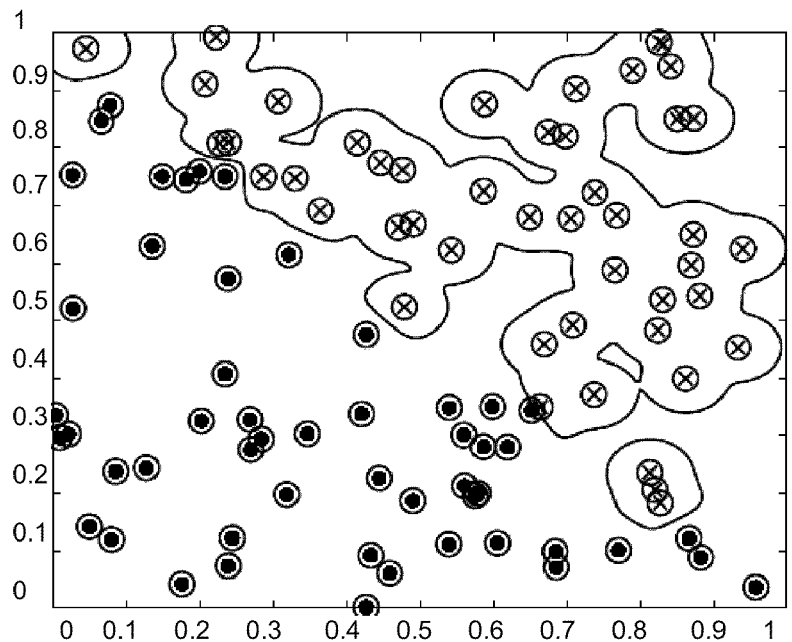
Figure 15A:
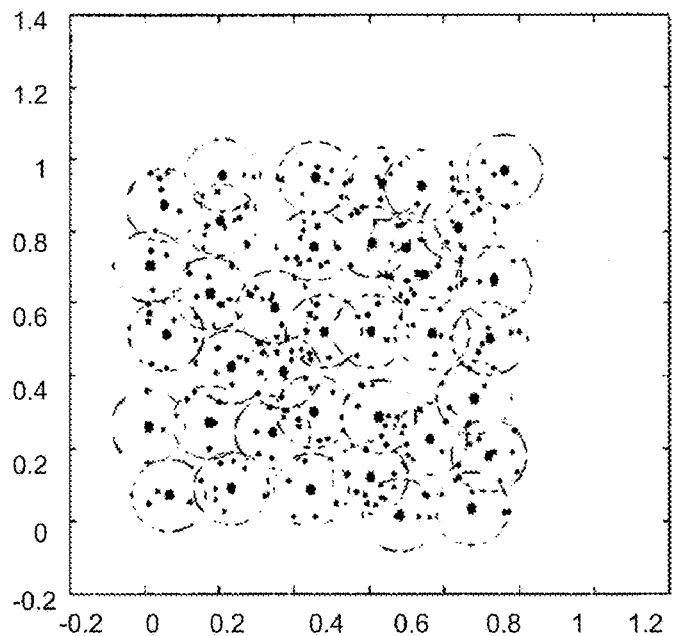
FIGS. 15a-d are plots of the results of performing guaranteed-distortion mk-vector quantization on two dimensional uniform data with varying distortion levels, where the quantizing vectors are m=37, 11, 6 and 4, respectively.
Figure 15B:
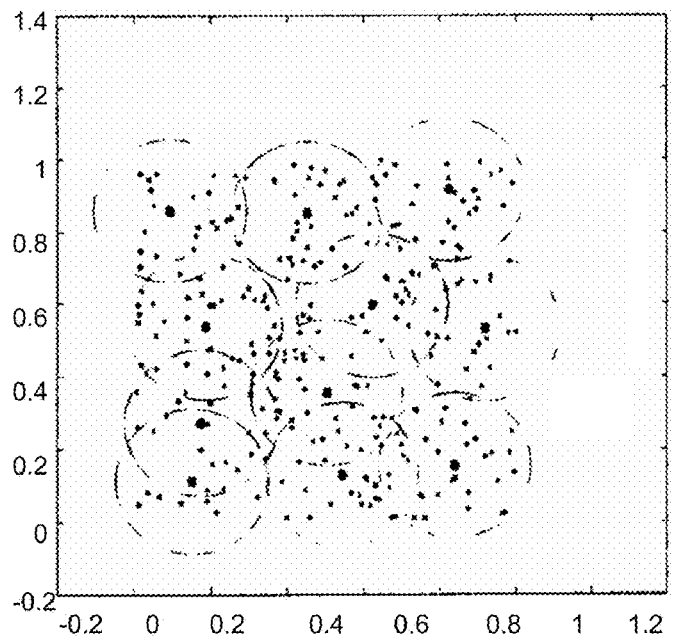
Figure 15C:
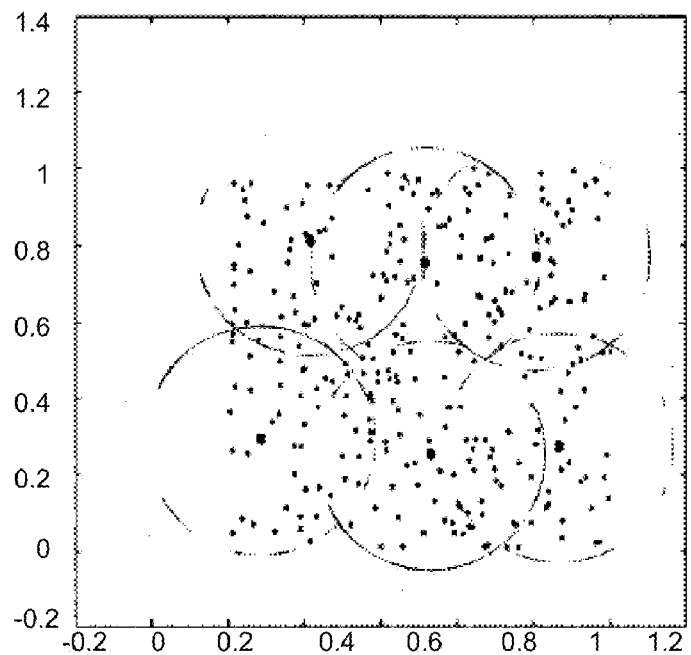
Figure 15D:
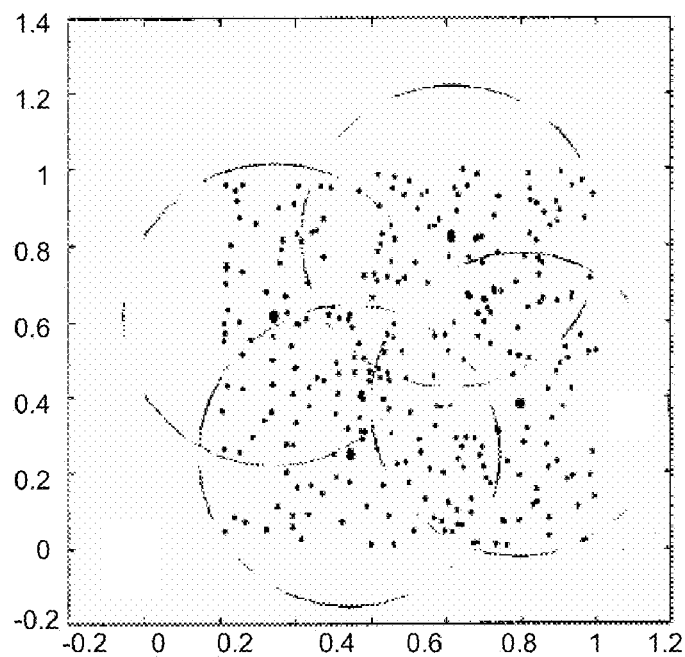

To further analyze the difference between a SVM and the sparse-SVM, the former example is continued but with a smaller value of $\sigma$. FIGS. 14a-b represent the separation obtained for a SVM and the sparse-SVM respectively, plotted for $\sigma=0.01$. The circled points in the plots indicate learning points with a non-zero $\alpha_i$. Thus, it can be seen that the number of non-zero $\alpha_i$'s is smaller with the sparse-SVM than for a classical SVM. The resulting separation is not very smooth and the margin tends to be small. This behavior is enhanced when $\sigma=0.001$, the results of which are shown in FIGS. 14c-d. Then, nearly all of the non-zero $\alpha_i$'s of the sparse-SVM are from the same class and the system has learned to answer with roughly always the same class (the circles) except in small regions.

The preceding approach can be used in a kernel-based vector quantization (VQ) method to provide a set of codebook vectors. VQ tries to represent a set of l data vectors $$x_1, \ldots, x_l \in \chi \quad (40)$$

by a reduced number of m codebook vectors $$y_1, \ldots, y_m \in \chi, \quad (41)$$

such that some measure of distortion is minimized when each x is represented by the nearest (in terms of some metric on $\chi$) y.

Often, codebooks are constructed by greedy minimization of the distortion measure, an example being the overall $l_2$ error.

$$E_{VQ} = \sum_{i=1}^{l} \|x_i - y(x_i)\|^2, \quad (42)$$

$$\text{where } y(x_i) = \operatorname*{argmin}_{y_j} \|x_i y_j\|^2. \quad (43)$$

In practice, one specifies m, initializes y, and minimizes a distortion measure such as Equation 42. Given receiver knowledge of the codebook, each x can then be compressed into $\log_2 m$ bits.

Now, consider the case where it is desired to guarantee (for the training set) a maximum level of distortion for any encoded x and automatically find an appropriate value for m. A restriction that must be imposed is that the codebook vectors must be a subset of the data. Finding the minimal such subset that can represent the data with a given level of distortion is a combinatorially hard problem, however an effective sparse codebook can be obtained using the above-described techniques.

VQ algorithms using multiplicative updates can be obtained according to the following:

Given the data of Equation 40, $\chi$ is some space endowed with a metric d. For purposes of this discussion, the term "kernel" will be used in a broader sense to mean functions $$k: \chi \times \chi \to R \quad (44)$$

not necessarily satisfying the conditions of Mercer's theorem.

Of particular interest is the kernel that indicates whether two points lie within a distance of $R \geq 0$, $$k(x, x') = 1_{\{(x, x') \in \chi \times \chi : d(x, x') \leq R\}}. \quad (45)$$

Now considering what is sometimes called the "empirical kernel map", $$\phi_l(x)=(k(x_1,x),\ldots,k(x_l,x)), \quad (46)$$

a vector $w \in R^l$ can be found such that $$w^T\phi_l(x_i)>0 \quad (47)$$

holds true for all $i=1,\ldots,l$. Then each point $x_i$ lies within a distance R of some point $x_j$ which has a positive weight $w_j>0$, i.e., the points with positive weights form a R-cover of the whole set. To see this, note that otherwise all nonzero components of w would be multiplied by a component $\phi_l$ which is 0, and the above dot product would equal 0.

Therefore, up to an accuracy of R (measured in the metric d), the $x_j$ with nonzero coefficients $w_j$ can be considered an approximation of the complete training set. (Formally, they define a R-cover of the training set in the metric d.) In order to keep the number of nonzero coefficients small, the following optimization problem is considered:

for some $q \geq 0$, compute:

$$\min_{w \in R_l} \|w\|_q \quad (48)$$

$$\text{subject to: } w^T \phi_l(x_i) \geq 1. \quad (49)$$

In this formulation, the constraint of Equation 47 has been slightly modified. To understand this, note that if a vector w satisfies Equation 47, it can be rescaled to satisfy Equation 49. For the optimization, however, Equation 49 must be used to ensure that the target function of Equation 48 cannot be trivially minimized by shrinking w.

In vector quantization, the goal is to find a small codebook of vectors to approximate the complete training set. Ideally, $q=0$ would be used, in which case $\|w\|_q$ would simply count the number of nonzero coefficients of w.

In practice, $q=1$ or $q=2$ is used, since both lead to nice optimization problems. Using this elementary optimization procedure, the multiplicative updated rule is applied.

While $q=1$ already leads to fairly sparse expansions without the multiplicative rule, $q=2$ does not. However, with the multiplicative rule, both values of q performed fairly well. At the end of the optimization, the nonzero $w_i$ corresponds to a sufficient set of codebook vectors $y_i$. Occasionally, duplicate codebook vectors are obtained. This occurs if the R-balls around two vectors contain identical subsets of the training set. To avoid this, a pruning step is performed to remove some of the remaining redundant vectors in the codebook, by sequentially removing any codebook vector that does not exclusively explain any data vector. Equivalently, the pruning step can be applied to the training set before training. If there are two points whose R-balls cover the same subsets of the training set, they can be considered equivalent, and one of them can be removed. Typically, the pruning results in the removal of a further 1-5% of the codebook.

Although the present approach is much faster than a combinatorial approach, it will still suffer from computational problems if the dataset is too large. In that case, chunking or decomposition methods can be employed. Such methods include (1) where the inner optimization uses the $l_2$-norm, it has a structure similar to the standard SVM optimization problem. In this case, SVM chunking methods can be used. (2) Forms of chunking can be derived directly from the problem structure. These include greedy chunking, SV-style chunking, and parallel chunking.

Greedy chunking involves two steps. In Step 1, start with a first chunk of $0<l_0<l$ datapoints. Solve the problem for these points, obtaining a set of $m \leq l_0$ codebook vectors. Next, go through the remaining $l-l_0$ points and discard all points that have already been covered. In the nth step, provided there are still points left, take a new chunk of $l_0$ from the remaining set, find the codebook vectors, and removed all points which are already covered.

The set of codebook vectors chosen in this manner forms a R-cover of the dataset. In the extreme case where $l_0=1$, this reduces to a greedy covering algorithm. In the other extreme, where $l_0=l$, it reduces to the original algorithm.

SV style chunking has the following inner loop:

Step 1: Start with the first chunk of $0<l_0<l$ datapoints. Solve the problem for these points, obtaining a set of $m \leq l_0$ codebook vectors and discarding the rest from the current chunk. Next, start going through the remaining $l-l_0$ points and fill up the current chunk until is has size $l_0$ again. In Step n, provided there are still points left and the current chunk has size smaller than $l_0$, proceed as above and fill it up. If it is already full, remove a fixed number of codebook vectors along with all points falling into their respective r-balls.

Once this is finished, go back and check to see whether all points of the training set (apart from those which were removed along with their codebook vectors) are r-covered by the final chunk. Any points which do not satisfy this are added to the chunk again, using the above technique for limiting the chunk size.

Note that there is no guarantee that all points will be covered after the first loop. Therefore, in the SV-style chunking algorithm, the inner loop must be repeated until everything is covered.

In parallel chunking, the dataset is split into p parts of equal size. The standard algorithm is run on each part using a kernel of width R/2. Once this is done, the union of all codebooks is formed and a cover is computed using width R/2. By the triangular inequality, a R-cover of the whole dataset is obtained.

There is no restriction on adding points to the training set. If there is a way to select points which will likely by good codebook vectors, then the algorithm will automatically pick them in its task of finding a sparse solution. Useful heuristics for finding such candidate points include a scheme where, for each codebook vector, a new point is generated by moving the codebook vector in the direction of a point having the property that, among all points that are coded only by the present codebook vector, has the maximum distance to that codebook vector. If the distance of the movement is such that no other points leave the cover, the original codebook vector can be discarded in favor of the new one.

The use of the multiplicative rule avoids a somewhat heuristic modification of the objective function (or of the kernel) that the original approach required.

Example 5

Vector Quantization

As a simple illustrative example, FIGS. 15a-d show quantizations obtained using the multiplicative kernel VQ algorithm (mk-VQ) of two-dimensional data uniformly distributed in the unit square, for values of maximum distortion $R=0.1, 0.2, 0.3$ and $0.4$, and d being the Euclidean $l_2$ distance. In all cases, the proposed algorithm finds solution which are either optimal or close to optimal. Optimality is assessed using the following greedy covering algorithm. At each step, find a point with the property that the number of points contained in a R-ball around it is maximal. Add this point to the codebook, remove all points in the ball from the training set, and, if there are still points left, go back to the beginning. In FIGS. 15a-d, for l=300, the m quantizing vectors, found automatically, are shown circled. Their numbers are m=37, 11, 6, 4, which are shown in FIGS. 15a-d, respectively. Using the greedy covering algorithm, guaranteed lower bounds on the minimal number of codebook vectors were found. The bound values are 23, 8, 4, 3. The circles of d(x, y)=R are shown for each codebook vector.

The VQ method described herein allows an upper bound to be specified on the distortion incurred for each coded vector. The algorithm automatically determines small codebooks covering the entire dataset. It works on general domains endowed with a metric, and could this equally well be used to compute coverings of function spaces. The algorithm could be used for data reduction as a pre-processing step, e.g., for classification, by separating the codebook vectors with a margin larger than R. Target values can be incorporated in the constraint such that it is preferable for the algorithm to find "pure clusters". It should be noted that although the term vector quantization has been used, the method can be applied to non-vectorial data, as long as it is possible to define a suitable distance measure d. VQ methods may also be used to compress or encode images.

Use of $l_0$-norm for multi-label problems. The preceding method for feature selection can be used in cases of multi-label problems such as frequently arise in bioinformatics. The same multiplicative update rule is used with the additional step of computing the label sets size s(x) using ranking techniques. In order to compute the ranking, a cost function and margin for multi-label models are defined.

Cost functions for multi-label problems are defined as follows:

Denote by $\chi$ an input space. An output space is considered as the space formed by all the sets of integer between 1 and Q identified as the labels of the learning problem. Such an output space contains $2^Q$ elements and one output corresponds to one set of labels. The goal is to find from a learning set $S=\{(x_1,Y_1),\ldots,(x_m,Y_1)\} \subset (\chi \times \gamma)^m$ drawn identically and independently (i.i.d.) from an unknown distribution D, a function $f$ such that the following generalization error is as low as possible:

$$R(f)=E_{(x,Y)\sim D}[c(f,x,Y)] \qquad (50)$$

The function c is a real-valued loss and can take different forms depending on how it is viewed. Here, two types of loss are considered. The first is the "Hamming Loss", which is defined as $$HL(f, x, Y) = \frac{1}{Q}|f(x)\Delta Y| \qquad (51)$$

where $\Delta$ stands for the symmetric difference of sets. Note that the more $f(x)$ is different from Y, the higher the error. Missing one label in Y is less important than missing two, which seems quite natural in many real situations. As an example, consider that the labels are possible diseases related to different genes. Many genes can share the same disease and lead to many diseases at the same time. Predicting only one disease although there are three is worse than predicting only two. Having a Hamming Loss of 0.1 means that the expected number of times a pair $(x, y_k)$ has been misclassified is 0.1. Note that if the Hamming Loss is scaled by Q, it is equal to the average number of wrong labels for each point.

Any function from $\mathcal{X}$ to $\mathcal{Y}$ can be evaluated by the Hamming loss. In some cases, another type of loss is considered.

Let $(r_1(x), \ldots, r_Q(x))$ where $r_k: \mathcal{X} \to R$, k=1, ..., Q, be real numbers which are large if k is a label of x and low otherwise. Assume a perfect predictor s(x) of the size of the label sets of x. The output $f(x)$ is computed by taking the indices of the first largest s(x) elements in $(r_1(x), \ldots, r_Q(x))$. Such a function $f$ is referred as "ranking based". Denote by $\hat{Y}$ the complementary set of Y in $\{1, \ldots, Q\}$. The Ranking Loss is define as:

$$RL(f, x, Y) = \frac{1}{|Y||\hat{Y}|}|(i, j) \in Y \times \hat{Y} \text{ s.t. } r_i(x) \le r_j(x)| \qquad (52)$$

When s(x) is not given, it must be learned from the data. To assess the quality of different predictors of the size of the label sets, the Size Loss is defined as:

$$SL(s, x, Y) = \frac{1}{Q}||Y| - s(x)| \qquad (53)$$

Note that a failure in prediction of the correct size Y is weighted differently depending on how different the prediction is from the true value. This is motivated by the same reasoning as for the Hamming Loss.

In the following, only linear models are used to perform the ranking and to learn the size of the label sets. Note, however, that the methods described herein are not intended to be limited to linear models, and that the methods may be transformed in non-linear methods by using the "kernel trick" as is known in the art. For purposes of further discussion, it will be assumed that $\mathcal{X}$ is a finite dimensional real space that can be thought of as $R^d$ where d is the number of features of the inputs. Given Q vectors $w_1, \ldots, w_Q$ and Q bias $b_1, \ldots, b_Q$, there are two ways of computing the output—the binary approach and the ranking approach.

With the binary approach:

$$f(x)=\text{sign}(\langle w_1,x\rangle+b_1, \ldots, \langle w_Q,x\rangle+b_Q) \qquad (54)$$

where the sign function applies component-wise. The value of $f(x)$ is a binary vector from which the set of labels can be retrieved easily by stating that label k is in the set ($\langle w_k, x\rangle+b_k)\geq 0$. This way of computing the output is discussed below. The natural cost function for such a model is the Hamming Loss.

With the ranking approach, assume that s(x), the size of the label set for the input x, is known, and define:

$$r_k(x)=\langle w_k,x\rangle+b_k \qquad (55)$$

and consider that a label k is in the label set of x iff $r_k(x)$ is among the first s(x) elements $(r_1(x), \ldots, r_Q(x))$.

For both systems, the empirical error measured by the appropriate cost function must be minimized while at the same time controlling the complexity of the resulting model. This reasoning is based on the principle that having a large margin plus a regularization method leads to a good system.

First looking at the binary approach, it is assumed that the function $f$ is computed as in Equation 54. This means that the decision boundaries are defined by the hyperplanes ($w_k$, x)+$b_k$=0. By analogy with the two-class case, the margin of $f$ on (x,Y) is defined as the signed distance between $(<w_1,x>)+b_1, \ldots, <w_Q, x>+b_Q)$ and the decision boundary. It is equal to:

$$\min_k y_k \frac{\langle w_k, x \rangle + b_k}{\|w_k\|} \quad (56)$$

where $y_k$ is a binary element equal to +1 if label k is in Y, and −1 otherwise. For a learning set S, the margin can also be defined as:

$$\min_{(x,Y) \in S} y_k \frac{\langle w_k, x \rangle + b_k}{\|w_k\|} \quad (57)$$

Assuming that the Hamming Loss on the learning set S is zero, the large margin paradigm we follow consists in maximizing the margin. By normalizing the parameters $(w_k, b_k)$ such that:

$$\forall (x,Y) \in S, y_k(\langle w_k, x \rangle + b_k) \leq 1 \quad (58)$$

with an equality for at least one x, the margin on $S = \{(x_i, Y_i)\}_{i=1,\ldots,Q}$ is equal to $\min_k \|w_k\|^{-1}$. Here, $Y_i$ is identified with its binary representation: $(y_{i1}, \ldots, y_{iQ}) \in \{-1, +1\}^Q$. Maximizing the margin or minimizing its inverse yields to the following problem:

$$\min_{w_k b_k} \max_k \|w_k\|^2 \quad (59)$$

$$\text{subject to: } y_{ik}(\langle w_k, x_i \rangle + b_k) \geq 1, \text{ for } i = 1, \ldots, m$$

Up to this point, it has assumed that the Hamming Loss is zero, which is unlikely to be the case in general. The Hamming Loss can be computed as:

$$HL(f, x, Y) = \frac{1}{Q} \sum_{k=1}^{Q} \theta(-y_{ik}(\langle w_k, x_i \rangle + b_k)) \quad (60)$$

where $\theta(t)=0$ for $t \leq 0$ and $\theta(t)=1$ for $t \geq 0$ .... The previous problem can be generalized by combining the minimization of the Hamming Loss and the maximization of the margin:

$$\min_{w_k b_k} \left( \max_k \|w_k\|^2 \right) + C \sum_{i=1}^{m} \frac{1}{Q} \sum_{k=1}^{Q} \theta(-1 + \xi_{ik}) \quad (61)$$

$$\text{subject to: } \begin{aligned} & y_{ik}(\langle w_k, x_i \rangle + b_k) \geq 1 - \xi_{ik}, \text{ for } i = 1, \ldots, m \\ & \xi_{ik} \geq 0 \end{aligned}$$

This problem is non-convex and difficult to solve. (It inherits from the NP-Hardness of the related two-class problems which is a classical SVM with threshold margin.) A simpler approach is to upper bound the $\theta(-1+t)$ function by the linear problem, which yields:

$$\min_{w_k b_k} \left( \max_k \|w_k\|^2 \right) + \frac{C}{Q} \sum_{i=1}^{m} \sum_{k=1}^{Q} \xi_{ik} \quad (62)$$

$$\text{subject to: } \begin{aligned} & y_{ik}(\langle w_k, x_i \rangle + b_k) \geq 1 - \xi_{ik}, \text{ for } i = 1, \ldots, m \\ & \xi_{ik} \geq 0 \end{aligned}$$

This problem is a convex problem with linear constraints and can be solved by using a gradient descent or other classical optimization method. Note that when the constant C is infinite, which corresponds to the case where the minimization of the Hamming Loss is actually the main objective function, then the system is completely decoupled and the optimization can be done on each parameter $(w_k, b_k)$ independently. For finite C, the optimization cannot be done so easily, unless the maximum over the $w_k$'s is approximated by:

$$\max_k \|w_k\|^2 \leq \sum_{k=1}^{Q} \|w_k\|^2 \leq Q \max_k \|w_k\|^2 \quad (63)$$

In this case, the problem becomes completely separated in the sense that optimizing with respect to $w_k$ does not influence the optimization with respect to $w_l$ for $l \neq k$. Note that the optimization procedure is the same as the one-against-all approach developed in the multi-class setting.

In Equation 62, the Hamming Loss is replaced by its linear approximation (here computed on (x, Y)):

$$AHL((w_k, b_k)_{k=1,\ldots,Q}, x, Y) = \frac{1}{Q} \sum_{k=1}^{Q} |-1 + y_k(\langle w_k, x \rangle + b_k)|_+ \quad (64)$$

where $|\cdot|_+$ is a function from R to $R_+$ that is the identity on $R_+$ and that equals zero on $R_-$. This linear system is then designed to minimize the AHL function rather than the Hamming distance between the binary representation of the label sets and the function $f$ defined in Equation 53. During training, it tends to place the output $f(x)$ close to the targets Y in terms of the distance derived from the AHL. When a new input x is given, the output of $f$ should then be computed via:

$$f(x) = \text{argmin}_{Y \in \mathcal{Y}} \sum_{k=1}^{Q} |-1 + y_k(\langle w_k, x \rangle + b_k)|_+ \quad (65)$$

where $\mathcal{Y}$ contains all label sets that are potential outputs. When all label sets are acceptable outputs ($\mathcal{Y} = \{-1, +1\}^Q$), Equation 65 is rewritten as Equation 54. In some cases where all label sets are not allowed ($\mathcal{Y} \subset \{-1, +1\}^Q$), both computations are different (see FIG. 16) and $f(x)$ should be calculated as above rather than using Equation 54. Such cases arise when, e.g., a Error Correcting Output Code (ECOC) is used to solve multi-class problems. T. G. Dietterich and G. Bakiri in "Solving multiclass learning problems via error-correcting output codes", *Journal of Artificial Intelligence Research*, 2:263-286, 1995, incorporated herein by reference, present a method based on error correcting code which consists in transforming a multi-class problem into a multi-label one and in using the fact that not all label sets are allowed. When the learning system outputs an impossible label set, the choice of the correcting code makes it possible to find a potentially correct label set whose Hamming distance is the closest to the output. If the system derived from Equation 62 is used with the ECOC approach, considering that the Hamming Loss is not the quantity that is minimized, the computation of the output should be done by minimizing the Hamming distance via Equation 65, which can be rewritten as:

$$f(x) = \mathrm{argmin}_{Y \in y} \sum_{k=1}^{Q} |y_k - \sigma(\langle w_k, x \rangle + b_k)| \tag{66}$$

where σ is the linear function thresholded at −1 (resp. +1) with value −1 (resp. +1).

Referring to FIG. 16, assume there are 5 labels and there are only two possible label sets: one denoted by $Y_1$ with binary representation (1, . . . , 1) and the other one $Y_2 =$ (−1, . . . , −1). The real values $(w_k, x)+-b_k$ are plotted for k=1, . . . , 5, shown as black spots. The Hamming distance between the output and $Y_1$ is 4, although it is 1 for $Y_2$. Recall that the Hamming distance is computed on the signed vector of the output. The AHL between the output and $Y_1$ is 4.2 although it is 5.8 for $Y_2$. If the final output is computed with the Hamming distance, then $Y_2$ is chosen. If it is computed via the AHL, then $Y_1$ is chosen.

Choosing the Hamming Loss leads naturally to a learning system that is very close to the one obtained from the binary approach. This suffers from a certain inability to separate points when simple configurations occur, e.g., when there are few labels and some points fall in multiple classes. This can be addressed by using the ranking approach.

The ranking approach can be broken down into two parts, the first of which is to optimize the Ranking Loss. The second part is obtained by minimizing the Size Loss $1/Q||Y|-s(x)|$. This second part is actually almost a regression problem and can be solved with the approaches known in the prior art.

The goal is to define a linear model that minimizes the Ranking Loss while having a low complexity. The notion of complexity is the margin. For systems that rank the values of $\langle w_k, x \rangle + b_k$, the decision boundaries for x are defined by the hyperplanes whose equations are $\langle w_k - w_l, x \rangle + b_k - b_l = 0$, where k belongs to the label sets of x while l does not. So, the margin of (x, Y) can be expressed as:

$$\min_{k \in Y, l \in \bar{Y}} \frac{\langle w_k - w_l, x \rangle + b_k - b_l}{\|w_k - w_l\|} \tag{67}$$

Considering that all the data in the learning set S are well ranked, the parameters $w_k$'s can be normalized such that:

$$\langle w_k - w_l, x \rangle + b_k - b_l \geq 1 \tag{68}$$

with equality for some x part of S, and $(k,l) \in Y \times \hat{Y}$. Maximizing the margin on the whole learning set can then be done via:

$$\max_{w_j, j=1,\ldots,Q} \min_{(x,Y) \in S, k \in Y, l \in \hat{Y}} \frac{1}{\|w_k - w_l\|^2} \tag{69}$$

subject to: $\langle w_k - w_l, x_i \rangle + b_k - b_l \geq 1, (k,l) \in Y_i \times \hat{Y}_i$ In the case where the problem is not ill-conditioned (two labels are always co-occurring), the objective function can be replaced by:

$$\max_{w_j} \min_{k,l} \frac{1}{\|w_k - w_l\|^2}$$

The previous problem can then be recast as:

$$\min_{w_j, j=1,\ldots,Q} \max_{k,l} \|w_k - w_l\|^2 \tag{70}$$

subject to: $\langle w_k - w_l, x_i \rangle + b_k - b_l \geq 1, \quad (k,l) \in Y_i \times \hat{Y}_i$ To provide a simpler optimization procedure, this maximum is approximated by the sum, which leads to the following problem (in the case the learning set can be ranked exactly):

$$\min_{w_j, j=1,\ldots,Q} \sum_{k,l=1}^{Q} \|w_k - w_l\|^2 \tag{71}$$

subject to: $\langle w_k - w_l, x_i \rangle + b_k - b_l \geq 1, \quad (k,l) \in Y_i \times \hat{Y}_i$ Note that a shift in the parameters $w_k$ does not change the ranking. Thus, it can be required that $$\sum_{k=1}^{Q} w_k = 0,$$

adding this constraint. In this case, Equation 71 is equivalent to:

$$\min_{w_j, j=1,\ldots,Q} \sum_{k}^{Q} \|w_k\|^2 \tag{72}$$

subject to: $\langle w_k - w_l, x_i \rangle + b_k - b_l \geq 1, \quad (k,l) \in Y_i \times \hat{Y}_i$.

To generalize this problem in the case where the learning set cannot be ranked exactly, the same reasoning is followed as for the binary case: the ultimate goal would be to minimize the margin and simultaneously minimize the Ranking Loss. The latter can be expressed directly by extending the constraints of the previous problems. If $\langle w_k - w_l, x_i \rangle + b_k - b_l > 1 - \xi_{ikl}$ for $(k,l) \in Y_i \times \hat{Y}_i$, then the Ranking Loss on the learning set S is:

$$\sum_{i=1}^{m} \frac{1}{|Y_i||\hat{Y}_i|} \sum_{k,l \in (Y_i \times \hat{Y}_i)} \theta(-1 + \xi_{ikl}) \tag{73}$$

Once again, the functions $\theta(-1+\xi_{ikl})$ can be approximated by only $\xi_{ikl}$, which gives the final quadratic optimization problem:

$$\min_{w_j, j=1,\ldots,Q} \sum_{k}^{Q} \|w_k\|^2 + C \sum_{i=1}^{m} \frac{1}{|Y_i||\hat{Y}_i|} \sum_{(k,l) \in Y_i \times \hat{Y}_i} \xi_{ikl} \tag{74}$$

subject to: $\langle w_k - w_l, x_i \rangle + b_k - b_l \geq 1 - \xi_{ikl}, (k,l) \in Y_i \times \hat{Y}_i$
$\xi_{ikl} \geq 0$ In the case where the label sets $Y_i$ have all a size of 1, the optimization problem is the same as has been derived for multi-class Support Vector Machines. For this reason, the solution of this problem is referred to as a multi-label ranking Support Vector Machine (MLR-SVM).

"Categorical regression" can be thought of as the problem of minimizing the loss:

$$CR(s, x, y) = \frac{1}{Q}|s(x) - y| \quad (75)$$

where y is the label of x (here there is only one label for a x). The term "regression" derives from the fact that this cost function is a $l_1$ cost function as in regression while "categorical" comes from the fact that s(x) is discrete. Such a setting arises when the mistakes are ordered. For example, one could imagine a situation where predicting label 1 although the true label is 4 is worse than predicting label 3. Consider the task of predicting the quality of a web page from labels provided by individuals. The individuals rate the web page as "very bad", "bad", "neutral", "good" or "very good", and the point is not only to have few mistakes, but to be able to minimize the difference between the prediction and the true opinion. A system that outputs "very bad" although the right answer is "very good" is worse than a system giving the "good" answer. Conversely, a "very good" output although it is "very bad" is worse than "bad". Such a categorical regression is in a way related to ordinal regression, the difference being no order on the targets is assumed; only order on the mistakes.

Categorical regression (CR) can be dealt with using the multi-label approach. This approach provides a natural solution of the categorical regression problem when the right setting is used. Rather than coding the labels as integers, encode them as binary vector of $\{+1, -1\}$ components:

$$\text{label } i = (\underbrace{1, \ldots, 1}_{i \text{ times}}, -1, \ldots, -1) \quad (76)$$

With this encoding, the loss CR defined previously can be expressed in terms of the Hamming Loss:

$$CR(s,x,y) = HL(\tilde{s},x,Y)$$

where $\tilde{s}$ is the function s when its output is encoded as in Equation 76, and Y is the encoded label corresponding to y. The minimization of the Hamming Loss leads naturally to the binary approach for the multi-label problem. Thus, the same system as the one defined in the binary approach section will be used. In other words, a linear system composed of many two-class sub-systems that learn how to recognize when the components of the label associated to x is +1 or -1 will be used. All possible label sets are not allowed here. As for the ECOC approach discussed previously, the function s is thus computed via Equation 66 where $\mathcal{Y}$ contains labels $1, \ldots, Q$ encoded as Equation 76.

To sum up briefly, the multi-label model is decomposed into two parts, both based on dot products and linear models. The first part ranks the labels and is obtained via Equation 74. The result is a set of parameters $(w_k^1, b_k^1)_{k=1,\ldots,Q}$. The ranking is done on the outputs $r_k(x) = \langle w_k^1, x \rangle + b_k^1$ for $k=1, \ldots, Q$.

The second part of the model predicts the size of each label sets and is obtained through Equation 62, where the maximum has been replaced by a sum. The result is also a set of parameters $(w_k^2, b_k^2)_{k=1,\ldots,Q}$. The output is computed by taking the integer whose representation (Equation 76) is the closest from the vector:

$$(\sigma(\langle w_1^2, x \rangle + b_1^2), \ldots, \sigma(\langle w_Q^2, x \rangle + b_Q^2)) \quad (77)$$

in terms of the $l_1$ distance. The function $\sigma$ is the linear function thresholded at $-1$ (resp. $+1$) with value $-1$ (resp. $+1$). Then, the output s(x) of this second model is used to compute the number of labels one has to consider in the ranking obtained by the first model.

Solving a constrained quadratic problem requires an amount of memory that is quadratic in terms of the learning set size. It is generally solved in $O(m^3)$ computational steps where the number of labels have been put into the O. Such a complexity is too high to apply these methods in many real datasets. To avoid this limitation, Franke and Wolfe's linearization method (described above regarding the AL0M embodiment) is used in conjunction with a predictor-corrector logarithmic barrier procedure.

To solve Equation 74, the dual variables $\alpha_{ikl} \geq 0$ are related to the constraints are introduced:

$$\langle w_k - w_l, x_i \rangle + b_k - b_l - 1 + \xi_{ikl} \geq 0 \quad (78)$$

and the variables $\eta_{ikl} \geq 0$ related to the constraints $\xi_{ikl} \geq 0$. The Lagrangian can then be computed:

$$L = \frac{1}{2}\sum_{k=1}^{Q}\|w_k\|^2 + C\sum_{i=1}^{m}\frac{1}{|Y_i||\bar{Y}_i|}\sum_{(k,l) \in Y_i \times \bar{Y}_i} \xi_{ikl} - \quad (79)$$

$$\ldots \sum_{i=1}^{m}\sum_{(k,l) \in Y_i \times \bar{Y}_i} \alpha_{ikl}(\langle w_k - w_l, x_i \rangle + b_k - b_l - 1 + \xi_{ikl}) -$$

$$\sum_{i=1}^{m}\sum_{(k,l) \in Y_i \times \bar{Y}_i} \eta_{ikl}$$

Setting $\partial_{b_k} L = 0$ at the optimum yields:

$$\sum_{i=1}^{m}\sum_{(j,l) \in (Y_i, \bar{Y}_i)} c_{ijl}\alpha_{ijl} = 0 \quad (80)$$

with $$c_{ijl} = \begin{cases} 0 & \text{if } j \neq k \text{ and } l \neq k \\ -1 & \text{if } j = k \\ +1 & \text{if } l = k \end{cases}$$

Note that $c_{ijl}$ depends on k. Note that the index k has been dropped to avoid excessive indices. Setting $\partial_{\xi_{ikl}} L = 0$ yields:

$$\frac{C}{|Y_i||\bar{Y}_i|} = \alpha_{ikl} + \eta_{ikl} \quad (81)$$

Then, setting $\partial_{w_k} L = 0$ yields:

$$w_k = \sum_{i=1}^{m}\left(\sum_{(j,l) \in (Y_i, \bar{Y}_i)} c_{ijl}\alpha_{ijl}\right) x_i \quad (82)$$

where $c_{ijl}$ is related to index k via Equation 80. For the sake of notation, define:

$$\beta_{ki} = \sum_{(j,l)\in(Y_i,\bar{Y}_i)} c_{ijl}\alpha_{ijl} \tag{83}$$

Then: $w_k = \sum_{i=1}^{m} \beta_{ki} x_i$.

The dual of Equation 74 can then be expressed. In order to have as simple notation as possible, it will be expressed with both variables, $\beta_{ki}$ and $\alpha_{ikl}$.

$$\max -\frac{1}{2}\sum_{k=1}^{Q}\sum_{h,i=1}^{m}\beta_{kh}\beta_{ki}\langle x_h, x_i\rangle + \sum_{i=1}^{m}\sum_{(k,l)\in(Y_i,\bar{Y}_i)}\alpha_{ikl} \tag{84}$$

subject to: $\alpha_{ikl} \in \left[0, \frac{C}{C_i}\right]$ $$\sum_{i=1}^{m}\sum_{(j,l)\in(Y_i,\bar{Y}_i)} c_{ijl}\alpha_{ijl} = 0, \text{ for } k = 1, \ldots, Q$$

The first box constraints are derived according to Equation 81, by using the fact that $\eta_{ikl} \geq 0$. The solution is a set of variables $\alpha_{ikl}$ from which $w_k$, $k=1, \ldots, Q$ can be computed via Equation 82. The bias $b_k$, $k=1, \ldots, Q$ are derived by using the Karush-Kuhn-Tucker conditions:

$$\alpha_{ikl}(\langle w_k - w_l, x_i\rangle + b_k - b_l - 1 + \xi_{ikl}) = 0 \tag{85}$$

$$(C - \alpha_{ikl})\xi_{ikl} = 0 \tag{86}$$

For indices (i, k, l) such that $\alpha_{ikl} \in (0, C)$:

$$\langle w_k - w_l, x_i\rangle + b_k - b_l = 1$$

Since $w_k$ and $w_l$ are already known, this equation can be used to compute the differences between $b_k$ and $b_l$. Note that if a primal-dual method is used to solve the dual 10, the variables $b_k$, $k=1, \ldots, Q$ are directly derived as the dual of the constraints $$\sum_{i=1}^{m}\sum_{(j,l)\in(Y_i,\bar{Y}_i)} c_{ijl}\alpha_{ijl} = 0.$$

The dual problem has an advantage compared to its primal counterpart. First, it contains only Q equality constraints and many box constraints. The latter are quite easy to handle in many optimization methods. The main problem in this case concerns the objective function: it is a quadratic function that cannot be solved directly except by storing its whole Hessian. In the case when the number of points is large as well as the number of classes, the number of variables may be too important to take a direct approach. For this reason, an approximation scheme from Franke and Wolfe is followed.

$$\max_\alpha g(\alpha) \tag{87}$$

subject to: $\langle \alpha_k, \alpha\rangle = 0$, for $k = 1, \ldots, Q$ $\alpha_j \in [0, C]$ where the vectors $\alpha_i$ have the same dimensionality as the vector $\alpha$. The procedure is as follows:

1. start with $\alpha^0 = (0, \ldots, 0)$
2. Assume at iteration p, $\alpha^p$ is given. Solve the linear problem:

$$\max_\alpha \langle \nabla g(\alpha^p), \alpha\rangle \tag{88}$$

subject to: $\langle \alpha_k, \alpha\rangle = 0$, for $k = 1, \ldots, Q$ $\alpha_j \in [0, C]$ Let $\alpha^*$ be the optimum.

3. Compute $\lambda \in [0,1]$ such that $g(\alpha^p + \lambda(\alpha^* - \alpha^p))$ is minimum. Let $\lambda^*$ be this value.
4. Set $\alpha^{p+1} = \alpha^p + \lambda^*(\alpha^* - \alpha^p)$.
5. End the procedure if $\lambda = 0$ or if $\alpha^{p+1} - \alpha^p$ has a norm lower than a fixed threshold.

The purpose of this procedure is to transform a difficult quadratic problem into many simple linear problems. As shown by Franke and Wolfe, such a procedure converges.

To apply it to the problem at hand, the gradient of the dual objective function must be computed. For that purpose, new vectors are introduced:

$$v_k^p = \sum_{i=1}^{m} \beta_{ki}^p x_i \tag{89}$$

where $\beta^p$ are computed from Equation 83 in terms of the $\alpha^p_{ikl}$. The latter are the current values of the parameter optimized using Franke and Wolfe's method. At the optimum, $w_k = v_k$. At iteration p, the objective function can thus be expressed as:

$$-\frac{1}{2}\sum_{k=1}^{Q}\|v_k^p\|^2 + \sum_{i=1}^{m}\sum_{(k,l)\in(Y_i,\bar{Y}_i)}\alpha_{ikl} \tag{90}$$

where the first part of the equation is the I part the second part is the J part.

The J part can be differentiated directly. The I part can be differentiated as:

$$\frac{\partial I}{\partial \alpha_{ikl}} = \sum_{j=1}^{Q}\langle \nabla_{v_j^p} I, \nabla \alpha_{ikl} v_j^p\rangle \tag{91}$$

$$= \langle v_k^p, x_i\rangle - \langle v_l^p, x_i\rangle$$

The computation of the gradient of the objective function can thus be done directly as soon as the vectors $v_k^p$ are given. The vectors are expressed in terms of the $\alpha^p_{ikl}$ and only dot products between them and the $x_i$'s are needed, which means that this procedure can also be used for kernels.

Denoting by $W(\alpha)$ the objective function of Equation 83 the final algorithm is as follows.

1. Start with $\alpha = (0, \ldots, 0) \in \mathbb{R}^{s_\alpha}$, where $$s_\alpha = \sum_{i=1}^{m} |Y_i||\bar{Y}_i|.$$

2. Set:

$$c_{ijl}^{k} = \begin{cases} 0 & \text{if } j \neq k \text{ and } l \neq k \\ -1 & \text{if } j = k \\ +1 & \text{if } l = k \end{cases}$$

3. For k=1, ..., Q and i=1, ..., m, compute:

$$\beta_{ki} = \sum_{(j,l)\in(Y_i,\hat{Y}_i)} c_{ijl}^{k} \alpha_{ijl}$$

4. For k=1, ..., Q and j=1, ..., m, compute:

$$\sum_{i=1}^{m} \beta_{ki} \langle x_i, x_j \rangle$$

5. Set $g_{ikl} = -(\langle w_k, x_i \rangle - \langle w_l, x_i \rangle) + 1$
6. Solve $$\min_{\alpha^{new}} \langle g, \alpha^{new} \rangle$$

with the constraints $$\alpha_{ijl}^{new} \in \left[0, \frac{C}{C_i}\right] \text{ and } \sum_{i=1}^{m} \sum_{(j,l)\in(Y_i,\hat{Y}_i)} c_{ijl}^{k} \alpha_{ijl} = 0, \text{ for } k = 1, \ldots Q$$

7. Find $\lambda \in R$ such that:
W($\alpha+\lambda d^{new}$) be maximum and $\alpha+\lambda d^{new}$ satisfies the previous constraints.
8. Set $\alpha=\alpha+\lambda d^{new}$.
9. Unless convergence, go back to Step 3.

To create the non-linear version of this algorithm, just replace the dot products $(x_i,x_j)$ by kernels $k(x_i,x_j)$.

Using the preceding steps, the memory cost of the method becomes then $O(mQQ_{max})$ where $Q_{max}$ is the maximum number of labels in the Y. In many applications, the total number of labels is much larger than $Q_{max}$. The time cost of each iteration is $O(m^2Q)$ Example 6

Toy Problem

Figure 17:
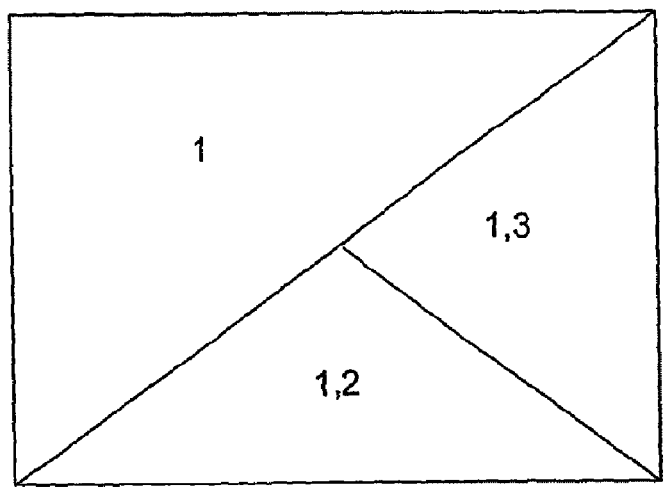
FIG. 17 illustrates a simple toy problem with three labels, one of which is associated with all inputs.

A simple toy problem is depicted in FIG. 17. There are three labels, one of which (label 1) is associated to all inputs. The learning sets were of size 50. Both the binary approach and the direct approach were applied with ranking, as described previously. Each optimization problem was solved for C=∞. The Hamming Loss for the binary approach was 0.08 although for the direct approach it was 0.

Figure 18:
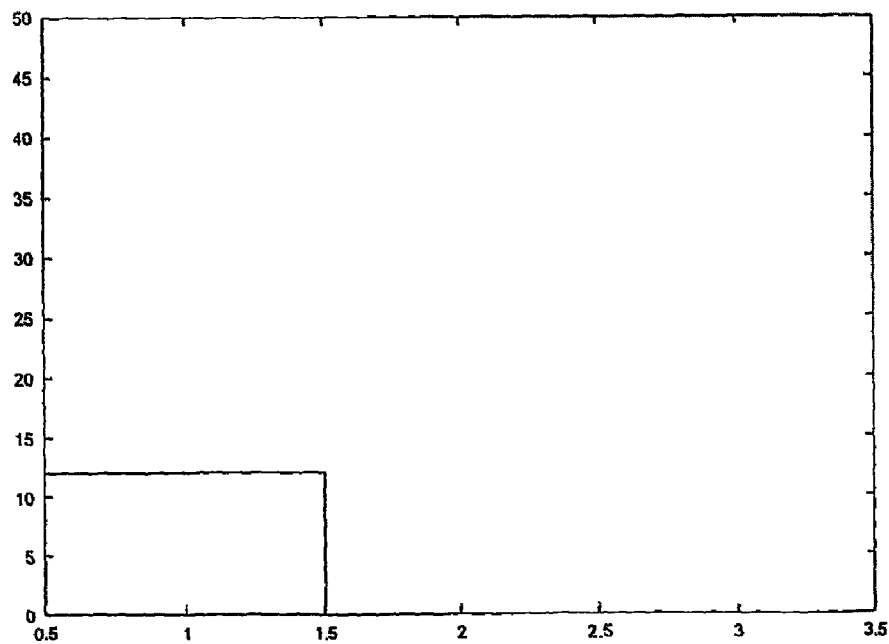
FIG. 18. is a histogram of error in the binary approach in the toy problem of FIG. 17.

To demonstrate the nature of the error that occurs using the binary approach, the distribution of missed classes is represented in FIG. 18. The x-axis represents the number of erroneous labels (missed or added) for the learning set of 50 elements; the y-axis represents the number of points out of 50. In the following, the error for a multi-label system is represented using this charts and the Hamming Loss. Such a representation enables assessment of the quality of a multi-label classifier with respect to many criterion, namely, the number of misclassified points, the number of classes that are badly predicted, etc. Note that the Hamming Loss is proportional to the sum of the height of the bars scaled by their coordinates.

Example 7

Prostate Cancer Dataset

The dataset is formed by 67 examples in a space of 7129 features and of 9 labels. The inputs are results of Micro-array experiments on different tissues coming from patients with different form of Prostate Cancer. The nine labels are described in Table 8 and represent either the position of the tissue in the body (peripheral zone, etc. ...) or the degree of malignity of the disease (G3-G4 Cancer).

Note that label 4 has only one point which implies that a direct approach will have a leave-one-out Hamming Loss of at least 0.02 (corresponding to the error when the points labelled Stroma is out).

TABLE 8

| Label | Description | No. of points in class |
|---|---|---|
| 1 | Peripheral Zone | 9 |
| 2 | Central Zone | 3 |
| 3 | Dysplasia (Cancer precursor stage) | 3 |
| 4 | Stroma | 1 |
| 5 | Benign Prostate Hyperplasia | 18 |
| 6 | G3 (cancer) | 13 |
| 7 | G4 (cancer) | 27 |
| 8 | LCM (Laser confocal microscopy) | 20 |
| 9 | 2-amplifications (related to PCR) | 34 |

Two labels have a particular meaning. The LCM label is associated with examples that have been analyzed with a Laser Confocal Microscopy technique, and the 2-amplifications label refer to examples that have had two amplifications during the PCR. These two labels are discarded so that the remaining problem is one of separating different tissue types, thus reducing the number of labels to 7. The label sets have a maximum size of 2. To assess the quality of the classifier, a leave-one-out estimate of the Hamming Loss was computed for the direct approach as well as for the binary approach with linear models and a constant C=∞. This produced an error of 0.11 for the direct approach and of 0.09 for the binary approach. FIGS. 19a-c shows the distribution of the errors for the direct and the binary approach in the leave-one-out estimate of the Hamming Loss. FIG. 19a shows the errors for the direct approach, where the values of the bars are from left to right: 4, 19 and 3. FIG. 19b shows the errors for the binary approach where the values of the bars are from left to right: 20, 10 and 1. FIG. 19c shows the errors for the binary approach when the system is forced to output at least one label, where the values of the bars are from left to right: 9, 16 and 2.

The direct approach yields mistakes on 26 points although the binary approach makes mistakes on 31 points. In terms of the Hamming Loss, the binary approach is the best although in terms of the number of correctly classified input points, the direct approach wins. As previously discussed, the binary approach is naturally related to the Hamming Loss and it seems quite natural that it minimizes its value. On the other hand, if one wants to minimize the number of points where there is an error, the direct approach is better.

In the direct approach, the empty label set output is not possible. If the binary system is forced to provide at least one label on all the input sample, the Hamming Loss for the binary becomes 0.10, and the number of points where there is an error is 27. Thus, both direct and binary systems are quite close.

Since the goal in this particular application is to discriminate the malign cells from the benign ones, the multi-labelled approach was applied for labels 4-7 only, reducing the number of labels to 4 and the number of points in the learning set to 56. With the same setting as above, the leave-one-out estimate of the Hamming Loss was 0.14 for the direct approach, and 0.14 for the binary approach. The same experiment as above was performed by computing the Hamming Loss of the binary system when the latter is forced to give at least one label, producing a Hamming Loss of 0.16. In this particular application, the direct approach is better, yielding a system with the same or a lower Hamming Loss than the binary approach.

The results of the leave-one-out estimate of the Hamming Loss for the Prostate Cancer Database using 4 labels are provided in FIG. 20a-c. FIG. 20a is a histogram of the errors for the direct approach, where the values of the bars are from left to right: 2, 13 and 1). FIG. 20b is a histogram of the errors for the binary approach, where the values of the bars are from left to right: 12, 8 and 1. FIG. 20c is a histogram of the errors for the binary approach when the system is forced to output at least one label, where the values of the bars are from left to right: 7, 13 and 1.

The partial conclusion of these experiments is that defining a direct approach does not provide significant improvement over a simple binary approach. Given the nature of the problem we have considered, such a conclusion seems quite natural. It is interesting to note that both the direct and the binary approach give similar results even though the direct approach has not been defined to minimize the Hamming Loss.

The above methods can be applied for feature selection in a multi-label problem in combination with the method for minimization of the $l_o$ norm of a linear system that was discussed relative to the previous embodiment. Note that multi-label problems are omnipresent in biological and medical applications.

Consider the following multiplicative update rule method:
1. Inputs: Learning set $S=((x_i, Y_i))_{i-1, \ldots, m}$.
2. Start with $w_1, b_1, \ldots, w_Q, b_Q)=(0, \ldots, 0)$.
3. At iteration t, solve the problem:

$$\min_{w_k, b_k} \sum_{k=1}^{m} \|w_k\|^2 \quad (92)$$

subject to: $\langle w_k * w_k^t, x_i \rangle - \langle w_l * w_l^t, x_i \rangle + b_k - b_l \geq 1$, for $(k, l) \in Y_i \times \hat{Y}_i$ where $w*w^t$ is the component-wise multiplication between w and $w^t$.

4. Let w be the solution. Set: $w^{t+1}=w*w^t$.
5. Unless $w^{t+1}=w^t$, go back to step 2.
6. Output $w^{t+1}$.

This method is an approximation scheme to minimize the number of non-zero components of $(w_1, \ldots, w_Q)$ while keeping the constraints of Equation 92 satisfied. It is shown to converge in the prior discussion. If the multi-label problem is actually a ranking problem, then this feature selection method is appropriate.

For real multi-label problems, a step is still missing, which is to compute the label sets size s(x).

Using the Prostate Cancer Database, assume that the value of the label set sizes is known. First, consider the entire dataset and compute how many features can be used to find the partial ranking between labels. Nine features are sufficient to rank the data exactly. Next, use the feature selection method in conjunction with a learning step afterwards to see if choosing a subset of features provide an improvement in the generalization performance. For this purpose, a leave-one-out procedure is used. For each point in the learning set, remove that point, perform the feature selection and run a MLR-SVM with the selected features, compute the Hamming Loss on the removed point. All SVMs were trained with $C=\infty$. The results are summarized in Table 9. The mean of features is given with its standard deviation in parenthesis. The number of errors counts the number of points that have been assigned to a wrong label set.

TABLE 9

| | No. of Features | Hamming Loss | No. of Errors |
|---|---|---|---|
| Direct + Direct | 9.5 (±1) | 0.10 | 11 |
| Direct + Binary | 9.5 (±1) | 0.11 | 19 |

Figure 21B:
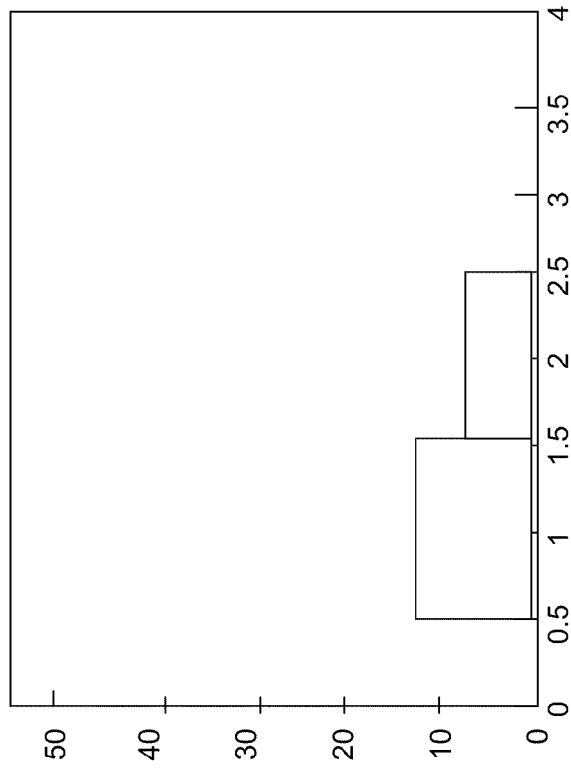
FIG. 21b is a histogram of the errors for the binary approach, where the values of the bars are from left to right: 12 and 7.
Figure 21A:
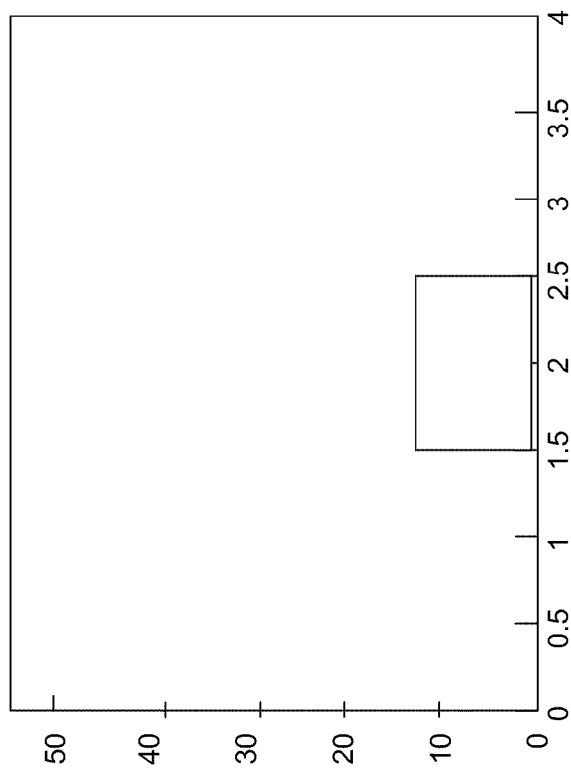
FIG. 21a is a histogram of the errors for the direct approach where the value of one bars is 11.

FIG. 21 shows the distribution of the mistakes using the leave-one-out estimate of the Hamming Loss for the Prostate Cancer Database using 4 labels with Feature selection. FIG. 21a is a histogram of the errors for the direct approach where the value of one bars is 11. FIG. 21b is a histogram of the errors for the binary approach, where the values of the bars are from left to right: 12 and 7. This comparison may seem a little biased since the function s(x) that computes the size of the label sets is known perfectly. Note, however, that for the binary approach, feature selection preprocessing provides a better leave-one-out Hamming Loss. There are also fewer mislabeled points than there are if no feature selection is used.

Although the preceding discussion has covered only linear systems, the inventive method can be applied to more complex problems when only dot-products are involved. In this case, the kernel trick can be used to transform a linear model into a potentially highly non-linear one. To do so, it suffices to replace all the dot products $(x_i, x_j)$ by $k(x_i, x_j)$ where k is a kernel. Examples of such kernels are the Gaussian kernel $\exp(-\|x_i - x_j\|^2/\sigma^2)$ or the polynomial kernel $(\langle(x_i, x_j)+1\rangle^d$ for $d \in N\setminus\{0\}.\}$. If these dot products are replaced, it becomes apparent that the other dot products $(w_k, x_t)$ can also be computed via Equation 81 and by linearity of the dot product. Thus, the MLR-SVM and the ML-SVM introduced can also be defined for different dot product computed as kernels.

Feature Selection by Unbalanced Correlation. A fourth method for feature selection uses the unbalanced correlation score ($\text{CORR}_{ub}$) according to criterion $$f_i = \sum_i X_{ij} Y_i, \quad (93)$$

where the score for feature j is $f_j$ and a larger score is assigned to a higher rank. Before this method is described, note that due to the binary nature of the features, this criterion can also be used to assign rank to a subset of features rather than just a single feature. This can be done by computing the logical OR of the subset of features. If this new vector is designated as x, compute $$\sum_i x_i Y_i.$$

A feature subset which has a large score can thus be chosen using a greedy forward selection scheme. This score favors features correlated with the positive examples, and thus can provide good results for very unbalanced datasets.

The dataset used for testing of the $CORR_{ub}$ feature selection method concerns the prediction of molecular bioactivity for drug design. In particular, the problem is to predict whether a given drug binds to a target site on thrombin, a key receptor in blood clotting. The dataset was provided by DuPont Pharmaceuticals.

The data was split into a training and a test set. Each example (observation) has a fixed length vector of 139,351 binary features (variables) in {0,1}. Examples that bind are referred to as having label +1 (and hence being called positive examples). Conversely, negative examples (that do not bind) are labeled −1.

In the training set there are 1909 examples, 42 of which are which bind. Hence the data is rather unbalanced in this respect (42 positive examples is 2.2% of the data). The test set has 634 examples. The task is to determine which of the features are critical for binding affinity and to accurately predict the class values using these features.

Performance is evaluated according to a weighted accuracy criterion due to the unbalanced nature of the number of positive and negative examples. That is, the score of an estimate Y of the labels Y is:

$$\ell_{weighted}(Y, \hat{Y}) = \frac{1}{2}\left(\frac{\#\{\hat{Y} : Y = 1 \wedge \hat{Y} = 1\}}{\#\{Y : Y = 1\}}\right) + \frac{\#\{\hat{Y} : Y = -1 \wedge \hat{Y} = -1\}}{\#\{Y : Y = -1\}} \quad (94)$$

where complete success is a score of 1. In this report we also multiply this score by 100 and refer to it as percentage (weighted) success rate.

Also of interest is (but less important) is the unweighted success rate. This is calculated as:

$$\ell_{unweighted}(Y, \hat{Y}) = \sum_i \frac{1}{2}|\hat{Y}_i - Y_i|. \quad (95)$$

An important characteristic of the training set is that 593 examples have all features equal to zero. 591 of these examples are negative and 2 of these are positive (0.3%). In the training set as a whole, 2.2% are positive, so new examples with all features as zero should be classified negative. As not much can be learned from these (identical) examples, all but one were discarded, which was a negative example. The primary motivation for doing this was to speed up computation during the training phase A summary of some characteristics of the data can be found in Table 10 below. Considering the training data as a matrix X of size 1909×139351, the number of nonzero features for each example, and the number of nonzero values for each feature were computed.

TABLE 10

| Type | min | max | mean | median | std |
|---|---|---|---|---|---|
| Nonzeroes in example i, $s_i = \Sigma_j X_{ij}$ | 0 | 29744 | 950 | 136 | 2430 |
| Nonzeroes in feature j, $f_j = \Sigma_i X_{ij}$ | 1 | 634 | 13.01 | 5 | 22.43 |

The results show that the data is very sparse. Many features have only a few nonzero values. If there are noisy features of this type, it can be difficult to differentiate these features from similarly sparse vectors which really describe the underlying labeling. This would suggest the use of algorithms which are rather suspicious of all sparse features (as the useful ones cannot be differentiated out). The problem, then, is whether the non-sparse features are discriminative.

The base classifier is a SVM. The current experiments employ only linear functions (using the kernel K=X*X') or polynomial functions K=(X*X'+1)$^q$, where X is the matrix of training data.

For use in unbalanced datasets, methods are used to control training error. To introduce decision rules which allow some training error (SVMs otherwise try to correctly separate all the data) one can modify the kernel matrix by adding a diagonal term. This controls the training error in the following way. An SVM minimizes a regularization term R (a term which measures the smoothness of the chosen function) and a training error term multiplied by a constant C:R+C*L. Here, $$L = \sum_i \xi_i^2$$

where $\xi_i = Y_i - \hat{Y}_i$ (the estimate $\hat{Y}$ of the label Y for example i is a real value) and so the size of the diagonal term is proportional to 1/C. Large values of the diagonal term will result in large training error.

Although there are other methods to control training error, the following method is adopted for use on unbalanced datasets. In this method, there is a trade off of errors between negative and positive examples in biological datasets achieved by controlling the size of the diagonal term with respect to the rows and columns belonging to negative and positive examples. The diagonal term is set to be n(+)/n*m for positive examples and n(−)/n*m for negative examples, where n(+) and n(−) are the number of positive and negative examples respectively, n=n(+)+n(−) and m is the median value of the diagonal elements of the kernel.

After training the SVM and obtaining a classifier control of the false positive/false negative trade off, ROCS (receiver operating characteristics) is evaluated for this classifier. This can be done by considering the decision function of an SVM which is a signed real value (proportional to the distance of a test point from the decision boundary). By adding a constant to the real value before taking the sign, a test point is more likely to be classified positive.

A very small number of features (namely, 4) was chosen using the RFE, $l_0$-norm and $CORR_{ub}$ three feature selection methods to provide a comparison. For $CORR_{ub}$ the top 4 ranked features are chosen using Equation 93. In all cases, the features chosen were tested via cross validation with the SVM classifier. The cross validation was eight-fold, where the splits were random except they were forced to be balanced, i.e., each fold was forced to have the same ratio of positive and negative examples. (This was necessary because there were only 42 positive examples (40, if one ignores the ones with feature vectors that are all zeros). If one performed normal splits, some of the folds may not have any positive examples.) The results are given in Table 11 below, which shows the cross validation score (cv), the training score and the actual score on the test set for each features selection method. The score function is the $l_{weighted}$ of Equation 94, i.e., optimal performance would correspond to a score of 1.

TABLE 11

|  | cv | train | test |
|---|---|---|---|
| RFE | 0.5685 ± 0.1269 | 0.7381 | 0.6055 |
| $l_0$-C | 0.6057 ± 0.1264 | 0.7021 | 0.4887 |
| $CORR_{ub}$ | 0.6286 ± 0.1148 | 0.6905 | 0.6636 |

Note that the test score is particularly low on the $l_0$-C method. Recall that the balance between classifying negative and positive points correctly is controlled by the diagonal term added to the kernel, which was fixed a priori. It is possible that by controlling this hyperparameter one could obtain better results, and it may be that the different systems are unfairly reflected, however this requires retraining with many hyperparameters. Compensation for the lack of tuning was attempted by controlling the threshold of the real valued function after training. In this way one obtains control of the number of false negatives and false positives so that as long as the classifier has chosen roughly the correct direction (the correct features and resulting hyperplane), results can improve in terms of the success rate. To verify this method, this parameter was adjusted for each of the algorithms, then the maximum value of the weighted CV (cross validation) success rate was taken. This is shown in Table 12 with the values $cv_{max}$, $train_{max}$ and $test_{max}$.

TABLE 12

|  | $cm_{max}$ | $train_{max}$ | $test_{max}$ |
|---|---|---|---|
| RFE | 0.6057 ± 0.1258 | 0.7381 | 0.6137 |
| $l_0$-C | 0.6177 ± 0.1193 | 0.8079 | 0.5345 |
| $CORR_{ub}$ | 0.6752 ± 0.1788 | 0.8669 | 0.7264 |

The best performance on the test set is 72.62%. The best results were given by the unbalanced correlation score ($CORR_{ub}$) method. The two other features selection methods appear to overfit. One possible reason for this is these methods are not designed to deal with the unbalanced nature of the training set. Moreover, the methods may be finding a too complex combination of features in order to maximize training score (these methods choose a subset of features rather than choosing features independently). Note also that both methods are in some sense backward selection methods. There is some evidence to suggest that forward selection methods or methods which treat features independently may be more suitable for choosing very small numbers of features. Their failure is entirely plausible in this situation given the very large number of features.

The next step in the analysis of the dataset was to select the type of kernel to be used. Those considered were linear kernels and polynomials of degrees 2 and 3. The results are given in Tables 13 and 14.

TABLE 13

|  | cv | train | test |
|---|---|---|---|
| $CORR_{ub}$ linear | 0.6286 ± 0.1148 | 0.6905 | 0.6636 |
| $CORR_{ub}$ poly 2 | 0.6039 ± 0.1271 | 0.6905 | 0.6165 |
| $CORR_{ub}$ poly 3 | 0.5914 ± 0.1211 | 0.6429 | 0.5647 |

TABLE 14

|  | $cv_{max}$ | $train_{max}$ | $test_{max}$ |
|---|---|---|---|
| $CORR_{ub}$ linear | 0.6752 ± 0.1788 | 0.8669 | 0.7264 |
| $CORR_{ub}$ poly 2 | 0.6153 ± 0.1778 | 0.8669 | 0.7264 |
| $CORR_{ub}$ poly 3 | 0.6039 ± 0.1446 | 0.8201 | 0.7264 |

Next, the number of features chosen by the $CORR_{ub}$ method was adjusted. The greedy algorithm described above was used to add n=1, . . . , 16 more features to the original 4 features that had been selected independently using Equation 93. Tests were also run using only 2 or 3 features. The results are given in the Tables 15a-c.

TABLE 15a

| features | 2 | 3 | 4 | 5 | 6 | 7 | 8 |
|---|---|---|---|---|---|---|---|
| train | 0.5833 | 0.6905 | 0.6905 | 0.7262 | 0.7500 | 0.8212 | 0.8212 |
| test | 0.4979 | 0.6288 | 0.6636 | 0.6657 | 0.6648 | 0.7247 | 0.7221 |
| cv | 0.5786 | 0.6039 | 0.6286 | 0.6745 | 0.7000 | 0.6995 | 0.6992 |
| (cv-std) | 0.0992 | 0.1271 | 0.1448 | 0.2008 | 0.1876 | 0.1724 | 0.1722 |

TABLE 15b

| features | 9 | 10 | 11 | 12 | 13 | 14 | 15 |
|---|---|---|---|---|---|---|---|
| train | 0.8212 | 0.8212 | 0.8093 | 0.8095 | 0.8095 | 0.8095 | 0.8452 |
| test | 0.7449 | 0.7449 | 0.7449 | 0.7336 | 0.7346 | 0.7346 | 0.7173 |
| cv | 0.7341 | 0.7341 | 0.7216 | 0.7218 | 0.7140 | 0.7013 | 0.7013 |
| (cv-std) | 0.1791 | 0.1791 | 0.1773 | 0.1769 | 0.1966 | 0.1933 | 0.1933 |

TABLE 15c

| features | 16 | 17 | 18 | 19 | 20 |
|---|---|---|---|---|---|
| train | 0.8452 | 0.8452 | 0.8571 | 0.8571 | 0.8571 |
| test | 0.6547 | 0.6701 | 0.6619 | 0.6905 | 0.6815 |
| cv | 0.7013 | 0.7013 | 0.7013 | 0.7010 | 0.7007 |
| (cv-std) | 0.1933 | 0.1933 | 0.1933 | 0.1934 | 0.1940 |

In Tables 16a-c, the same results are provided showing the maximum value of the weighted success rate with respect to changing the constant factor added to the real valued output before thresholding the decision rule (to control the tradeoff between false positives and false negatives). The best success rate found on the test set using this method is 75.84%. Cross-validation (CV) results indicate that 9 or 10 features produce the best results, which gives a test score of 74.49%.

TABLE 16a

| features | 2 | 3 | 4 | 5 | 6 | 7 | 8 |
|---|---|---|---|---|---|---|---|
| $train_{max}$ | 0.8431 | 0.8669 | 0.8669 | 0.9264 | 0.9502 | 0.8212 | 0.8212 |
| $test_{max}$ | 0.5000 | 0.6308 | 0.7264 | 0.7264 | 0.7275 | 0.7247 | 0.7250 |
| $cv_{max}$ | 0.6624 | 0.6648 | 0.6752 | 0.7569 | 0.7460 | 0.7460 | 0.7489 |
| ($cv_{max}$-std) | 0.1945 | 0.0757 | 0.1788 | 0 | 0.1949 | 0.1954 | 0.1349 |

TABLE 16b

| features | 9 | 10 | 11 | 12 | 13 | 14 | 15 |
|---|---|---|---|---|---|---|---|
| $train_{max}$ | 0.8212 | 0.8212 | 0.8212 | 0.8450 | 0.8450 | 0.8450 | 0.8571 |
| $test_{max}$ | 0.7449 | 0.7449 | 0.7472 | 0.7574 | 0.7584 | 0.7584 | 0.7421 |
| $cv_{max}$ | 0.7583 | 0.7599 | 0.7724 | 0.7729 | 0.7731 | 0.7734 | 0.7713 |
| ($cv_{max}$-std) | 0.1349 | 0.1349 | 0.1349 | 0.1245 | 0.1128 | 0.1187 | 0.1297 |

TABLE 16c

| features | 16 | 17 | 18 | 19 | 20 |
|---|---|---|---|---|---|
| $train_{max}$ | 0.8571 | 0.8571 | 0.8690 | 0.8690 | 0.8690 |
| $test_{max}$ | 0.7454 | 0.7277 | 0.7205 | 0.7289 | 0.7156 |
| $cv_{max}$ | 0.7963 | 0.7838 | 0.7815 | 0.7713 | 0.7669 |
| ($cv_{max}$-std) | 0.1349 | 0.1297 | 0.1349 | 0.1245 | 0.1349 |

Note that the training score does not improve as expected when more complicated models are chosen. This is likely the result of two factors: first, the size of the diagonal term on the kernel may not scale the same resulting in a different value of the cost function for training errors, and second (which is probably the more important reason) training error is only approximately minimized via the cost function employed in SVM which may suffer particularly in this case of unbalanced training data.

Based on the CV results, linear functions were selected for the rest of the experiments.

To provide a comparison with the SVM results, a C4.5 (decision tree) classifier and k-nearest neighbors (k-NN) classifier were each run on the features identified by cross validation. SVMs gave a test success of 0.7449, but standard C4.5 gave a test success of 0.5. The problem is that the standard version of C4.5 uses the standard classification loss as a learning criterion and not a weighted loss. Therefore, it does not weight the importance of the positive and negative examples equally and, in fact, in the training set classifies all examples negative. "Virtual" training examples were created by doubling some of the points to make the set seem more balanced, however, this did not help. It appears that the C4.5 algorithm internally would need to be modified internally to make it work on this dataset.

In the k-NN comparison, the decision rule is to assign the class of the majority of the k-nearest neighbors $x_{i=1,\ldots,l}$ of a point x to be classified. However, the distance measure was altered so that if $x_i$ is a positive example, the measure of distance to x was scaled by a parameter $\lambda$. By controlling $\lambda$, one controls the importance of the positive class. The value of $\lambda$ could be found by maximizing over success rates on the training set, but in the present experiments, the maximum performance on the test set over the possible choices of $\lambda$ to get an upper bound on the highest attainable success rate of k-NN was observed. The results for this method (k-$NN_{max}$) and conventional k-NN are given in Table 17. These results fall short of the previously-described SVM results (0.7449) with SVM outperforming both variations of k-NN for all values of the hyperparameters.

TABLE 17

| k | 1 | 2 | 3 | 4 | 5 | 6 | 7 | 8 |
|---|---|---|---|---|---|---|---|---|
| k-NN | 0.57 | 0.20 | 0.64 | 0.63 | 0.63 | 0.37 | 0.50 | 0.50 |
| k-$NN_{max}$ | 0.59 | 0.35 | 0.65 | 0.65 | 0.65 | 0.41 | 0.50 | 0.50 |

The present embodiment of the feature selection method was compared against another standard: correlation coefficients. This method ranks features according to the score $$\left| \frac{\mu_{(+)} - \mu_{(-)}}{\sigma_{(+)} + \sigma_{(-)}} \right|,$$

where $\mu_{(+)}$ and $\mu_{(-)}$ are the mean of the feature values for the positive and negative examples respectively, and $\sigma_{(+)}$ and $\sigma_{(-)}$ are their respective standard deviations.

The results of this comparison are given below in Table 18. Overall, correlation coefficients are a poor feature selector, however, SVMs perform better than either of the other classifiers (k-NN or C4.5) using feature selection based on correlation coefficients.

TABLE 18

| features | 2 | 4 | 6 | 8 | 10 | 12 | 14 | 16 | 18 |
|---|---|---|---|---|---|---|---|---|---|
| $SVM_{max}$ | 0.62 | 0.62 | 0.59 | 0.59 | 0.52 | 0.52 | 0.50 | 0.51 | 0.50 |
| k-$NN_{max}$ | 0.62 | 0.59 | 0.53 | 0.55 | 0.53 | 0.51 | 0.52 | 0.51 | 0.52 |
| C4.5 | 0.62 | 0.57 | 0.55 | 0.51 | 0.49 | 0.52 | 0.53 | 0.51 | 0.51 |

Also considered was the following feature selection scoring method which involved selecting the features with the highest unbalanced correlation score without any entry assigned to negative samples. This can be achieved by computing the score $$f_i = \sum_{Y_i=1} X_{ij} - \lambda \sum_{Y_i=-1} X_{ij}$$

for large values of $\lambda$. However, in practice, if $\lambda \geq 3$, the results are the same on this dataset.

The results for the unbalanced correlation score with no negative entries are shown in Table 19 using an OR function as the classifier. The test success rates are slightly better than those obtained for the previous correlation score (in which $\lambda=1$), but the advantage is that there are fewer hyperparamers to adjust. Unfortunately, the cross validation results do not accurately reflect test set performance, probably because of the non-iid nature of the problem. Because of its simplicity, this feature selection score is used in the following description of transductive algorithms.

TABLE 19a

| Feat. | 1 | 2 | 3 | 4 | 5 | 6 | 7 | 8 | 9 | 10 |
|---|---|---|---|---|---|---|---|---|---|---|
| Tr. | 66.6 | 66.6 | 66.6 | 66.6 | 66.6 | 66.6 | 71.4 | 76.1 | 76.1 | 76.1 |
| Ts. | 63.0 | 72.8 | 74.6 | 74.9 | 74.99 | 75.3 | 76.9 | 74.4 | 74.7 | 74.6 |

TABLE 19b

| Feat. | 11 | 12 | 13 | 14 | 15 | 16 | 17 | 18 | 19 | 20 |
|---|---|---|---|---|---|---|---|---|---|---|
| Tr. | 76.1 | 76.1 | 76.1 | 76.1 | 76.1 | 77.3 | 77.3 | 77.3 | 79.7 | 80.9 |
| Ts. | 73.4 | 73.4 | 73.4 | 76.2 | 76.2 | 75.7 | 75.0 | 73.8 | 69.5 | 65.0 |

In inductive inference, which has been used thus far in the learning process, one is given data from which one builds a general model and then applies this model to classify new unseen (test) data. There also exists another type of inference procedure, so called transductive learning, in which one takes into account not only given data (the training set) but also the (unlabeled) data that one wishes to classify. In the strictest sense, one does not build a general model (from specific to general), but classifies the test examples directly using the training examples (from specific to specific). As used herein, however, algorithms are considered which take into account both the labeled training data and some unlabeled data (which also happens to be the test examples) to build a more accurate (general) model in order to improve predictions.

Using unlabeled data can become very important with a dataset where there are few positive examples, as in the present case. In the following sections, experiments with a simple transduction algorithm using SVMs are shown to give encouraging results.

A naive algorithm was designed to take into account information in the test. First, this algorithm used the SVM selected via cross validation. Then, calculated the real valued output $y=g(x)$ of this classifier on the test set was calculated. (Before taking the sign—this is proportional to the distance from the hyperplane of a test point). These values were then used as a measure of confidence of correct labeling of those points.

Next, two thresholds $t_1 < t_2$ were selected to give the sets $A=\{x_i: g(x_i) < t_1\}$ and $B=\{x_i: g(x_i) > t_2\}$, where it is assumed that the points in set A have label −1 and B have label +1. The thresholds $t_1$ and $t_2$ should be chosen according to the conditional probability of y given the distance from the hyperplane. In this experiment the thresholds were hand-selected based upon the distribution of correctly labeled examples in cross validation experiments.

Feature selection is performed using $CORR_{ub}$ using both the training set and the sets A and B to provide a sort of enlarged training set. Then, a SVM is trained on the original training set with the n best features from the resulting correlation scores. For each n, the best scores of the SVM were calculated by adjusting the threshold parameter.

Figure 22A:
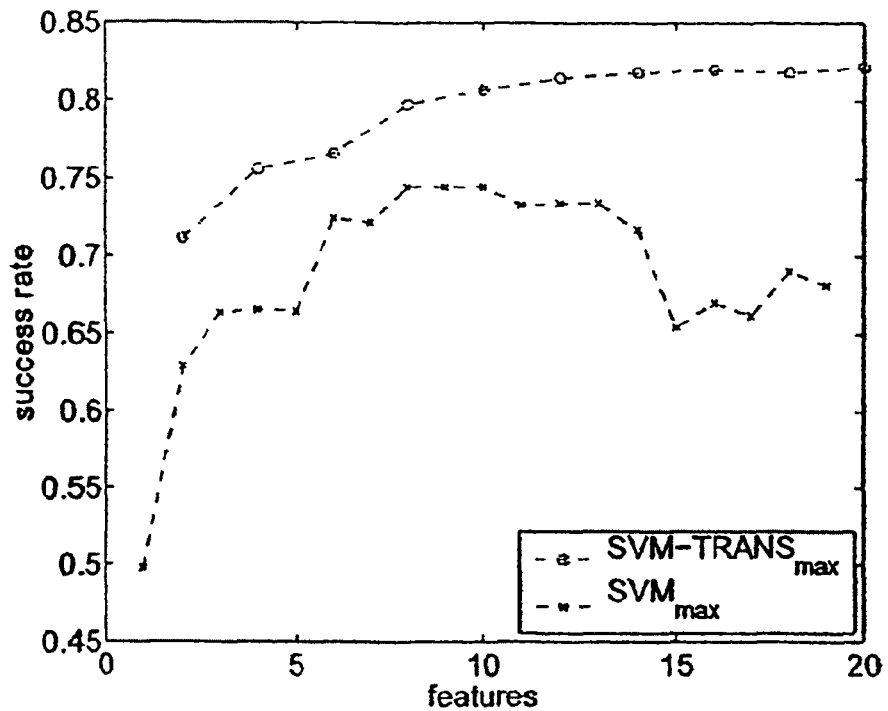
FIGS. 22a and b are plots showing the results of the transductive SVM using the $CORR_{ub}$ feature selection method.
Figure 22B:
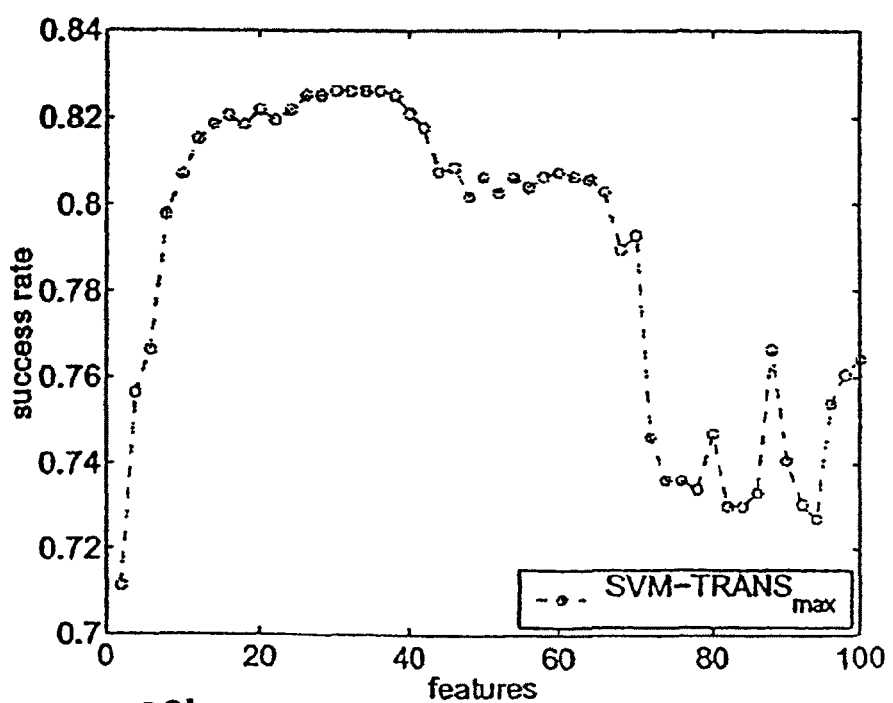
FIG. 22b. provides the results for the transductive method using 4 to 100 features.

This scheme could be repeated iteratively. The results of the transductive SVM using $CORR_{ub}$ feature selection compared with the inductive version, shown Tables 20a and b and FIG. 22, were quite positive. The best success rate for the transductive algorithm is 82.63% for 30-36 features.

TABLE 20a

| feature | 2 | 4 | 6 | 8 | 10 |
|---|---|---|---|---|---|
| SVM-TRANS$_{max}$ | 0.7115 | 0.7564 | 0.7664 | 0.7979 | 0.8071 |
| SVM$_{max}$ | 0.7574 | 0.7264 | 0.7275 | 0.7250 | 0.7449 |

TABLE 20b

| feature | 12 | 14 | 16 | 18 | 20 |
|---|---|---|---|---|---|
| SVM-TRANS$_{max}$ | 0.8152 | 0.8186 | 0.8206 | 0.8186 | 0.8219 |
| SVM$_{max}$ | 0.7574 | 0.7584 | 0.7454 | 0.7205 | 0.7156 |

In order to simplify the transduction experiments, a transductive approach of the $CORR_{ub}$ method was applied. This should remove some of the hyperparameters (e.g. the hyperparameters of the SVM) and make the computations faster, facilitating computation of several iterations of the transduction procedure, and the corresponding cross validation results.

To apply the transductive approach, a simple probabilistic version of the algorithm set forth above was designed:
1. Add the test examples to the training set but set their labels $y_i=0$ so their labels are unknown.

2. Choose n features using the score for a feature j, $$f_j = \sum_{Y_i>0} Y_i X_{ij} + 3 \sum_{Y_i<0} Y_i X_{ij}; \text{ (the } CORR_{ub} \text{ method).}$$

3. For each test example recalculate their labels to be: $y_i = f(g(x))$ where $g(x_i)$ is the sum of the values of the features (the features were selected in the previous step). The function $f$ can be based on an estimate of the conditional probability of y given $g(x_i)$. In this case, the selected function was $f(x)=\tan h(sx/n-b)$ where s and b were estimated to be the values s=4 and b=0.15. These values were selected by performing cross validation on different feature set sizes to give the values $g(x_i)$ of left out samples. The values are then selected by measuring the balanced loss after assigning labels.

4. Repeat from step 2 until the features selected do not change or a maximum number of iterations have occurred.

Figure 23A:
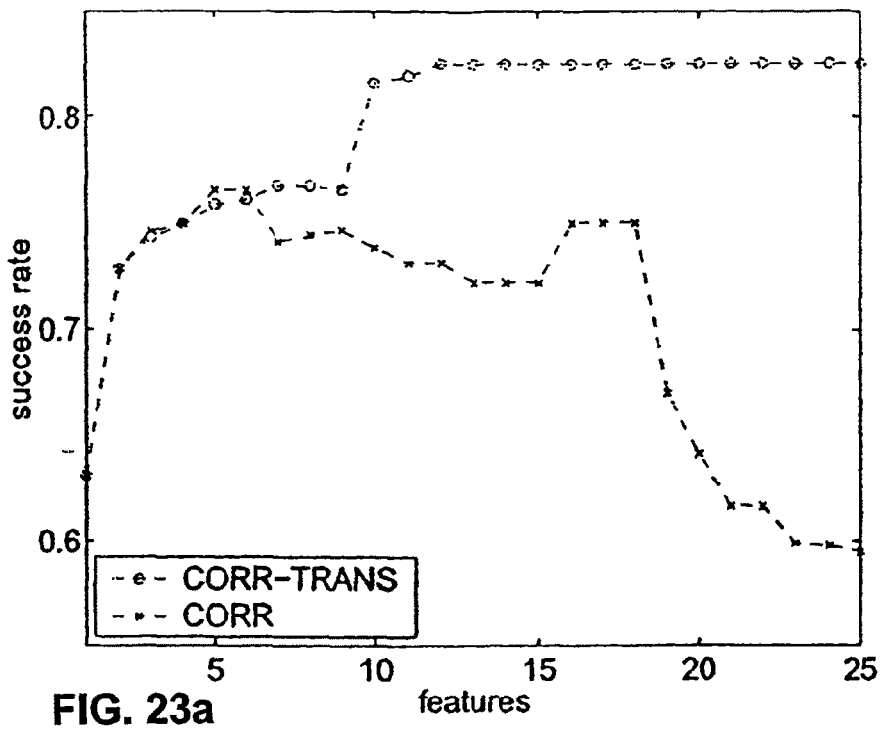
FIGS. 23a and b are plots showing the results of the transductive $CORR_{ub}^2$ method compared to the inductive version of the $CORR_{ub}^2$ method, with FIG. 23a showing the results or 4 to 25 features and FIG. 23b the results for 4 to 100 features.
Figure 23B:
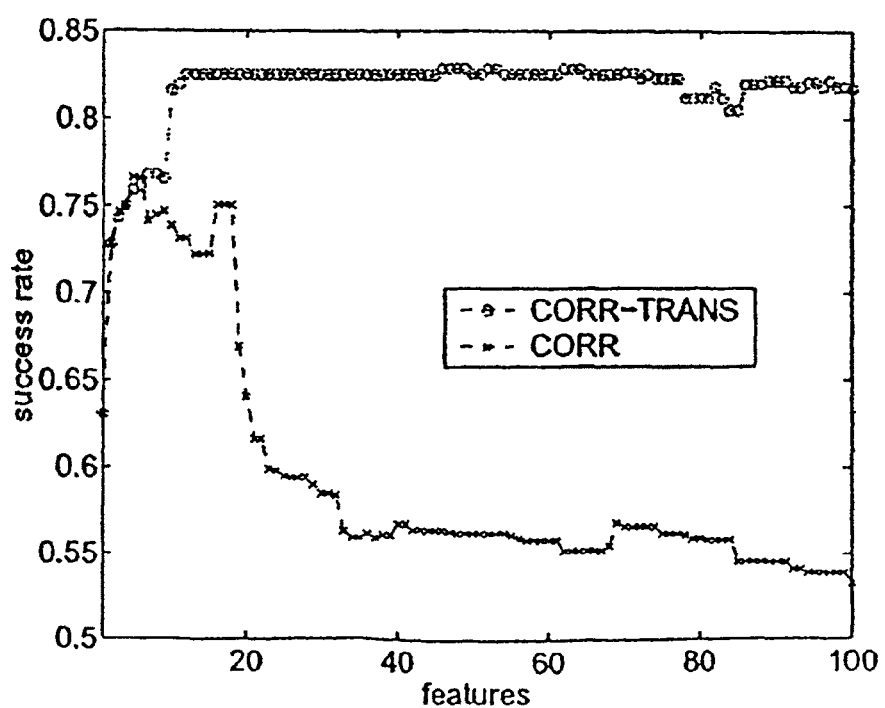

FIG. 23 shows the results of the transductive $CORR_{ub}^2$ method compared to the inductive version for from 4 to 100 features. The best success rate for the transductive algorithm is 82.86%. Again, the transductive results provide improvement over the inductive method. The transductive results are particularly robust with increasing numbers of features, up to one hundred features. After 200 features the results start to diminish, yielding only 77% success. At this same point, the inductive methods give 50% success, i.e., they no longer learn any structure. For 1000 features using the transductive method one obtains 58% and for 10000 features one no longer learns, obtaining 50%. Note also that for CORR (the inductive version), the cross validation results do not help select the correct model. This may be due to the small number of positive examples and the non-iid nature of the data. As the cross validation results are more or less equal in the transductive case as the number of features increases, it would be preferable to choose a smaller capacity model with less features, e.g., 10 features. Table 21 provides the results of the transductive $CORR_{ub}^2$ method, while Table 22 provides the results of the $CORR_{ub}^2$ inductive method, for test success, cross validation success and the corresponding standard deviation.

TABLE 21

| features | 1 | 5 | 10 | 15 | 20 | 25 | 30 | 35 | 40 |
|---|---|---|---|---|---|---|---|---|---|
| TRANS test | 0.6308 | 0.7589 | 0.8163 | 0.8252 | 0.8252 | 0.8252 | 0.8252 | 0.8252 | .08252 |
| TRANS cv | 0.6625 | 0.6746 | 0.6824 | 0.6703 | 0.6687 | 0.6687 | 0.6683 | 0.6683 | 0.6683 |
| TRANS cv-std | 0.074 | 0.089 | 0.083 | 0.088 | 0.089 | 0.090 | 0.089 | 0.089 | 0.089 |

TABLE 22

| features | 1 | 11 | 21 | 31 | 41 |
|---|---|---|---|---|---|
| $CORR_{ub}^2$ test | 0.6308 | 0.7315 | 0.6165 | 0.5845 | 0.5673 |
| $CORR_{ub}^2$ cv | 0.5176 | 0.6185 | 0.6473 | 0.6570 | 0.6677 |
| $CORR_{ub}^2$ cv-std | 0.013 | 0.022 | 0.032 | 0.04 | 0.04 |

In summary, feature selection scores and forward selection schemes which take into account the unbalanced nature of the data, as in the present example, are less likely to overfit than more complex backward selection schemes. Transduction is useful in taking into account the different distributions of the test sets, helping to select the correct features.

Single Feature Selection Using Ranking by Margin Value

The present method of feature selection comprises means for estimating the number of variables falsely called "significant" when variable selection is performed according to the SF-SVM (single feature support vector machine) criterion. In the case of the specific data, the goal is to select a subset of variables from a large costly microarray to construct less costly microarrays and perform more extensive experiments. The variables are ranked in order of best fit to achieve this separation and predict the fraction of false positives. While the present method is described in terms of gene selection, it should be noted that the method may be similarly applied to selection of other features.

In one embodiment, the design specifications of the low cost arrays are set, e.g. a maximum of n=500 variables on the array with a fraction of false positive not exceeding $f$=10%. A high cost array with a larger number of variables n'>>n is then chosen. The number p of experiments to be run on the large cost arrays is determined. The p experiments are run on the n' variable arrays and the SF-SVM method to rank the variables is used. The top n most promising variables are selected. The fraction g of falsely significant genes using the method outlined in the report are estimated. If g>$f$, more experiments on the large costly arrays need to be run and the whole procedure is iterated until g<$f$.

Example 8

Renal Cancer Dataset

1. The present example selects a subset of genes that are most characteristic of renal malignancies. The data consists of gene expression coefficients recorded with an expensive DNA microarray technology for a very small number of tumors (7 samples). The goal is to select the most promising subset of genes to design less expensive microarrays which include the selected subset of genes only, in order to conduct more extensive experiments. Results are presented using Support Vector Machine techniques.

Gene expression coefficients obtained from measurements on cDNA microarrays such as those available from Incyte Genomics, Inc. (Palo Alto, Calif.) were used for analysis. The data consists of seven arrays recording the relative expression coefficients of renal epithelial neoplasms. In each case, the cancerous tissue was hybridized competitively with normal tissue from the same patient. Positive numbers mean upregulation of the gene in cancer compared to normal, negative numbers indicate downregulation of the gene in cancer compared to normal (Ratios have been log 2 transformed). The data includes 5312 gene expression coefficients per tumor along with clone ID and a brief gene description for each coefficient is also listed.

Tumors are traditionally grouped according to cytogenic abnormalities. The seven arrays used to generate the dataset correspond to the following tissue types: Conventional (four samples) representing stages IIA, IIB, III and IV; Oncocytoma (two samples), types A and B; and Chromophobe (1 sample). The characteristics of the types of cells are summarized below:

Conventional (Also Known as "Clear Cell"):

This is the most common tissue type, representing 75-85% of tumors. Half of the patients presenting with conventional RCC (renal cell carcinoma) are already in advanced stage The Robson staging classification divides stages into: confinement to the renal parenchyma (stage I), tumor extension into the perirenal fat (stage II), tumor involvement of the renal vein or inferior vena cava (stage IIIa), or tumor involvement of local hilar lymph node or other vascular structures (stage IIIb). Stage IV classifies tumors involving adjacent organs or distant metastasis.

Conventional RCC develops in approximately one-third of patients with von Hippel-Lindau Syndrome. This is a deletion in the 3p region of the chromosome where a tumor suppressor gene is located. Mutations or deletions here can cause a loss of control, allowing certain cancers to develop where they would ordinarily be suppressed.

Conventional RCC does not respond well to chemotherapy. Other agents must be used, such a cytokines (IL2, Interferon alpha), or anti-angiogeneis agents to cut off blood supply. Surgery is commonly performed for all three, since a tissue sample must be obtained to diagnose based on the characteristics of the tissue.

Chromophobic:

This type represents 5% of tumors which are low grade tumors which they have malignant potential.

2. Oncocytoma:

This type is uncommon, with benign tumors which can metastasize and turn into the chromophobic type.

For analysis, the problem can be viewed as a two class or multiclass problem. Conventional cells always stand alone as a distinct entity. The chromophobe and oncocytomas can be grouped together because they are much more similar to each other than to the conventional type. In the first part of the study, the examples were split into two classes: all "conventional" (samples 1-4), and the others (samples 5-7). This allowed the application of a SF-SVM to derive statistically significant results for the screening of genes that are relevant to renal diseases. Multi-class methods were used to analyze the second phase data set collected using a smaller subset of pre-selected genes but a larger number of tumors.

This complements an analysis based on clustering (unsupervised learning). The present method of feature selection provides for ranking of genes according to how well they separate tumor categories, making direct use of the knowledge of these categories in a supervised learning scheme. The SF-SVM uses the size of the gap (margin) between classes as a ranking criterion. It is compared with a reference method using differences in mean class values. Both criteria use normalized gene expressions to account for each "gene-specific scatter", which is not taken into account in the fold change criterion. The reliability of the ranking is then quantified statistically.

The data was pre-processed by successively normalizing the columns, the rows and then, again, the columns of the matrix. Normalization consists of subtracting the mean and dividing by the standard deviation.

A singular value decomposition of the original data and of the preprocessed data was performed. In both cases the six first singular values were significantly different from zero.

Figure 24:
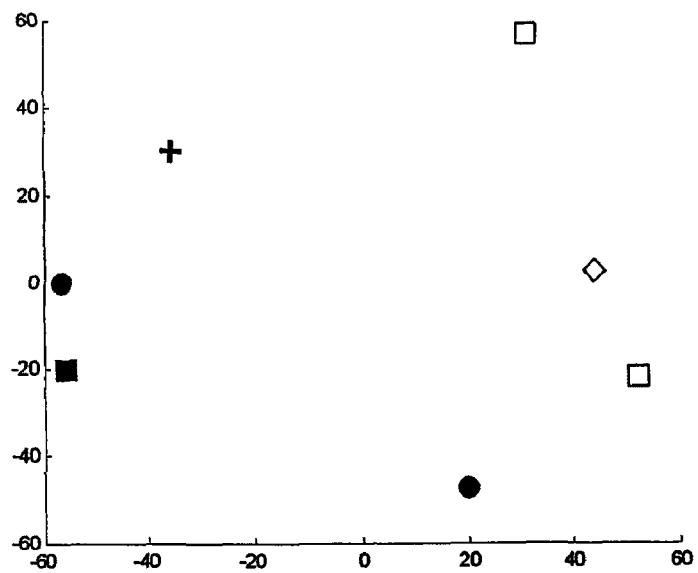
FIG. 24 is a scatter plot of the seven tumors in the two first gene principal components in an analysis of renal cancer.

The seven tumor examples were plotted in the space of the first two gene eigenvectors, both for non-normalized and normalized data. In both cases, the first class (tumors 1-4) was separated from the second class (tumors 5-7) along the first principal component (projection in the direction of the first eigenvector). The grouping of the tumors into sub-categories was not apparent. FIG. 24 provides the scatter plot for the normalized data for the different tissue types separated into two classes according to the first principal component (horizontal axis.) For class 1, the circle designates Conventional, stage II ("Cony. II"), the solid square designates Cony. III, and the plus sign corresponds to Cony. IV. For class 2, the open square corresponds to oncocytoma and the open diamond corresponds to chromophobe.

The preceding confirms the results obtained by clustering and supports the fact that tumors 1-4 are well separated from tumors 5-7

The exploratory data analysis indicated that class 1 (tumors 1-4) and class 2 (tumors 5-7) are easily separated. Genes are ranked according to how significantly they separate one class from the other. Using the SVM criterion, the number of genes falsely called significant in any given list of genes can be estimated. The result is compared to that obtained by the classical t-test method as a reference statistical method.

The size of the data set (seven tumors) does not permit classical machine learning analysis in which the data are split into a training set and a test set, or even to perform cross-validation experiments. Therefore, classical statistics methods of gene ranking evaluation were used. This differs from previous studies in which a novel criterion for gene ranking developed for prostate cancer data analysis was used.

Single Feature SVM ranks the genes according to their margin value, i.e., the distance between the extremal points of the two classes under study. For example, assume a gene is, on average, overexpressed for class 1 examples and underexpressed for class 2 examples. The margin is computed as the difference between the minimum value of the class 1 examples and the maximum value of the class 2 examples. To perform that analysis, it is important that the gene expression coefficients be normalized according to the pre-processing steps described above.

Other methods typically rank genes according to the average difference in expression coefficient. SF-SVM provides a better confidence that the genes selected are truly significant. Values for the top genes that were selected using SF-SVM are given in Tables 23 and 24. Table 23 includes genes underexpressed for class 1 (conventional) and overexpressed for class 2 (chromophobe/oncocytoma), while Table 24 lists genes overexpressed for class 1 and underexpressed for class 2. In both tables, the "Margin" is the SF-SVM ranking criterion. Its exponentiated value "Expmar" is also provided. All genes listed have a p-value less than 0.001. The sixth through nineteenth genes in Table 23 have a p-value less than 0.0005 and first five genes in the list have a p-value less than 0.0001. In Table 24, all genes have a probability less than 0.001 to be false positive. The first three genes listed in Table 24 have a probability of less than 0.0001 to be false positive, while the fourth through fourteenth entries have a probability of less than 0.0005 to be false positive.

TABLE 23

| Gene | Margin | Expmar | Description |
|---|---|---|---|
| 2082 | 1.56849 | 4.79938 | acetyl-Coenzyme A acetyltransferase 1 (acetoacetyl Coenzyme A thiolase) {Incyte PD: 3425159} |
| 2634 | 1.56815 | 4.79778 | glutamate decarboxylase 1 (brain, 67 kD) {Incyte PD: 2498815} |
| 2326 | 1.51024 | 4.52781 | JTV1 gene {Incyte PD: 1579679} |
| 2754 | 1.47959 | 4.39115 | glutaryl-Coenzyme A dehydrogenase {Incyte PD: 1998421} |
| 30 | 1.45895 | 4.30143 | KIAA0196 gene product {Incyte PD: 620885} |
| 3508 | 1.36831 | 3.92871 | Homo sapiens mRNA full length insert cDNA clone EUROIMAGE 26539 {Incyte PD: 1653974} |
| 4614 | 1.35769 | 3.8872 | complement component 1, q subcomponent binding protein {Incyte PD: 1552335} |
| 4450 | 1.33749 | 3.80945 | NADH dehydrogenase (ubiquinone) Fe—S protein 4 (18 kD) (NADH-coenzyme Q reductase) {Incyte PD: 2883487} |
| 4020 | 1.33483 | 3.79935 | conserved helix-loop-helix ubiquitous kinase {Incyte PD: 2746918} |
| 1736 | 1.33048 | 3.78285 | glutamic-oxaloacetic transaminase 2, mitochondrial (aspartate aminotransferase 2) {Incyte PD: 661259} |
| 4070 | 1.32378 | 3.7576 | Homo sapiens KB07 protein mRNA, partial cds {Incyte PD: 62790} |
| 4316 | 1.31658 | 3.73064 | junction plakoglobin {Incyte PD: 820580} |
| 2169 | 1.30404 | 3.68415 | ESTs {Incyte PD: 2591352} |
| 3466 | 1.30024 | 3.67017 | ESTs {Incyte PD: 2472605} |
| 648 | 1.28479 | 3.61389 | solute carrier family 11 (proton-coupled divalent metal ion transporters), member 2 {Incyte PD: 1684954} |
| 4947 | 1.25411 | 3.50471 | Incyte EST {Incyte PD: 1992727} |
| 4370 | 1.24593 | 3.47615 | solute carrier family 9 (sodium/hydrogen exchanger), isoform 1 (antiporter, Na+/H+, amiloride sensitive) {Incyte PD: 2054252} |
| 1623 | 1.21608 | 3.37393 | retinitis pigmentosa GTPase regulator {Incyte PD: 311313} |
| 306 | 1.21478 | 3.36955 | protein kinase, cAMP-dependent, regulatory, type II, beta {Incyte PD: 1968465} |
| 4475 | 1.18853 | 3.28226 | KIAA0580 protein {Incyte PD: 2722216} |
| 4468 | 1.18521 | 3.27138 | Down syndrome candidate region 1-like 1 {Incyte PD: 1375877} |
| 151 | 1.18385 | 3.26693 | peroxisomal biogenesis factor 7 {Incyte PD: 2722756} |
| 4159 | 1.15796 | 3.18344 | hydroxyacyl-Coenzyme A dehydrogenase/3-ketoacyl-Coenzyme A thiolase/enoyl-Coenzyme A hydratase (trifunctional protein), alpha subunit {Incyte PD: 1600442} |
| 3126 | 1.11533 | 3.05056 | KE2 protein {Incyte PD: 1994340} |

TABLE 24

| Gene | Margin | Expmar | Description |
|---|---|---|---|
| 2986 | 1.58551 | 4.881779 | tissue inhibitor of metalloproteinase 3 (Sorsby fundus dystrophy, pseudoinflammatory) {Incyte PD: 1998269} |
| 2041 | 1.478624 | 4.386906 | major histocompatibility complex, class II, DO beta {Incyte PD: 2200211} |
| 4015 | 1.409464 | 4.093759 | guanylate binding protein 1, interferon-inducible, 67 kD {Incyte PD: 521139} |
| 509 | 1.36113 | 3.900598 | bone morphogenetic protein 1 {Incyte PD: 1804401} |
| 423 | 1.321147 | 3.747718 | interferon regulatory factor 7 {Incyte PD: 2308952} |
| 1930 | 1.31463 | 3.723373 | vimentin {Incyte PD: 1522716} |
| 3717 | 1.262751 | 3.535132 | KIAA0677 gene product {Incyte PD: 876860} |
| 3040 | 1.262751 | 3.535132 | N-acetylglucosaminyl transferase component Gpi1 {Incyte PD: 1511484} |
| 1270 | 1.254365 | 3.50561 | adenosine A3 receptor {Incyte PD: 1989534} |
| 4086 | 1.231158 | 3.425193 | major histocompatibility complex, class II, DR beta 1 {Incyte PD: 2683564} |
| 3412 | 1.221229 | 3.391351 | chromosome condensation 1 {Incyte PD: 3180854} |
| 422 | 1.215801 | 3.372994 | delta sleep inducing peptide, immunoreactor {Incyte PD: 2307314} |
| 1387 | 1.212219 | 3.360933 | Human mRNA for SB classII histocompatibility antigen alpha-chain {Incyte PD: 1994472} |
| 1396 | 1.196186 | 3.307477 | solute carrier family 21 (prostaglandin transporter), member 2 {Incyte PD: 1648449} |
| 929 | 1.13331 | 3.10592 | vesicle-associated membrane protein 5 (myobrevin) {Incyte PD: 122826} |
| 3389 | 1.092242 | 2.98095 | lymphoid blast crisis oncogene {Incyte PD: 3029331} |

It was verified that CD74 is overexpressed in conventional, not in oncocytomas. (Its rank is 34, which is too low to appear in Table 24).

The p-values mentioned in the legend of the tables are computed as described in the following discussion. In the genes listed in Tables 23 and 24 having p-values less than 0.001, it is expected that only of the order of 5 genes at most will be random genes having no significance for the separation.

To compute the probabilities of false positive, the distribution of margin values for an identical number of examples as in the study (4 of one class and 3 of the other) were numerically evaluated. The examples of the two classes are drawn at random according to N(0,1). After rescaling, gene expression coefficients that are pure "noise" and do not carry information would be expected to be drawn according to the Normal law N(0,1) for both classes. The p-values are tabulated in Table 25, which provides the probabilities of obtaining a margin value equal to or larger than the tabulated margin for examples drawn at random according to N(0,1). To build the table, 100,000 drawings of four examples were taken for class 1 and three examples for class 2 according to N(0,1). With each drawing, the margin was computed. The estimated p-value is the fraction of drawings in which the margin exceeds the corresponding value given in the table.

TABLE 25

| pvalue | margin | expmar = exp(margin) |
|---|---|---|
| 0.500000 | −1.83 | 0.16 |
| 0.100000 | −0.55 | 0.57 |
| 0.050000 | −0.21 | 0.81 |
| 0.010000 | 0.41 | 1.50 |
| 0.005000 | 0.63 | 1.88 |
| 0.001000 | 1.09 | 2.98 |
| 0.000500 | 1.19 | 3.28 |
| 0.000100 | 1.37 | 3.94 |
| <0.000050 | 2.07 | 7.96 |

Figure 25:
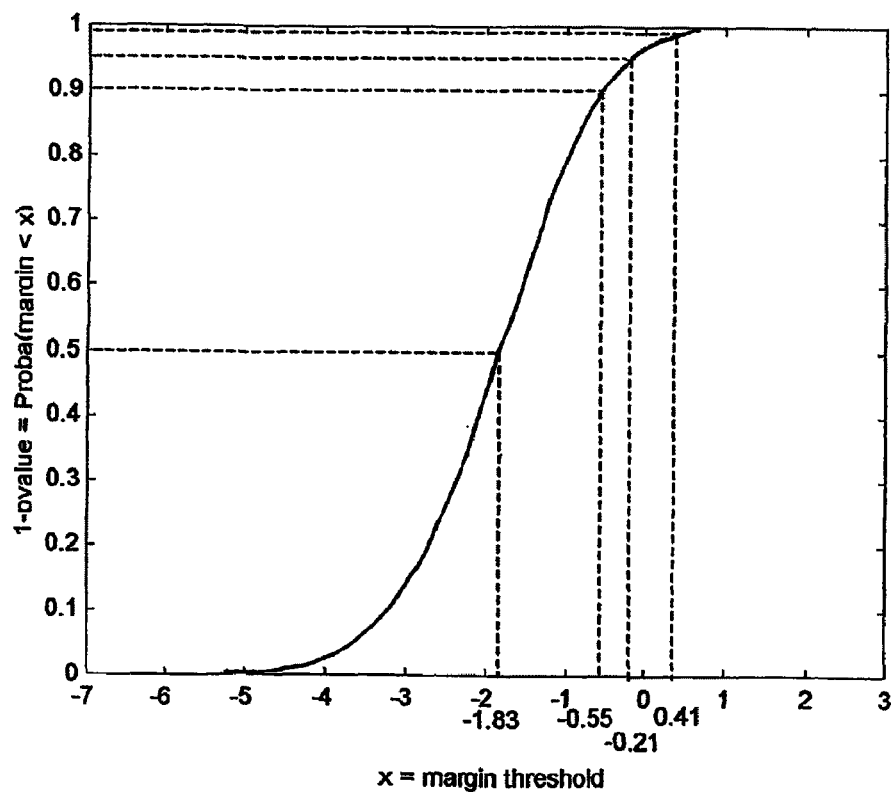
FIG. 25 is a graph of the distribution of margin values for 4 samples of one class drawn at random according to N(0,1) and 3 samples of another class drawn at random according to N(0,1).

FIG. 25 is a plot of the distribution of margin values for the combination of samples used to build Table 25. A few values extracted from this plot are shown in Table 25. For example, only 0.01 (1%) of "random" genes have a margin exceeding 0.41. A larger fraction of real genes separate the two classes with a margin exceeding that value (398 genes, that is 7% of the 5312 in the data set). Thus, among these 398 genes that have margin values exceeding 0.41, it is expected that, at most, 53 genes will be falsely called significant.

All methods rank genes according to how well the examples of one class are separated from the examples of the other class using a given criterion. The genes are indexed with the letter i and $w_i$ is the ranking criterion for a given gene. (+) denotes the class for which gene i is overexpressed on average and class and (−) the other class $\delta_i$ is denoted by the sign of $w_i$ (gene polarity), which is +1 if class (+) coincides with class 1 and −1 otherwise. Genes with positive $w_i$ are overexpressed for class 1 and underexpressed for class 2. Two types of criteria are compared, which are the difference in mean values and the difference in extremal values.

(1) Difference in mean values: Several methods are based on the difference in mean expression value of the two classes $\mu_i(+)$ and $\mu_i(-)$, normalized with a coefficient that reflects the intrinsic scatter of gene expression values of that gene. Typically, an average of the two intra-class standard deviations $\sigma_i(+)$ and $\sigma_i(-)$ is considered, e.g. for Golub's method $w_i=\delta_i(\mu_i(+)-\mu_i(-))/(\sigma i(+)+\sigma i(-))$ and for Fisher's criterion (sometimes referred to as single feature-linear discriminant analysis (SF-LDA)) $w_i=\delta_i(\mu_i(+)-\mu_i(-))/\sqrt{p(+)\sigma_i(+)^2+p(-)\sigma_i(-)^2}$. Other similar criteria include the t-test criterion and SAM that are well known to those of skill in the art. (2) Difference in extremal values: The criterion that used above is based on the difference in extremal values (margin). $s_i(+)$ is defined as the smallest observed value of class (+) and $s_i(-)$ the largest observed value of class (−). The criterion is then $w_i=\delta_i \exp(s_i(+)-s_i(-))$. The exponentiation permits accounting for overlapping classes that have negative margins. The SF-SVM criterion is not normalized.

Figure 26A:
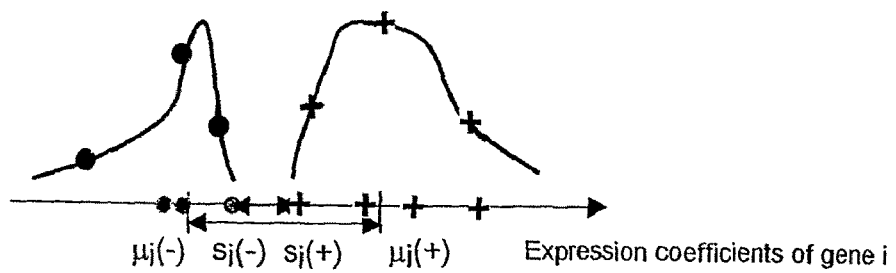
FIG. 26a illustrates results for a typical sample drawn from well-separated classes and FIG. 26b illustrates results for a model of an insignificant gene by randomly drawing examples of both classes from the same distribution N(0,1).
Figure 26B:
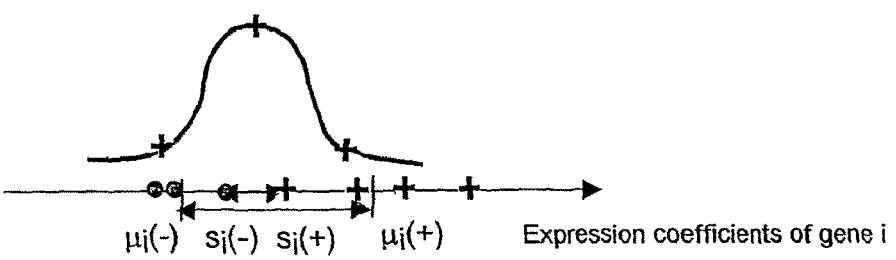

FIGS. 26a and 26b are plots of the hypothetical distributions of gene expression coefficients of a given gene for two categories of samples, where class (−) is indicated by the "●" on the curve and class (+) by the "+" on the curve. Sets of examples drawn from those distributions are indicated by "●" and "+" on the horizontal arrow. Criteria to determine whether a given gene separates the two classes are derived by examining either the difference in mean values $\mu_i(+)-\mu_i(-)$ or the difference in extremal values $s_i(+)-s_i(-)$. FIG. 26a illustrates a typical sample drawn from well separated classes. FIG. 26b models a purely insignificant gene by drawing at random examples of both classes from the same distribution N(0,1). It is unlikely that the means of the examples of the two classes will be well separated. It is even more unlikely that the extremal values will be separated by a positive margin.

For both type of criteria, it is possible to assess the fraction of genes falsely called significant in a given list of genes. A gene is called "significant" for the class separation at hand if its criterion exceeds a certain threshold value. To estimate the number of genes falsely called significant, the above-described method for determining statistical significance can be used. The estimated p-value is the fraction of drawings in which the criterion exceeds a given threshold.

Figure 27:
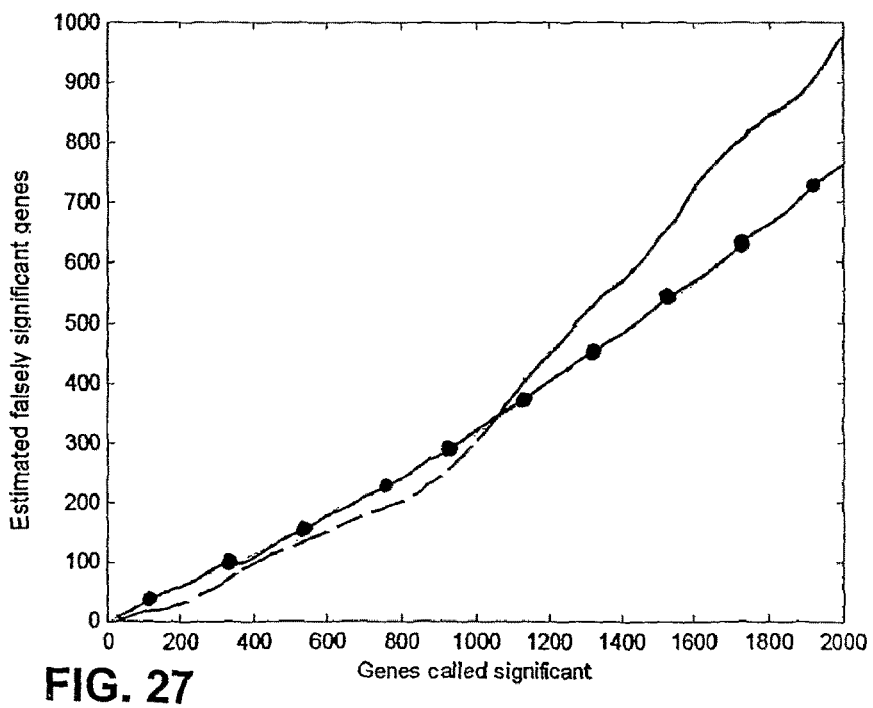
FIG. 27 is a plot of genes called "significant" versus estimated falsely significant genes for comparing criteria of gene ranking.

Therefore, for any criterion threshold value, it is possible to obtain an upper bound estimate of the number of genes called significant that are plotted as a function of the number of genes called significant. FIG. 27 provides a plot of an estimated upper bound on the number of genes falsely called significant as a function of the number of genes called significant. The estimate uses 100,000 genes drawn at random according to N(0,1). The results using the SF-LDA (t-test) method are indicated by the curve with circles. The other line indicates the results of the SF-SVM, with the dashed portion of that line, below the intersection of the two lines, corresponding to genes that separate the two classes perfectly. The SF-SVM criterion that uses the difference between extremal points as ranking criterion incurs a smaller number of genes falsely called significant than does the SF-LDA criterion that uses the difference of the means. Above the point where the two curves cross, SF-LDA becomes more reliable. The SF-SVM criterion appears to be slightly superior to the SF-LDA criterion because, for a given number of genes called significant, it provides a smaller estimated number of genes falsely called significant where positive margins (genes separating perfectly the two classes) can be defined.

Looking at the multi-class problem, a Support Vector Machine method is applied for finding genes that can discriminate between diseases with a large margin. In this case, "margin" means the difference of gene expression between two borderline patients carrying a different disease.

The small number of patients in each disease category does not allow the quantitative assessment of the validity of the approach on the present dataset. Nonetheless, the method will become useful when larger numbers of patients become available.

Similar to the two class problem, genes can be ranked according a criterion that characterize how well they individually discriminate between classes. As discussed above, two types of methods can be used: (1) methods based on differences in mean values; and (2) methods based on margins The well known Fisher criterion or Linear Discriminant Analysis (LDA) criterion pertains to the first method, while the SVM criterion pertain to the second method. The multi-class criteria are generalizations of the two-class criteria explained previously.

In the experiments, the data is first normalized as described above. The problem is considered as having five classes (in this case, diseases) based on the five tissue types discussed above: Conventional II (2 patients); Conventional III (1 patient); Conventional IV (1 patient); Oncocytoma (2 patients); and Chromophobe (1 patient).

The multi-class gene ranking method was applied to select 19 genes that are potentially related to the target, which are listed in Table 26.

TABLE 26

| | |
|---|---|
| small inducible cytokine A2 (monocyte chemotactic protein 1, homologous to mouse Sig-je) | {Incyte PD: 1511342} |
| creatine kinase, mitochondrial 2 (sarcomeric) | {Incyte PD: 57382} |
| ribosomal protein S11 | {Incyte PD: 1813409} |
| zinc finger protein 238 | {Incyte PD: 2555828} |
| cytochrome P450, subfamily IIJ (arachidonic acid epoxygenase) polypeptide 2 | {Incyte PD: 1597231} |
| mal, T-cell differentiation protein | {Incyte PD: 504786} |
| lectin, galactoside-binding, soluble, 3 (galectin 3) | {Incyte PD: 2921194} |
| abundant in neuroepithelium area | {Incyte PD: 637576} |
| Vimentin | {Incyte PD: 1522716} |
| KIAA0439 protein | {Incyte PD: 1712888} |
| defensin, beta 1 | {Incyte PD: 2912830} |
| ESTs | {Incyte PD: 1644648} |
| thrombospondin 2 | {Incyte PD: 2804667} |
| parvalbumin | {Incyte PD: 2289252} |
| propionyl Coenzyme A carboxylase, alpha polypeptide | {Incyte PD: 196975} |
| ATP synthase, H+ transporting, mitochondrial F1 complex, alpha subunit, isoform 1, cardiac muscle | {Incyte PD: 3206210} |
| collagen, type I, alpha 1 | {Incyte PD: 782235} |
| ATPase, H+ transporting, lysosomal (vacuolar proton pump), beta polypeptide, 56/58 kD, isoform 1 | {Incyte PD: 2676425} |
| ESTs | {Incyte PD: 1635864} |

Figure 28A:
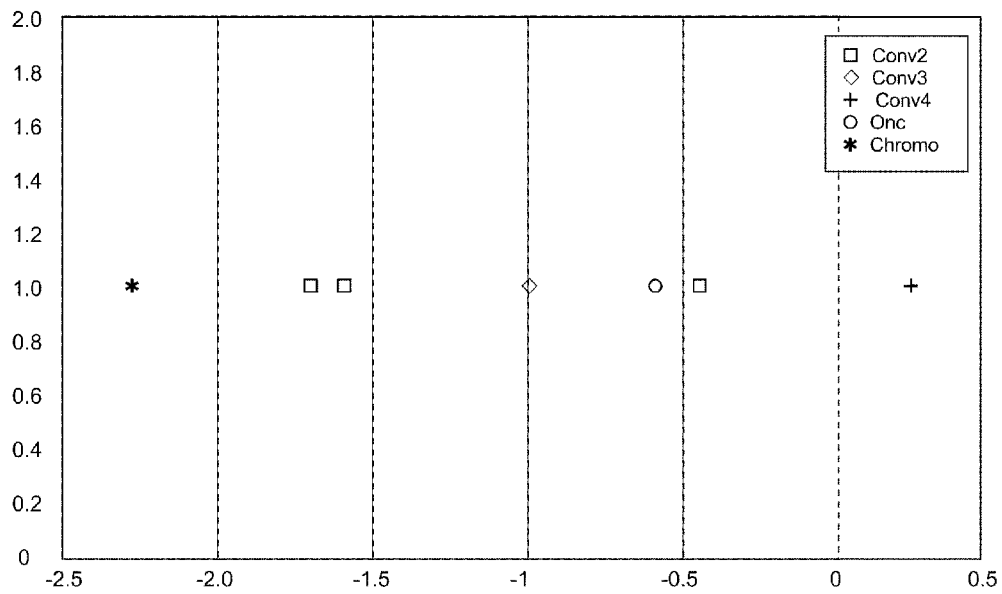
FIG. 28a is the plot for small inducible cytokine A2 (monocyte chemotactic protein 1, homologous to mouse Sig-je)
Figure 28B:
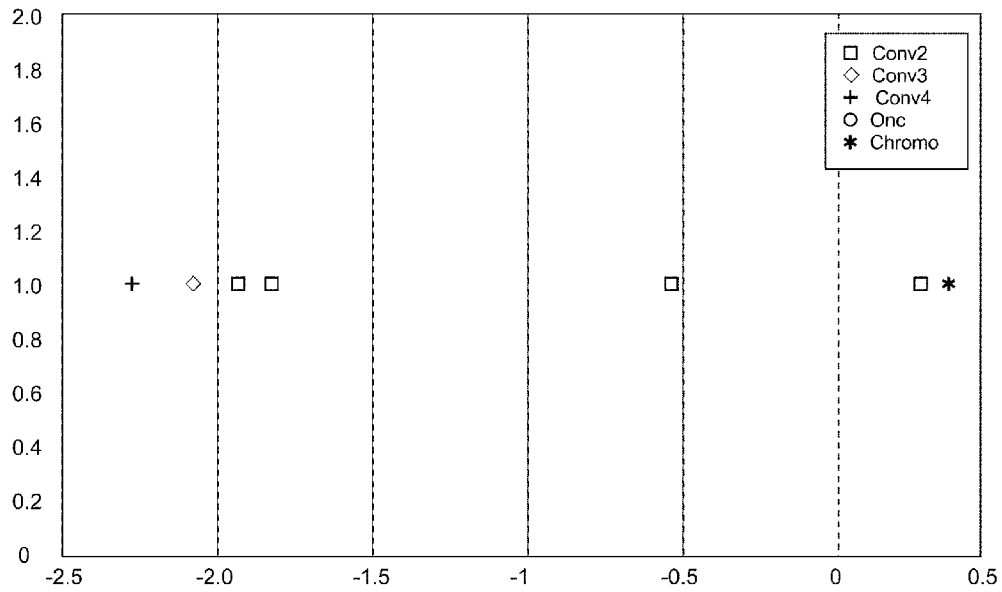
FIG. 28b is the plot for ATP synthase, H+ transporting, mitochondrial F1 complex, alpha subunit, isoform 1, cardiac muscle.

Among the listed genes, two genes are shown which exhibit a pattern for which patients from the same class are grouped and disease grades show a progression for the "conventional" patients. Referring to FIGS. 28*a* and 28*b*, the expression of the two genes potentially related to the five diseases is classified using the multi-class method. FIG. 28*a* shows the results for small inducible cytokine A2 (monocyte chemotactic protein 1, homologous to mouse Sig-je), {Incyte PD:1511342}. FIG. 28*b* shows the results for ATP synthase, H+ transporting, mitochondrial F1 complex, alpha subunit, isoform 1, cardiac muscle {Incyte PD:3206210}. The legend indicates the names of the different classes with abbreviations where (Conv=Conventional, Onc=Oncocytoma and Chromo=Chromophobe). Using the genes identified according to the present method, gene expression levels in tissue from patients can be tested for screening for genetic predisposition to and diagnosis of renal cancer and for treatment and monitoring of response to treatments such a chemotherapy or other appropriate therapy for renal cancer.

The present method of feature selection uses statistical methods to estimate the fraction of genes that might be falsely called significant in a given list of genes that appear to separate well the 4 examples of conventional RCC from the 3 examples of chromophobe or oncocytoma. The two methods used are the conventional t-test (SF-LDA) and SF-SVM. Both methods are in good agreement, however, genes that separate perfectly the two classes identified by SF-SVM do so with a smaller predicted number of genes falsely called significant. The gene ranking provided can be used to select genes that are most promising to build a new microarray with a more directed approach. It should be noted that, because of the small number of examples available, there is a certain degree of uncertainty as to the validity of the genes identified. In the top 1000, about 1/3 of the genes are suspicious. This number drops to 1/8 in the list of top 40 genes of Table 23 and 24. Given enough examples, statistical tests similar to those used for the two-class problem would to assess the number of genes falsely called significant with respect to the multi-class separation. Such a quantitative evaluation of the discriminant power of the genes can be performed with on the order of 30 patients per disease category.

According to the present invention, a number of different methods are provided for selection of features for use in a learning machine using data that best represents the essential information to be extracted from the data set. The inventive methods provide advantages over prior art feature selection methods by taking into account the interrelatedness of the data, e.g., multi-label problems. The features selection can be performed as a pre-processing step, prior to training the learning machine, and can be done in either input space or feature space.

It should be understood, of course, that the foregoing relates only to preferred embodiments of the present invention and that numerous modifications or alterations may be made therein without departing from the spirit and the scope of the invention as set forth in the appended claims. Such alternate embodiments are considered to be encompassed within the spirit and scope of the present invention. Accordingly, the scope of the present invention is described by the appended claims and is supported by the foregoing description.

The invention claimed is:

1. A computer-implemented method comprising:
(a) inputting into a computer processor programmed to execute a support vector machine a set of training examples having known labels with regard to two or more classes, each training example described by a vector of feature values for a plurality of features, the support vector machine comprising a decision function having a plurality of weights, wherein each feature has a corresponding weight;
(b) training the support vector machine by optimizing the plurality of weights so that a cost function is minimized and support vectors comprising a subset of the training examples are defined, wherein the decision function is based on the support vectors;
(c) computing ranking criteria using the optimized plurality of weights, wherein the ranking criterion estimates for each feature the effect on the cost function of removing that feature, and wherein features having the smallest effect on the cost function have the smallest ranking criteria;
(d) eliminating one or more features corresponding to the smallest ranking criteria to yield a reduced set of features;
(e) repeating steps (c) through (d) for the reduced set of features for a plurality of iterations until a subset of features of predetermined size remains, wherein the subset of features comprises determinative features for separating the set of training examples into the two or more classes; and
(f) generating at a printer or display device an output comprising a listing of the determinative features.

2. The method of claim 1, wherein step (d) comprises eliminating more than one feature corresponding to the smallest ranking criteria in a single iteration of steps (c) and (d).

3. The method of claim 1, wherein step (d) comprises eliminating more than one feature corresponding to the smallest ranking criteria in at least the first iteration of steps (c) and (d) and in later iterations, eliminating one feature for each iteration.

4. The method of claim 1, wherein step (d) comprises eliminating more than one feature corresponding to the smallest ranking criteria so that the number of features is reduced by a factor of two for each iteration.

5. The method of claim 1, wherein the set of training examples comprises gene expression values obtained from DNA microarrays and the determinative features comprise determinative genes.

6. The method of claim 1, further comprising generating an observation tree having a plurality of nodes, a first path comprising nodes corresponding to the determinative features, and a plurality of alternative paths, wherein nodes in the alternative paths are identified by removing a top ranked feature of the determinative features and repeating steps (c) and (d) so that alternative determinative features are identified.

7. A computer-program product embodied on a non-transitory computer-readable medium comprising instructions for executing a support vector machine, and further comprising instructions for:
training the support vector machine to determine a value for each feature in a group of features provided by a set of training samples having known labels corresponding to two or more classes, wherein training comprises generating a kernel matrix of components, each component comprising a dot product of two training samples, and adjusting a multiplier corresponding to each training sample to minimize a cost function;
eliminating at least one feature with a minimum value from the group to provide a reduced group of features;
generating an updated kernel matrix using the reduced group of features while keeping the multiplier unchanged;
determining an updated value for each feature in the reduced group of features;
repeating the steps of eliminating at least one feature, generating an updated kernel matrix and determining an updated value until a predetermined number of features remains; and
outputting a ranked list of features.

8. The computer-program product of claim 7, wherein the minimum value of a feature corresponds to a smallest change in the cost function when the feature is eliminated.

9. The computer-program product of claim 7, wherein the value of a feature corresponds to a weight in a decision function of the support vector machine.

10. The computer-program product of claim 7, wherein the step of eliminating comprises eliminating more than one feature corresponding to the minimum value.

11. The computer-program product of claim 7, wherein the step of eliminating comprises eliminating more than one feature corresponding to the minimum value in at least the first iteration of the step of eliminating and in later iterations, eliminating one feature for each iteration.

12. The computer-program product of claim 7, wherein the step of eliminating comprises eliminating more than one feature corresponding to the minimum value so that the number of features is reduced by a factor of two for each iteration.

13. A non-transitory machine-readable medium comprising a plurality of instructions, which in response to being executed, result in a computing system:
(a) training a support vector machine by generating a kernel matrix from a set of training samples and adjusting a multiplier corresponding to each training sample to minimize a cost function;
(b) determining a weight value for each feature in a group of features that describe the training samples;
(c) eliminating at least one feature with a minimum weight value from the group;
(d) generating an updated kernel matrix while keeping the multiplier unchanged;
(e) updating the weight value for each feature of the group based on the updated kernel matrix;
(f) repeating steps (c) through (e) until a predetermined number of features remains to generate a ranked list of features; and
(g) generating a report to a printer or display device comprising the ranked list of features.

14. The non-transitory machine-readable medium of claim 13, wherein step (c) comprises eliminating more than one feature corresponding to the minimum weight value in a single iteration of steps (b) and (c).

15. The non-transitory machine-readable medium of claim 13, wherein step (c) comprises eliminating more than one feature corresponding to the minimum weight value in at least the first iteration of steps (b) and (c) and in later iterations, eliminating one feature for each iteration.

16. The non-transitory machine-readable medium of claim 13, wherein step (c) comprises eliminating more than one feature corresponding to the minimum weight value so that the number of features is reduced by a factor of two for each iteration.

17. The non-transitory machine-readable medium of claim 13, wherein the set of training examples comprises gene expression values obtained from DNA microarrays and the determinative features comprise determinative genes.

18. A non-transitory machine-readable medium comprising a plurality of instructions, which in response to being executed, result in a computing system:
identifying a determinative subset of features that are most correlated to patterns in sample data by:
retrieving a training data having class labels with respect to the patterns from a memory in communication with a computer processor programmed for executing a support vector machine comprising a kernel;
calculating a kernel matrix using the training data to determine a value for each feature in the group of features;
eliminating at least one feature with a minimum value from the group;
calculating an updated kernel matrix, each component of the updated kernel matrix comprising a dot product of two training samples provided by at least a part of the training data that corresponds to the eliminated feature;
determining an updated value for each remaining feature of the group of features based on the updated kernel matrix;
repeating steps eliminating, calculating an updated kernel matrix and determining an updated value for a plurality of iterations until a pre-determined number of features in the group remain; and
generating an output comprising a ranked list of features, wherein the features in the ranked list comprise the determinative subset of features for predicting patterns in new data.

19. The non-transitory machine-readable medium of claim 18, wherein eliminating comprises eliminating multiple features from the group so that the number of features is reduced by the closest power of two to the number of remaining features.

20. The non-transitory machine-readable medium of claim 18, wherein the one or more features removed in eliminating comprises up to half of the remaining features.

21. The non-transitory machine-readable medium of claim 18, wherein eliminating comprises eliminating a plurality of features so that the number of features in the first iteration is reduced by up to half of the remaining features until a specified number of features remain and thereafter removing one feature per iteration.

22. A computer-implemented method comprising:
  (a) inputting into a computer processor programmed to execute a support vector machine a set of training examples having known labels with regard to two or more classes, each training example described by a vector of feature values for a plurality of features, the support vector machine comprising a decision function having a plurality of weights, wherein each feature has a corresponding weight;
  (b) training the support vector machine by optimizing the plurality of weights so that a cost function is minimized and support vectors comprising a subset of the training examples are defined, wherein the decision function is based on the support vectors;
  (c) computing ranking criteria using the optimized plurality of weights, wherein the ranking criterion estimates for each feature the effect on the cost function of removing that feature, and wherein features having the smallest effect on the cost function have the smallest ranking criteria;
  (d) eliminating one or more features corresponding to the smallest ranking criteria to yield a reduced set of features;
  (e) repeating steps (c) through (d) for the reduced set of features for a plurality of iterations until a subset of features of predetermined size remains, wherein the subset of features comprises determinative features for separating the set of training examples into the two or more classes; and
  (f) transferring a listing of the determinative features to a media.

23. The method of claim 22, wherein step (d) comprises eliminating more than one feature corresponding to the smallest ranking criteria in a single iteration of steps (c) and (d).

24. The method of claim 22, wherein step (d) comprises eliminating more than one feature corresponding to the smallest ranking criteria in at least the first iteration of steps (c) and (d) and in later iterations, eliminating one feature for each iteration.

25. The method of claim 22, wherein step (d) comprises eliminating more than one feature corresponding to the smallest ranking criteria so that the number of features is reduced by a factor of two for each iteration.

26. The method of claim 22, further comprising displaying the listing on a display device.

27. The method of claim 22, wherein the media comprises a disk drive or a removable media.

28. The non-transitory machine-readable medium of claim 18, wherein generating an output comprises transferring the output to a disk drive or a removable media.

29. The non-transitory machine-readable medium of claim 18, wherein generating an output comprises displaying the output on a display device.

30. The computer-program product of claim 7, wherein outputting a ranked list of features comprises transferring the ranked list of features to a disk drive or a removable media.

31. The computer-program product of claim 7, wherein outputting a ranked list of features comprises displaying the ranked list of features on a display device.

32. A non-transitory machine-readable medium comprising a plurality of instructions, which in response to being executed, result in a computing system:
  (a) training a support vector machine by generating a kernel matrix from a set of training samples and adjusting a multiplier corresponding to each training sample to minimize a cost function;
  (b) determining a weight value for each feature in a group of features that describe the training samples;
  (c) eliminating at least one feature with a minimum weight value from the group;
  (d) generating an updated kernel matrix while keeping the multiplier unchanged;
  (e) updating the weight value for each feature of the group based on the updated kernel matrix;
  (f) repeating steps (c) through (e) until a predetermined number of features remains to generate a ranked list of features; and
  (g) transferring the ranked list of features to a media.

33. The non-transitory machine-readable medium of claim 32, wherein step (c) comprises eliminating more than one feature corresponding to the minimum weight value in a single iteration of steps (b) and (c).

34. The non-transitory machine-readable medium of claim 32, wherein step (c) comprises eliminating more than one feature corresponding to the minimum weight value in at least the first iteration of steps (b) and (c) and in later iterations, eliminating one feature for each iteration.

35. The non-transitory machine-readable medium of claim 32, wherein step (c) comprises eliminating more than one feature corresponding to the minimum weight value so that the number of features is reduced by a factor of two for each iteration.

36. The non-transitory machine-readable medium of claim 32, wherein the set of training examples comprises gene expression values obtained from DNA microarrays and the determinative features comprise determinative genes.

37. The non-transitory machine-readable medium of claim 31, further comprising displaying the listing on a display device.

38. The non-transitory machine-readable medium of claim 31, wherein the media comprises a disk drive or a removable media.

* * * * *